(12) United States Patent
West et al.

(10) Patent No.: US 11,370,863 B2
(45) Date of Patent: Jun. 28, 2022

(54) ORAL CARE COMPOSITIONS COMPRISING PHOSPHONO-PHOSPHATE AND ANIONIC GROUP CONTAINING POLYMERS

(71) Applicant: The Procter & Gamble Company, Cincinnati, OH (US)

(72) Inventors: Ryan Michael West, West Chester, OH (US); Scott Leroy Cron, Liberty Township, OH (US); Yingkun Jin, Mason, OH (US); William Michael Glandorf, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 77 days.

(21) Appl. No.: 17/087,651

(22) Filed: Nov. 3, 2020

(65) Prior Publication Data

US 2021/0047475 A1 Feb. 18, 2021

Related U.S. Application Data

(62) Division of application No. 16/216,428, filed on Dec. 11, 2018, now Pat. No. 11,198,763.

(60) Provisional application No. 62/597,217, filed on Dec. 11, 2017.

(51) Int. Cl.
| | |
|---|---|
| *A61K 8/81* | (2006.01) |
| *A61Q 11/00* | (2006.01) |
| *C08F 8/40* | (2006.01) |
| *C08F 30/02* | (2006.01) |
| *C08F 230/02* | (2006.01) |
| *C08F 220/38* | (2006.01) |
| *C08G 79/04* | (2006.01) |
| *C08F 220/56* | (2006.01) |
| *C07F 9/38* | (2006.01) |
| *C08F 290/06* | (2006.01) |
| *C08F 8/14* | (2006.01) |
| *C08F 220/06* | (2006.01) |
| *C08F 299/02* | (2006.01) |
| *C08F 6/04* | (2006.01) |
| *C08F 8/26* | (2006.01) |
| *C08F 8/48* | (2006.01) |
| *C08F 130/02* | (2006.01) |
| *C08G 65/26* | (2006.01) |
| *C08F 8/02* | (2006.01) |
| *C07F 9/6571* | (2006.01) |
| *C08F 228/02* | (2006.01) |
| *C08F 8/44* | (2006.01) |
| *C08F 8/12* | (2006.01) |
| *C07F 9/6587* | (2006.01) |
| *A61K 8/91* | (2006.01) |
| *C08G 65/335* | (2006.01) |
| *C08F 220/58* | (2006.01) |
| *C08G 81/02* | (2006.01) |

(52) U.S. Cl.
CPC ........ *C08F 220/382* (2020.02); *A61K 8/8111* (2013.01); *A61K 8/8152* (2013.01); *A61K 8/8158* (2013.01); *A61K 8/8188* (2013.01); *A61K 8/91* (2013.01); *A61Q 11/00* (2013.01); *C07F 9/3865* (2013.01); *C07F 9/3869* (2013.01); *C07F 9/3895* (2013.01); *C07F 9/6587* (2013.01); *C07F 9/657181* (2013.01); *C08F 6/04* (2013.01); *C08F 8/02* (2013.01); *C08F 8/12* (2013.01); *C08F 8/14* (2013.01); *C08F 8/26* (2013.01); *C08F 8/40* (2013.01); *C08F 8/44* (2013.01); *C08F 8/48* (2013.01); *C08F 30/02* (2013.01); *C08F 130/02* (2013.01); *C08F 220/06* (2013.01); *C08F 220/38* (2013.01); *C08F 220/56* (2013.01); *C08F 220/58* (2013.01); *C08F 220/585* (2020.02); *C08F 228/02* (2013.01); *C08F 230/02* (2013.01); *C08F 290/062* (2013.01); *C08F 299/024* (2013.01); *C08G 65/2609* (2013.01); *C08G 65/3355* (2013.01); *C08G 79/04* (2013.01); *C08F 2800/10* (2013.01); *C08F 2810/50* (2013.01); *C08G 81/025* (2013.01); *C08G 2650/24* (2013.01)

(58) Field of Classification Search
None
See application file for complete search history.

(56) References Cited

U.S. PATENT DOCUMENTS

| | | | |
|---|---|---|---|
| 2,946,725 | A | 7/1960 | Norris |
| 3,070,510 | A | 12/1962 | Cooley |
| 3,678,154 | A | 7/1972 | Widder et al. |
| 3,959,458 | A | 5/1976 | Agricola et al. |
| 3,976,619 | A | 8/1976 | Morgan |
| 4,051,234 | A | 9/1977 | Gieske et al. |
| 4,340,583 | A | 7/1982 | Wason |

(Continued)

FOREIGN PATENT DOCUMENTS

| | | |
|---|---|---|
| WO | 03009855 A2 | 2/2003 |
| WO | 03050128 A1 | 6/2003 |
| WO | WO2004017334 | 2/2004 |

OTHER PUBLICATIONS

International Search Report with written opinion, dated Mar. 25, 2019, 14 pages.

(Continued)

*Primary Examiner* — Brian Gulledge
(74) *Attorney, Agent, or Firm* — Parker D. McCrary

(57) ABSTRACT

Disclosed are oral care compositions of novel phosphono-phosphate and anionic group containing polymer compositions that have targeted uses with divalent cations and surfaces having divalent cations. These compounds can be used to deliver anionic character to surfaces such as calcium hydroxyapatite for use in oral care applications.

16 Claims, 3 Drawing Sheets

(56) References Cited

U.S. PATENT DOCUMENTS

| | | | |
|---|---|---|---|
| 4,416,877 | A | 11/1983 | Bentzen |
| 4,585,845 | A | 4/1986 | Engelhardt |
| 4,696,987 | A | 9/1987 | Duersch |
| 5,004,597 | A | 4/1991 | Majeti et al. |
| 5,281,410 | A | 1/1994 | Lukacovic et al. |
| 5,575,652 | A | 11/1996 | Gaffar et al. |
| 5,578,293 | A | 11/1996 | Prencipe et al. |
| 5,939,052 | A | 8/1999 | White, Jr. et al. |
| 6,173,049 | B1 | 1/2001 | Malik |
| 6,187,295 | B1 | 2/2001 | Glandorf |
| 6,190,644 | B1 | 2/2001 | McClanahan et al. |
| 6,350,436 | B1 | 2/2002 | Glandorf et al. |
| 6,713,049 | B1 | 3/2004 | White, Jr. |
| 7,399,756 | B2 | 7/2008 | Jomaa |
| 7,871,992 | B2 | 1/2011 | Jomaa |
| 8,017,596 | B2 | 9/2011 | Montero |
| 2003/0165442 | A1 | 9/2003 | Baig |
| 2004/0204541 | A1 | 10/2004 | Pelosi |
| 2005/0063921 | A1 | 3/2005 | Charmot |
| 2005/0271602 | A1 | 12/2005 | Milanovich |
| 2006/0030546 | A1 | 2/2006 | Jomaa |
| 2006/0241087 | A1 * | 10/2006 | Montero ............... A61P 31/18 558/194 |
| 2007/0041914 | A1 | 2/2007 | Gaffar et al. |
| 2008/0249067 | A1 | 10/2008 | Jomaa |
| 2008/0269099 | A1 | 10/2008 | Magennis et al. |
| 2010/0204184 | A1 | 8/2010 | Montero |
| 2011/0112054 | A1 | 5/2011 | Jomaa |
| 2013/0071464 | A1 | 3/2013 | Downes |
| 2016/0324741 | A1 | 11/2016 | Baig et al. |
| 2019/0175485 | A1 | 6/2019 | West |
| 2019/0177348 | A1 | 6/2019 | Cron |
| 2019/0177451 | A1 | 6/2019 | West |
| 2019/0177456 | A1 | 6/2019 | West |
| 2019/0177489 | A1 | 6/2019 | West |
| 2019/0177490 | A1 | 6/2019 | West |

OTHER PUBLICATIONS

Anbar et al. "Organic Polymeric Polyphosphonates as Potential Preventive Agents of Dental Caries: In Vitro Experiments", J Dent Res, vol. 53, No. 4, pp. 867-878, 1974.

Bingol et al., "Characterization of Oligo(vinyl phosphonate)s by High-Resolution Electrospray Ionization Mass Spectometry: Implications for the Mechanism of Polymerization", Macromolecules 2008, 41, pp. 1634-1639.

Brunet et al., "Engineering of Microcrystaline Solid-State Networks Using Cross-Linked y-Zirconium Phosphate/Hypophosphite with Nonrigid Polyethylenoxadiphosphonates. Easy Access to Porously Dynamic Solids with Polar/Nonpolar Pores", Chem. Mater. 2005, 17, pp. 1424-1433.

Database WPI, Week 200425, Thomson Scientific, London GB, AN 2004-268983, XP002789049.

Frantz et al., "Synthesis and Solid-State NMR Studies of P-Vinylbenzylphosphonic Acid", Chemistry—A European Journal, vol. 9, Issue 3, pp. 770-775, 2003.

Ibrahim Zgani et al. "Synthesis of Prenyl Pyrophosphonates as New Potent Phosphorantigens Inducing Selective Activation of Human V[gamma] 9V[delta] 2 T Lymphocytes", Journal of Medicinal Chemistry, vol. 47, No. 18, Aug. 1, 2004, pp. 4600-4612, XP055569445.

Kim et al., "Characterization of Poly(styrene-b-vinylbenzylphosphonic acid) Copolymer by Titration and Thermal Analysis", Macromolecular Research, vol. 15 No. 6, pp. 587-594, 2007.

Monge et al., "Polymerization of Phosphorus-Containing (Meth)acrylate Monomers", published May 7, 2014 http://pubs.rsc.org | doi:10.1039/9781782624523-00001, 18 pgs.

Schroeder et al., "The Reaction of Phosphorus Trichloride and Oxygen with Polymers", Journal of Polymer Science, vol. 47, Issue 149, pp. 417-433, 1960.

Valentijn A R P M et al: "A novel approach towards the synthesis ofpyrophosphate analogues of farnesyl pyrophoshate", Recueil Des Travaux Chimiques Des Pays-Bas vol. 113, No. 12, Dec. 12, 1994 (Dec. 12, 1994), pp. 563-566, XP002789048, DOI: 10.1002/RECL. 19941131206 [retrieved on Sep. 2, 2010]figure 1; compounds 2, 14.

All Office Actions, U.S. Appl. No. 16/215,699.
All Office Actions, U.S. Appl. No. 16/215,702.
All Office Actions, U.S. Appl. No. 16/215,704.
All Office Actions, U.S. Appl. No. 16/216,428.
All Office Actions; U.S. Appl. No. 16/216,039.
All Office Actions; U.S. Appl. No. 16/216,329.
U.S. Appl. No. 17/087,650, filed Nov. 3, 2020, to Ryan West et. al.
U.S. Appl. No. 17/087,651, filed Nov. 3, 2020, to Ryan West et. al.

* cited by examiner

ORAL CARE COMPOSITIONS COMPRISING PHOSPHONO-PHOSPHATE AND ANIONIC GROUP CONTAINING POLYMERS

TECHNICAL FIELD OF THE INVENTION

The present invention relates to novel phosphono-phosphate and anionic group containing polymers. The present invention further relates to using oral care compositions comprising the novel polymers.

BACKGROUND OF THE INVENTION

Chemical structures that interact with multivalent cations in solution and with surfaces containing multivalent cations are useful for manipulation of these systems. Polyphosphates and pyrophosphate, for example, have been used as builders in laundry and dish formulations to control calcium and in drilling muds to prevent precipitation. They have also been used in the oral care industry to help control tartar and reduce the thickness of the pellicle layer on teeth resulting in a slick tooth feel. Similarly, bisphosphonates, and hydroxy-bisphosphonates are active components in osteoporosis pharmaceuticals due to their strong interaction with calcium hydroxy apatite surfaces and are also used as crystal growth inhibitors in dishwashing liquids and boiler systems.

Each of these examples suffer from an inherent limitation. Polyphosphates are prone to degradation over time in aqueous solutions at all pH's, ultimately leading to an increase in ortho phosphate in solution. Polyphosphate salts are also quite anionic in nature and are not soluble in non-polar organic systems. Polyphosphates are, however, generally safe for consumption and find use in different food products. Bisphosphonates and hydroxy-bisphosphonates are, conversely, stable in water for long periods of time, and can, depending upon the nature of the organic group attached to the bisphosphonate carbon, be made quite soluble in organic systems.

Bisphosphonates, however, are active to bone surfaces and hence cannot be used in foods or other systems where they might be accidently consumed due to their potent pharmacology. Polymers containing bisphosphonates of sufficient molecular weight to not pass through the intestinal wall would likely not be bone active, however any low molecular weight residual monomers or oligomers that could pass through the intestinal wall make the use of such polymers prohibitive in potential consumable contexts. In addition, since bisphosphonates do not break down readily, their activity can persist in the environment after use.

Therefore, a need still exists for a phosphate composition that does not easily degrade and is safe for human consumption.

SUMMARY OF THE INVENTION

It has surprisingly been found that the phosphono-phosphate chemical group ameliorates the concerns of polyphosphates and bisphosphonates while finding utility in similar systems. In particular, polymers that contain a phosphono-phosphate group, whether by incorporation of a monomer containing a phosphono-phosphate group, or by post polymerization modification to add a phosphono-phosphate group, along with an anionic group can be used in numerous applications in which polyphosphates and bisphosphonate containing structures are used. Such applications generally include those in which binding interactions are involved with multivalent cations both in solution and on surfaces containing bivalent cations. Phosphono-phosphate and anionic containing polymers can also be used in applications where polyphosphates and bisphosphonate use is limited. The phosphono-phosphate group is conditionally stable and will only release phosphate under acidic or catalyzed conditions. Hence the phosphono-phosphate group is more stable than polyphosphate, but not as stable as bisphosphonates. This enables formulation into systems where an anionic containing polymer provides benefit and where non-detrimental effects of consumption and water stability are a must.

In certain embodiments, the present invention is directed to oral care compositions including a novel polymer comprising a phosphono-phosphate group and an anionic group wherein said phosphono-phosphate group has the structure of Formula 1:

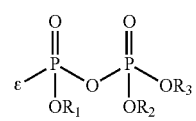

Formula 1 wherein:
ε is the site of attachment to a carbon atom in the polymer backbone, side group, or side chain;
$R_1$ is selected from the group consisting of —H, alkyl, alkanediyl-alkoxy, metal salt having Na, K, Ca, Mg, Mn, Zn, Fe, or Sn cation, amine cation salt, and a structure of Formula 2:

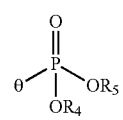

Formula 2 wherein:
θ is the site of attachment to Formula 1,
$R_4$ and $R_5$ are independently selected from the group consisting of —H, alkyl, alkanediyl-alkoxy, metal salt having Na, K, Ca, Mg, Mn, Zn, Fe, or Sn cation, and amine cation salt;
$R_2$ is selected from the group consisting of —H, alkyl, alkanediyl-alkoxy, metal salt having Na, K, Ca, Mg, Mn, Zn, Fe, or Sn cation, amine cation salt, and a structure of Formula 3:

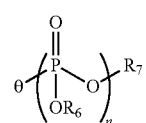

Formula 3 wherein:
θ is the site of attachment to Formula 1,
$R_6$, and $R_7$ are independently selected from the group consisting of —H, alkyl, alkanediyl-alkoxy, metal salt having Na, K, Ca, Mg, Mn, Zn, Fe, or Sn cation, and amine cation salt, and
n is an integer from 1 to 22; and $R_3$ is selected from the group consisting of —H, alkyl, alkanediyl-alkoxy, metal salt having Na, K, Ca, Mg, Mn, Zn, Fe, or Sn cation, and amine cation salt; and said anionic group is covalently bound to the polymer backbone, side group, or side chain and is selected from the chemical group consisting of phosphate, phosphonate, phosphinate, sulfate, sulfonate, sulfinate, mercapto, carboxylate, hydroxyamino, amine oxide, and hydroxamate.

In certain embodiments, at least one monomer used to create the polymer comprises the phosphono-phosphate group. In another embodiment, at least one monomer used to create the polymer comprises the anionic group. In another embodiment, at least one monomer used to create said polymer comprises said anionic group and at least one monomer used to create said polymer comprises said phosphono-phosphate group. In another embodiment, the phosphono-phosphate group is added during a post-polymerization modification.

In certain embodiments, when at least one monomer used to create the polymer comprises the phosphono-phosphate group, said at least one monomer has the structure of Formula 4:

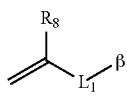

Formula 4 wherein:
- β is the site of attachment to the phosphono-phosphate group of Formula 1;
- $R_8$ is selected from the group consisting of —H and —CH$_3$;
- $L_1$ is selected from the group consisting of a chemical bond, arenediyl, and a structure of Formula 5:

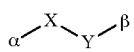

Formula 5 wherein:
- α is the site of attachment to the alkenyl radical in Formula 4;
- β is the site of attachment to the phosphono-phosphate group of Formula 1;
- X is selected from the group consisting of the structures in Formulas 6-12;

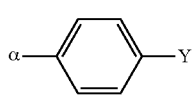

Formula 6

Formula 7

Formula 8

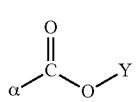

Formula 9

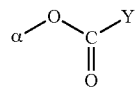

Formula 10

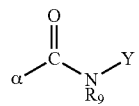

Formula 11

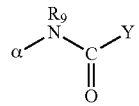

Formula 12 wherein:
- $R_9$ is selected from the group consisting of —H, alkyl $(C_{1-8})$, phosphonoalkyl, and phosphono(phosphate)alkyl; and
- Y is selected from the group consisting of alkanediyl, alkoxydiyl, alkylaminodiyl and alkenediyl.

In certain embodiments, when at least one monomer used to create the polymer comprises the phosphono-phosphate group, and said at least one monomer has the structure of Formula 4, $L_1$ is a covalent bond. In another embodiment, when at least one monomer used to create the polymer comprises the phosphono-phosphate group, and said at least one monomer has the structure of Formula 4, $L_1$ has the structure of Formula 5. In another embodiment, when at least one monomer used to create the polymer comprises the phosphono-phosphate group, said at least one monomer has the structure of Formula 4, and $L_1$ has the structure of Formula 5, the structure of X is selected from the group consisting of Formula 6, Formula 9 and Formula 11.

In certain embodiments, said anionic group is selected from phosphate, phosphonate, sulfate, sulfonate or carboxylate. In another embodiment, said anionic group is sulfonate. In another embodiment, said anionic group is carboxylate. In another embodiment, said anionic group is phosphonate.

In certain embodiments, when at least one monomer used to create the polymer comprises an anionic group, said at least one monomer further comprises an alkenyl group of the structure of Formula 13:

Formula 13 wherein:
- $R_{10}$ is selected from the group consisting of H or CH$_3$ and
- $L_2$ is a linking group to the anionic group.

In certain embodiments, when at least one monomer used to create the polymer comprises an anionic group, said at least one monomer further comprises an alkenyl group of the structure of Formula 14:

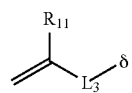

Formula 14 wherein:
$R_{11}$ is selected from the group consisting of H and alkyl;
δ is the site of attachment to the anionic group;
$L_3$ is i selected from the group consisting of a chemical bond, arenediyl, and a structure of Formula 15;

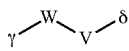

Formula 15 wherein:
γ is the site of attachment to the alkenyl radical;
δ is the site of attachment to the anionic group;
W is selected from the structures in Formulas 16-22:

Formula 16

Formula 17

Formula 18

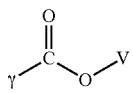

Formula 19

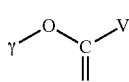

Formula 20

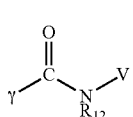

Formula 21

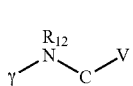

Formula 22 wherein:
$R_{12}$ is selected from the group consisting of —H, and alkyl$_{(C1-8)}$; and
V is selected from the group consisting of alkanediyl, alkoxydiyl, alkylaminodiyl, and alkenediyl.

In certain embodiments, when at least one monomer used to create the polymer comprises an anionic group, said at least one monomer is selected from the group consisting of vinyl phosphonate, vinyl sulfonate, acrylate, methyl vinyl phosphonate, methyl vinyl sulfonate, methacrylate, styrene phosphonate, styrene sulfonate, vinyl benzene phosphonate, vinyl benzene sulfonate, 2-acrylamido-2-methyl propane sulfonate (AMPS), and 2-Sulfopropyl Acrylate (SPA).

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 99.9:0.1 to 0.1:99.9, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 99:1 to 1:99, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 90:10 to 10:90, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 70:30 to 30:70, respectively.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus.

These and other features, aspects, and advantages of the present invention will become evident to those skilled in the art from reading of the present disclosure.

DETAILED DESCRIPTION OF THE INVENTION

Figure 1:
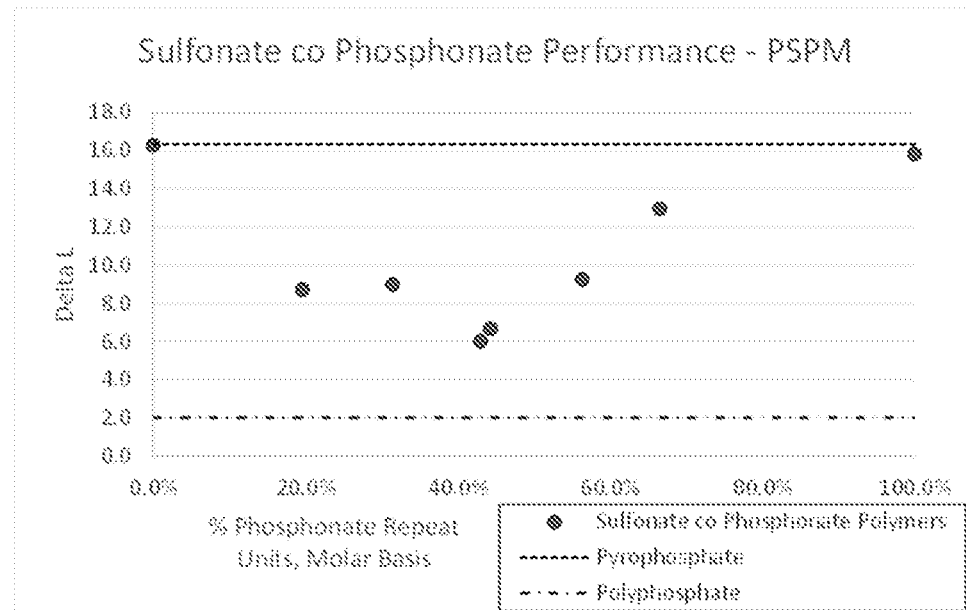
FIG. 1 is a chart showing polymer performance.

While the specification concludes with claims particularly pointing and distinctly claiming the invention, it is believed the present invention will be better understood from the following description.

All percentages herein are by moles of the compositions unless otherwise indicated.

All ratios are molar ratios unless otherwise indicated.

All percentages, ratios, and levels of ingredients referred to herein are based on the actual amount of the ingredient by moles, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

Definitions

The terms "site" or "site of attachment" or "point of attachment" all mean an atom having an open valence within a chemical group or defined structural entity that is designated with a symbol such as a simple dash (-) or a lower case letter from the greek alphabet followed by a dash or a line (e.g. α-, β-, etc.) to indicate that the so-designated atom connects to another atom in a separate chemical group via a chemical bond. The symbol "⁓" when drawn perpendicular across a bond

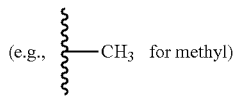

(e.g., ⁓—CH₃ for methyl)

also indicates a point of attachment of a chemical group. It is noted that the point of attachment is typically only identified in this manner for larger chemical groups in order to unambiguously assist the reader in identifying the point of attachment to the atom from which the bond extends. A site or point of attachment on a first chemical group or defined structural entity connects to a site or point of attachment on a second chemical group or defined structural entity via either single, double, or triple covalent bonds in order to satisfy the normal valency of the atoms connected.

The term "radical" when used with a chemical group indicates any connected group of atoms, such as a methyl group, a carboxyl group, or a phosphono-phosphate group that is part of a larger molecule.

When used in the context of a chemical group: "hydrogen" means —H; "hydroxy" means —OH; "oxo" means =O; "carbonyl" means —C(=O)—; "carboxy" and "carboxylate" mean —C(=O)OH (also written as —COOH or —CO2H) or a deprotonated form thereof; "amino" means —NH2; "hydroxyamino" means —NHOH; "nitro" means —NO2; "imino" means =NH; "amine oxide" means N*O— where N has three covalent bonds to atoms other than O; "hydroxamic" or "hydroxamate" means —C(O)NHOH or a deprotonated form thereof; in a monovalent context "phosphate" means —OP(O)(OH)₂ or a deprotonated form thereof; in a divalent context "phosphate" means —OP(O)(OH)O— or a deprotonated form thereof; "phosphonate" means C—P(O)(OH)2 or a deprotonated form thereof, where the C has a normal valence of four and three covalent bonds to atoms other than P; "phosphono-phosphate" means a phosphonate that is chemically bound through a shared oxygen atom to at least one phosphate such as but not limited to phosphono-monophosphate C—P(O)(OH)OP(O)(OH)₂, phosphono-diphosphate C—P(O)(OP(O)(OH)₂)OP(O)(OH)₂, phosphono-cyclodiphosphate

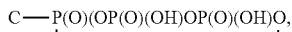

C—P(O)(OP(O)(OH)OP(O)(OH)O, phosphono-pyrophosphate C—P(O)(OH)OP(O)(OH)OP(O)(OH)₂, and phosphono-polyphosphate C—P(O)(OH)(OP(O)(OH))ₙOP(O)(OH)₂, where n is an integer between 1 and 100, or a deprotonated form thereof, where the C has a normal valence of four and three covalent bonds to atoms other than P; "phosphinate" means C—P(O)(OH)(C) or a deprotonated form thereof, where both C have a normal valence of four and three additional bonds to atoms other than P; "sulfate" means —OS(O)₂OH or deprotonated form thereof; "sulfonate" means CS(O)₂OH or a deprotonated form thereof where the C has a normal valence of four and three additional bonds to atoms other than S; "sulfinate" means CS(O)OH or a deprotonated form thereof, where the C has a normal valence of four and three additional bonds to atoms other than S; "mercapto" means —SH; "thio" means=S; "sulfonyl" means —S(O)2-; and "sulfinyl" means —S(O)—.

For the chemical groups and classes below, the following parenthetical subscripts further define the chemical group/class as follows: "(Cn)" defines the exact number (n) of carbon atoms in the chemical group/class. "(C≤n)" defines the maximum number (n) of carbon atoms that can be in the chemical group/class, with the minimum number as small as possible for the chemical group in question, e.g., it is understood that the minimum number of carbon atoms in the chemical group "alkenyl$_{(C≤8)}$" or the chemical class "alkene$_{(C≤8)}$" is two. For example, "alkoxy$_{(C≤8)}$" designates those alkoxy groups having from 1 to 8 carbon atoms. (Cn-n') defines both the minimum (n) and maximum number (n') of carbon atoms in the chemical group. Similarly, alkyl$_{(C2-8)}$ designates those alkyl groups having from 2 to 8 carbon atoms, inclusive.

The term "cation" refers to an atom, molecule, or a chemical group with a net positive charge including single and multiply charged species. Cations can be individual atoms such as metals, non-limiting examples include $Na^+$ or $Ca^{+2}$, individual molecules, non-limiting examples include $(CH_3)_4N^+$, or a chemical group, non limiting examples include-$N(CH_3)_3^+$. The term "amine cation" refers to a particular molecular cation, of the form $NR_4^+$ where the four substituting R moieties can be independently selected from H and alkyl, non-limiting examples include $NH_4^+$ (ammonium), $CH_3NH_3^+$ (methylammonium), $CH_3CH_2NH_3^+$ (ethylammonium), $(CH_3)_2NH_2^+$ (dimethylammonium), $(CH_3)_3NH^+$ (trimethyl ammonium), and $(CH_3)_4N^+$ (tetramethylammonium).

The term "anion" refers to an atom, molecule, or chemical group with a net negative charge including single and multiply charged species. Anions can be individual atoms, for example but not limited to halides $F^-$, $Cl^-$, $Br^-$, individual molecules, non limiting examples include $CO_3^{-2}$, $H_2PO_4^-$, $HPO_4^{-2}$, $PO_4^{-3}$, $HSO_4^-$, $SO_4^{-2}$, or a chemical group, non limiting examples include sulfate, phosphate, sulfonate, phosphonate, phosphinate, sulfonate, mercapto, carboxylate, amine oxide, hydroxamate and hydroxyl amino. Deprotonated forms of previously defined chemical groups are considered anionic groups if the removal of the proton results in a net negative charge. In solutions, chemical groups are capable of losing a proton and become anionic as a function of pH according to the Henderson-Hasselbach equation (pH=pKa+$\log_{10}$([$A^-$]/[HA]; where [HA] is the molar concentration of an undissociated acid and [$A^-$] is the molar concentration of this acid's conjugate base). When the pH of the solution equals the pKa value of functional group, 50% of the functional group will be anionic, while the remaining 50% will have a proton. Typically, a functional group in solution can be considered anionic if the pH is at or above the pKa of the functional group.

The term "salt" or "salts" refers to the charge neutral combination of one or more anions and cations. For example, when R is denoted as a salt for the carboxylate group, —COOR, it is understood that the carboxylate (—COO—) is an anion with a negative charge −1, and that the R is a cation with a positive charge of +1 to form a charge neutral entity with one anion of charge −1, or R is a cation with a positive charge of +2 to form a charge neutral entitity with two anions both of −1 charge.

The term "saturated" as used herein means the chemical compound or group so modified has no carbon-carbon double and no carbon-carbon triple bonds, except as noted below. In the case of substituted versions of saturated chemical groups, one or more carbon oxygen double bond or a carbon nitrogen double bond may be present. When such a bond is present, then carbon-carbon double bonds that may occur as part of keto-enol tautomerism or imine/enamine tautomerism are not precluded.

The term "aliphatic" when used without the "substituted" modifier signifies that the chemical compound/group so modified is an acyclic or cyclic, but non-aromatic hydrocarbon chemical compound or group. In aliphatic chemical compounds/groups, the carbon atoms can be joined together in straight chains, branched chains, or non-aromatic rings (alicyclic). Aliphatic chemical compounds/groups can be saturated, that is joined by single bonds (alkanes/alkyl), or unsaturated, with one or more double bonds (alkenes/alkenyl), or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic, or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr, or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu, or tBu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, —P(O)(OH)$_2$, —P(O)(OH)OP(O)(OH)$_2$, —OP(O)(OH)$_2$, —OP(O)(OH)OP(O)(OH)$_2$, —S(O)$_2$(OH), or —OS(O)$_2$(OH). The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, —CH$_2$CH$_2$Cl, —CH$_2$P(O)(OH)$_2$, —CH$_2$P(O)(OH)OP(O)(OH)$_2$, —CH$_2$S(O)$_2$(OH), and —CH$_2$OS(O)$_2$(OH). The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "phosphonoalkyl" is a subset of substituted alkyl, in which one or more of the hydrogen has been substituted with a phosphonate group and no other atoms aside from carbon, hydrogen, phosphorous, and oxygen are present. The groups, —CH$_2$P(O)(OH)$_2$, and —CH$_2$CH$_2$P(O)(OH)$_2$, and the corresponding deprotonated forms thereof, are non-limiting examples of a phosphonoalkyl.

The term "phosphono(phosphate)alkyl" is a subset of substituted alkyl, in which one or more of the hydrogen has been substituted with a phosphono-phosphate group and no other atoms aside from carbon, hydrogen, phosphorous, and oxygen are present. The groups, —CH$_2$P(O)(OH)OP(O)(OH)$_2$, and —CH$_2$CH$_2$P(O)(OH)OP(O)(OH)$_2$, and corresponding deprotonated forms thereof, are non-limiting examples of phosphono(phosphate)alkyl.

The term "sulfonoalkyl" is a subset of substituted alkyl, in which one or more of the hydrogen has been substituted with a sulfonate group and no other atoms aside from carbon, hydrogen, sulfur, and oxygen are present. The groups, —CH$_2$S(O)$_2$OH and —CH$_2$CH$_2$S(O)$_2$OH, and the corresponding deprotonated forms thereof, are non-limiting examples of a sulfonoalkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —C(CH$_3$)=CH$_2$ (methyl-vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, >C=CH$_2$ (vinylidine), —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (-Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

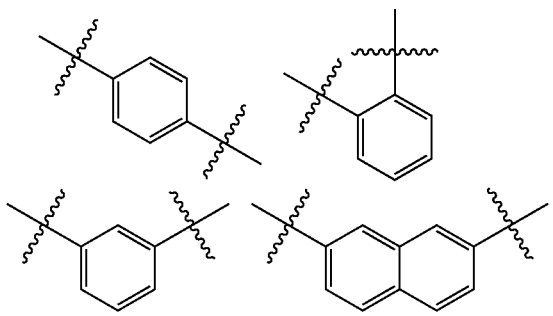

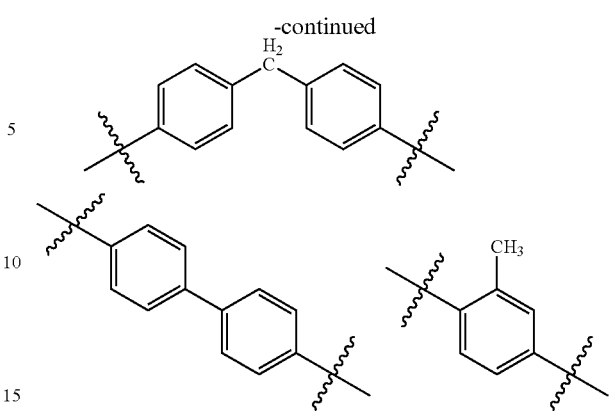

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO (formyl), —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkanediyl-alkoxy" refers to -alkanediyl-O-alkyl. A non-limiting example of alkanedyl-alkoxy is CH$_2$—CH$_2$—O—CH$_2$—CH$_3$. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR) or a deprotonated form thereof, in which R is an alkyl, as that term is defined above. Nonlimiting examples of alkylphosphate groups include: —OP(O)(OH)(OMe) and —OP(O)(OH)(OEt). The term "dialkylphosphate" when used without the "substituted" modifier refers to the group —OP(O)(OR) (OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

Linking group means either a covalent bond between two other defined groups, or a series of covalently bound atoms that connect two other defined groups where in the series of covalently bound atoms have no open valences other than the sites of attachment to the two other defined groups. Non-limiting examples of a linking group include a covalent bond, alkanediyl, alkenediyl, arenediyl, alkoxydiyl, and alkylaminodiyl.

As used herein, a "chiral auxiliary" refers to a removable chiral group that is capable of influencing the stereoselectivity of a reaction. Persons of skill in the art are familiar with such compounds, and many are commercially available.

Other abbreviations used herein are as follows: DMSO, dimethyl sulfoxide; DMF, dimethylformamide; MeCN, acetonitrile; MeOH, methanol; EtOH, ethanol; EtOAc, ethyl acetate; tBuOH, tert-butanol; iPrOH, isopropanol; cHexOH, cyclohexanol; Ac$_2$O, acetic anhydride; AcOOH, peracetic acid; HCO$_2$Et, ethyl formate; THF, tetrahydrofuran; MTBE, methyl tert-butyl ether; DME, dimethoxyethane; NBS, N-bromosuccinimide; CDI, carbonyldiimidazole; DIEA, diisopropylethylamine; TEA, triethylamine; DMAP, dimethylaminopyridine; NaOH, sodium hydroxide; AAPH, 2,2'-azobis(2-methylpropionamidine) dihydrochloride; CTA, 1-Octanethiol; APS, ammonium persulfate; TMP, trimethyl phosphate; VPA, vinyl phosphonic acid; VPP, vinyl phosphono-monophosphate; VPPP, vinyl phosphono-pyrophosphate MVPP, methyl-vinyl phosphono-monophosphate; SVS, sodium vinyl sulfonate; AMPS, sodium 2-acrylamido-2-methyl propane sulfonic acid; SPA, 3-sulfopropyl acrylate potassium salt; 22A2MPA2HCl, 2,2'-azobis (2-methylpropionamidine) dihydrochloride; VBPP, (4-vinylbenzyl)monophosphono-phosphate; VSME, vinyl sulfonate methyl ester; NaOMe, sodium methoxide; NaCl, sodium chloride; DMVP, dimethyl vinyl phosphonate A "monomer molecule" is defined by the International Union of Pure and Applied Chemistry (IUPAC) as "A molecule which can undergo polymerization thereby contributing constitutional units to the essential structure of a macromolecule." A polymer is a macromolecule.

A "polymer backbone" or "main chain" is defined by IUPAC as "That linear chain to which all other chains, long or short, or both may be regarded as being pendant" with the note that "Where two or more chains could equally be considered to be the main chain, that one is selected which leads the simplest representation of the molecule." Backbones can be of different chemical compositions depending upon the starting materials from which they are made. Common backbones from chemically and biologically synthesized polymers include alkanes, typically from vinyl or methyl vinyl polymerizations or cationic and anionic polymerizations, poly esters, from condensation polymerizations, poly amides, such as poly peptides from polymerizations involving amidation reactions, and poly ethoxylates from epoxide ring opening.

A "pendant group" or "side group" is defined by IUPAC as "An offshoot, neither oligomeric nor polymeric from a chain." A side group as such does not include a linear repeated unit.

A "polymer side chain" or "pendant chain" is defined by IUPAC as "An oligomeric or polymeric offshoot from a macromolecular chain" with the additional notes that "An oligomeric branch may be termed a short chain branch" and "A polymeric branch may be termed a long chain branch".

"Post-polymerization modification" is defined as any reaction or treatment of a polymer that takes place following polymerization. Post-polymerization modifications include reactions to chemical groups within or attached to the polymer backbone, pendant group, or polymer side chains.

'By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include oral care compositions, such as, dentifrice, mouth rinse, mousse, foam, mouth spray, lozenge, chewable tablet, chewing gum, tooth whitening strips, floss and floss coatings, breath freshening dissolvable strips, denture care product, denture adhesive product; after shave gels and creams, pre-shave preparations, shaving gels, creams, or foams, moisturizers and lotions; cough and cold compositions, gels, gel caps, and throat sprays; leave-on skin lotions and creams, shampoos, body washes, body rubs, such as Vicks Vaporub; hair conditioners, hair dyeing and bleaching compositions, mousses, shower gels, bar soaps, antiperspirants, deodorants, depilatories, lipsticks, foundations, mascara, sunless tanners and sunscreen lotions; feminine care compositions, such as lotions and lotion compositions directed towards absorbent articles; baby care compositions directed towards absorbent or disposable articles; and oral cleaning compositions for animals, such as dogs and cats.

The term "dentifrice", as used herein, includes tooth or subgingival—paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Herein, the terms "tartar" and "calculus" are used interchangeably and refer to mineralized dental plaque biofilms.

As used herein, the word "or" when used as a connector of two or more elements is meant to include the elements individually and in combination; for example X or Y, means X or Y or both.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Phosphono-Phosphate and Anionic Containing Polymers

The present invention is directed to a novel polymer comprising a phosphono-phosphate group and an anionic group. It is recognized that the phosphono-phosphate group can be anionic in nature depending upon the substituents upon it and the environment into which it is placed. For the purpose of clarity, anionic group in this application refers to an anionic group other than phosphono-phosphate.

In certain embodiments, the present invention is directed to a novel polymer comprising a phosphono-phosphate group and an anionic group wherein said phosphono-phosphate group has the structure of Formula 1:

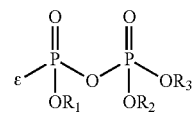

Formula 1 wherein:

ε is the site of attachment to a carbon atom in the polymer backbone, side group, or side chain;

$R_1$ is selected from the group consisting of —H, alkyl, alkanediyl-alkoxy, metal salt having Na, K, Ca, Mg, Mn, Zn, Fe, or Sn cation, amine cation salt, and a structure of Formula 2:

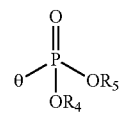

Formula 2 wherein:

θ is the site of attachment to Formula 1, $R_4$ and $R_5$ are independently selected from the group consisting of —H, alkyl, alkanediyl-alkoxy, metal salt having Na, K, Ca, Mg, Mn, Zn, Fe, or Sn cation, and amine cation salt;

$R_2$ is selected from the group consisting of —H, alkyl, alkanediyl-alkoxy, metal salt having Na, K, Ca, Mg, Mn, Zn, Fe, or Sn cation, amine cation salt, and a structure of Formula 3:

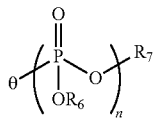

Formula 3 wherein:

θ is the site of attachment to Formula 1, $R_6$, and $R_7$ are independently selected from the group consisting of —H, alkyl, alkanediyl-alkoxy, metal salt having Na, K, Ca, Mg, Mn, Zn, Fe, or Sn cation, and amine cation salt, and n is an integer from 1 to 22; and $R_3$ is selected from the group consisting of —H, alkyl, alkanediyl-alkoxy, metal salt having Na, K, Ca, Mg, Mn, Zn, Fe, or Sn cation, and amine cation salt, and said anionic group is covalently bound to the polymer backbone, side group, or side chain and is selected from the chemical group consisting of phosphate, phosphonate, phosphinate, sulfate, sulfonate, sulfinate, mercapto, carboxylate, hydroxyamino, amine oxide, and hydroxamate.

In certain embodiments, at least one monomer used to create the polymer comprises the phosphono-phosphate group. In another embodiment, at least one monomer used to create the polymer comprises the anionic group. In another embodiment, at least one monomer used to create said polymer comprises said anionic group and at least one monomer used to create said polymer comprises said phosphono-phosphate group. In another embodiment, the phosphono-phosphate group is added during a post-polymerization modification.

In certain embodiments of the polymer, $R_1$, $R_2$, and $R_3$ are independently selected from the group consisting of H, Na salt, and K salt. In certain embodiments of the polymer, $R_1$, $R_2$, and $R_3$ are independently selected from the group consisting of H, Na salt, K salt, Zn salt, Ca salt, Sn salt, and amine cation salt.

In another embodiment of the polymer, $R_1$ has the structure of Formula 2. In a further embodiment of the polymer, $R_1$ has the structure of Formula 2 and $R_4$ and $R_5$ are independently selected from H, Na salt, and K salt. In a further embodiment of the polymer, $R_1$ has the structure of Formula 2 and $R_4$ and $R_5$ are independently selected from H, Na salt, K salt, Zn salt, Ca salt, Sn salt, and amine cation salt.

In another embodiment of the polymer, $R_2$ has the structure of Formula 3. In another embodiment of the polymer $R_2$ has the structure of Formula 3 and n is an integer from 1 to 3. In another embodiment of the polymer, $R_2$ has the structure of Formula 3 and n is 1. In another embodiment of the polymer, $R_2$ has the structure of Formula 3 and $R_6$ and $R_7$ are independently selected from the group consisting of H, Na salt, and K salt. In another embodiment of the polymer, $R_2$ has the structure of Formula 3 and $R_6$ and $R_7$ are independently selected from the group consisting of H, Na salt, K salt, Zn salt, Ca salt, Sn salt, and amine cation salt. In another embodiment of the compound, $R_2$ has the structure of Formula 3, $R_6$ and $R_7$ are independently selected from the group consisting of H, Na salt, K salt, Zn salt, Ca salt, Sn salt, and amine cation salt, and n is 1.

In certain embodiments, when at least one monomer used to create the polymer comprises the phosphono-phosphate group, said at least one monomer has the structure of Formula 4:

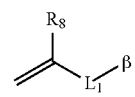

Formula 4 wherein:

β is the site of attachment to the phosphono-phosphate group of Formula 1;

$R_8$ is selected from the group consisting of —H and —CH$_3$;

$L_1$ is selected from the group consisting of a chemical bond, arenediyl, and a structure of Formula 5:

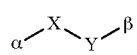

Formula 5 wherein:

α is the site of attachment to the alkenyl radical in Formula 4;

β is the site of attachment to the phosphono-phosphate group of Formula 1;

X is selected from the group consisting of the structures in Formulas 6-12;

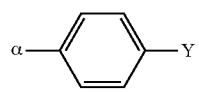

Formula 6

Formula 7

Formula 8

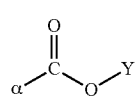

Formula 9

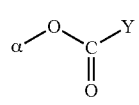

Formula 10

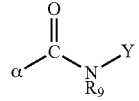

Formula 11

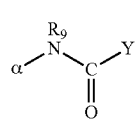

Formula 12 wherein:
R$_9$ is selected from the group consisting of —H, alkyl$_{(C1-8)}$, phosphonoalkyl, and phosphono(phosphate)alkyl; and
Y is selected from the group consisting of alkanediyl, alkoxydiyl, alkylaminodiyl and alkenediyl.

In certain embodiments, when at least one monomer used to create the polymer comprises the phosphono-phosphate group and has the structure of Formula 4, R$_8$ of Formula 4 is H. In certain embodiments, when at least one monomer used to create the polymer comprises the phosphono-phosphate group and has the structure of Formula 4, R$_8$ of Formula 4 is CH$_3$.

In certain embodiments, when at least one monomer used to create the polymer comprises the phosphono-phosphate group, and said at least one monomer has the structure of Formula 4, L$_1$ is a covalent bond. In another embodiment, when at least one monomer used to create the polymer comprises the phosphono-phosphate group, and said at least one monomer has the structure of Formula 4, L$_1$ has the structure of Formula 5. In another embodiment, when at least one monomer used to create the polymer comprises the phosphono-phosphate group, said at least one monomer has the structure of Formula 4, and L$_1$ has the structure of Formula 5, the structure of X is selected from the group consisting of Formula 6, Formula 9 and Formula 11. In another embodiment, when at least one monomer used to create the polymer comprises the phosphono-phosphate group, said at least one monomer has the structure of Formula 4, and L$_1$ has the structure of Formula 5, X has the structure of of Formula 6. In another embodiment, when at least one monomer used to create the polymer comprises the phosphono-phosphate group, said at least one monomer has the structure of Formula 4, and L$_1$ has the structure of Formula 5, X has the structure of of Formula 7. In another embodiment, when at least one monomer used to create the polymer comprises the phosphono-phosphate group, said at least one monomer has the structure of Formula 4, and L$_1$ has the structure of Formula 5, X has the structure of of Formula 9. In another embodiment, when at least one monomer used to create the polymer comprises the phosphono-phosphate group, said at least one monomer has the structure of Formula 4, and L$_1$ has the structure of Formula 5, X has the structure of of Formula 11. In another embodiment, when at least one monomer used to create the polymer comprises the phosphono-phosphate group, said at least one monomer has the structure of Formula 4, and L$_1$ has the structure of Formula 5, X has the structure of of Formula 6 and Y is alkanediyl. In another embodiment, when at least one monomer used to create the polymer comprises the phosphono-phosphate group, said at least one monomer has the structure of Formula 4, and L$_1$ has the structure of Formula 5, X has the structure of of Formula 7 and Y is selected from the group consisting of alkanediyl and alkoxydiyl. In another embodiment, when at least one monomer used to create the polymer comprises the phosphono-phosphate group, said at least one monomer has the structure of Formula 4, and L$_1$ has the structure of Formula 5, X has the structure of of Formula 9 and Y is alkanediyl. In another embodiment, when at least one monomer used to create the polymer comprises the phosphono-phosphate group, said at least one monomer has the structure of Formula 4, and L$_1$ has the structure of Formula 5, X has the structure of of Formula 11 and Y is alkanediyl.

In certain embodiments, said anionic group is selected from the group consisting of phosphate, phosphonate, sulfate, sulfonate or carboxylate. In another embodiment, said anionic group is sulfonate. In another said anionic group is carboxylate. In another embodiment, said anionic group is phosphonate.

In certain embodiments, when at least one monomer used to create the polymer comprises an anionic group, said at least one monomer further comprises an alkenyl group of the structure of Formula 13:

Formula 13 wherein:
R$_{10}$ is selected from the group consisting of H or CH$_3$ and
L$_2$ is a linking group to the anionic group.

In certain embodiments, when at least one monomer used to create the polymer comprises an anionic group and said at least one monomer further comprises an alkenyl group of the structure of Formula 13, R$_{10}$ is H. In another embodiment, when at least one monomer used to create the polymer comprises an anionic group and said at least one monomer further comprises an alkenyl group of the structure of Formula 13, R$_{10}$ is CH$_3$.

In certain embodiments, when at least one monomer used to create the polymer comprises an anionic group, said at least one monomer further comprises an alkenyl group of the structure of Formula 14:

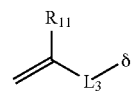

Formula 14 wherein:
R$_{11}$ is selected from the group consisting of H and alkyl;
δ is the site of attachment to the anionic group;
L$_3$ is selected from a chemical bond, arenediyl, and a structure of Formula 15;

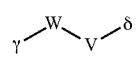

Formula 15 wherein:
γ is the site of attachment to the alkenyl radical;
δ is the site of attachment to the anionic group;
W is selected from the structures in Formulas 16-22:

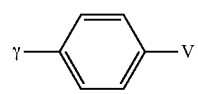

Formula 16

Formula 17

Formula 18

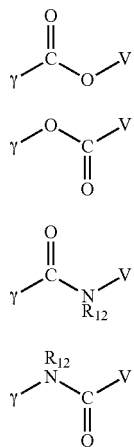

Formula 19

Formula 20

Formula 21

Formula 22 wherein:
$R_{12}$ is selected from the group consisting of —H and alkyl$_{(C1-8)}$; and
V is selected from the group consisting of alkanediyl, alkoxydiyl, alkylaminodiyl or alkenediyl.

In certain embodiments, when at least one monomer used to create the polymer comprises an anionic group and said at least one monomer further comprises an alkenyl group of the structure of Formula 14, $R_{11}$ is H. In another embodiment, when at least one monomer used to create the polymer comprises an anionic group and said at least one monomer further comprises an alkenyl group of the structure of Formula 14, $R_{11}$ is $CH_3$. In another embodiment, when at least one monomer used to create the polymer comprises an anionic group and said at least one monomer further comprises an alkenyl group of the structure of Formula 14, $L_3$ is a covalent bond. In another embodiment, when at least one monomer used to create the polymer comprises an anionic group and said at least one monomer further comprises an alkenyl group of the structure of Formula 14, $R_{11}$ is H and $L_3$ is a covalent bond. In another embodiment, when at least one monomer used to create the polymer comprises an anionic group and said at least one monomer further comprises an alkenyl group of the structure of Formula 14, $R_1$ is $CH_3$ and $L_3$ is a covalent bond.

In certain embodiments, when at least one monomer used to create the polymer comprises an anionic group and said at least one monomer further comprises an alkenyl group of the structure of Formula 14, $L_3$ has the structure of Formula 15 and W has the structure of Formula 16. In another embodiment, when at least one monomer used to create the polymer comprises an anionic group and said at least one monomer further comprises an alkenyl group of the structure of Formula 14, $L_3$ has the structure of Formula 15 and W has the structure of Formula 19. In another embodiment, when at least one monomer used to create the polymer comprises an anionic group and said at least one monomer further comprises an alkenyl group of the structure of Formula 14, $L_3$ has the structure of Formula 15 and W has the structure of Formula 21. In certain embodiments, when at least one monomer used to create the polymer comprises an anionic group and said at least one monomer further comprises an alkenyl group of the structure of Formula 14, $L_3$ has the structure of Formula 15 and W has the structure of Formula 16 and V is alkanediyl. In another embodiment, when at least one monomer used to create the polymer comprises an anionic group and said at least one monomer further comprises an alkenyl group of the structure of Formula 14, $L_3$ has the structure of Formula 15 and W has the structure of Formula 19 and V is alkanediyl. In another embodiment, when at least one monomer used to create the polymer comprises an anionic group and said at least one monomer further comprises an alkenyl group of the structure of Formula 14, $L_3$ has the structure of Formula 15 and W has the structure of Formula 21 and V is alkanediyl.

In certain embodiments, when at least one monomer used to create the polymer comprises an anionic group, said at least one monomer is selected from the group consisting of vinyl phosphonate, vinyl sulfonate, acrylate, methyl vinyl phosphonate, methyl vinyl sulfonate, methacrylate, styrene phosphonate, styrene sulfonate, vinyl benzene phosphonate, vinyl benzene sulfonate, 2-acrylamido-2-methyl propane sulfonate (AMPS), and 2-Sulfopropyl Acrylate (SPA).

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 99.9:0.1 to 0.1:99.9, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 99:1 to 1:99, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 90:10 to 10:90, respectively.

In certain embodiments, when at least one monomer used to create said polymer comprises said anionic group and at least one monomer used to create said polymer comprises said phosphono-phosphate group, the ratio of said at least one monomer comprising said phosphono-phosphate group to said at least one monomer comprising said anionic group ranges from 70:30 to 30:70, respectively.

Another embodiment of the present invention is an oral care composition comprising polymer which in this context is meant to include oligomers such as dimers trimers and tetramers. The polymer includes a phosphono-phosphate group and an anionic group with the structure of Formula 23:

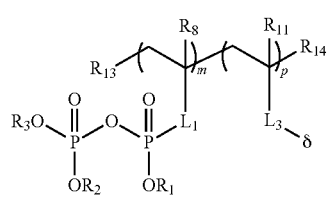

Formula 23 wherein:
$R_1$ is selected from the group consisting of —H, alkyl, alkanediyl-alkoxy, metal salt having Na, K, Ca, Mg, Mn, Zn, Fe, or Sn cation, amine cation salt, and a structure of Formula 2:

Formula 2

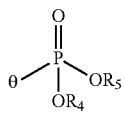

wherein:
θ is the site of attachment to Formula 23,
$R_4$ and $R_5$ are independently selected from the group consisting of —H, alkyl, alkanediyl-alkoxy, metal salt having Na, K, Ca, Mg, Mn, Zn, Fe, or Sn cation, and amine cation salt;
$R_2$ is selected from the group consisting of —H, alkyl, alkanediyl-alkoxy, metal salt having Na, K, Ca, Mg, Mn, Zn, Fe, or Sn cation, amine cation salt, and a structure of Formula 3:

Formula 3

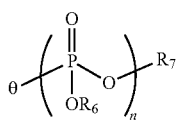

wherein:
θ is the site of attachment to Formula 23,
$R_6$, and $R_7$ are independently selected from the group consisting of —H, alkyl, alkanediyl-alkoxy, metal salt having Na, K, Ca, Mg, Mn, Zn, Fe, or Sn cation, and amine cation salt, and
n is an integer from 1 to 22; and
$R_3$ is selected from the group consisting of —H, alkyl, alkanediyl-alkoxy, metal salt having Na, K, Ca, Mg, Mn, Zn, Fe, or Sn cation, and amine cation salt, and said anionic group is covalently bound to the polymer backbone, side group, or side chain and is selected from the chemical group consisting of phosphate, phosphonate, phosphinate, sulfate, sulfonate, sulfinate, mercapto, carboxylate, hydroxyamino, amine oxide, and hydroxamate.
$R_8$ is selected from the group consisting of —H and —$CH_3$;
$L_1$ is selected from the group consisting of a chemical bond, arenediyl, and a structure of Formula 5:

Formula 5

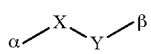

wherein:
α is the site of attachment to the polymer backbone;
β is the site of attachment to the phosphonophosphate;
X is selected from the group consisting of the structures in Formulas 6-12;

Formula 6

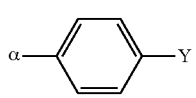

Formula 7

Formula 8

Formula 9

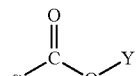

Formula 10

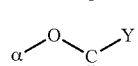

Formula 11

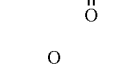

Formula 12

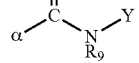

wherein:
$R_9$ is selected from the group consisting of —H, alkyl$_{(C1-8)}$, phosphonoalkyl, and phosphono(phosphate)alkyl; and
Y is selected from the group consisting of alkanediyl, alkoxydiyl, alkylaminodiyl and alkenediyl,
$R_{11}$ is selected from the group consisting of —H and —$CH_3$;
δ is the site of attachment to the anionic group;
$L_3$ is selected from a chemical bond, arenediyl, and a structure of Formula 15;

Formula 15

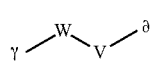

wherein:
γ is the site of attachment to the polymer backbone;
δ is the site of attachment to the anionic group;
W is selected from the structures in Formulas 16-22:

Formula 16

Formula 17

Formula 18

Formula 19

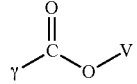

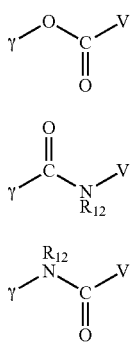

Formula 20

Formula 21

Formula 22 wherein:
R$_{12}$ is selected from the group consisting of —H and alkyl$_{(C1-8)}$; and
V is selected from the group consisting of alkanediyl, alkoxydiyl, alkylaminodiyl or alkenediyl;
R$_{13}$ is a chemical group resulting from polymer initiation;
R$_{14}$ is a chemical group resulting chain termination;
m is an integer from 2 to 450; and
p is an integer from 2 to 450.

In one embodiment of the polymer, R$_1$, R$_2$, and R$_3$ are independently selected from the group consisting of H, Na salt, and K salt. In one embodiment of the polymer, R$_1$, R$_2$, and R$_3$ are independently selected from the group consisting of H, Na salt, K salt, Zn salt, Ca salt, Sn salt, and amine cation salt.

In another embodiment of the polymer, R$_1$ has the structure of Formula 2. In a further embodiment of the polymer, R$_1$ has the structure of Formula 2 and R$_4$ and R$_5$ are independently selected from the group consisting of H, Na salt, and K salt. In a further embodiment of the polymer, R$_1$ has the structure of Formula 2 and R$_4$ and R$_5$ are independently selected from the group consisting of —H, Na salt, K salt, Zn salt, Ca salt, Sn salt, and amine cation salt.

In another embodiment of the polymer, R$_2$ has the structure of Formula 3. In another embodiment of the polymer R$_2$ has the structure of Formula 3 and n is an integer from 1 to 3. In another embodiment of the polymer, R$_2$ has the structure of Formula 3 and n is 1. In another embodiment of the polymer, R$_2$ has the structure of Formula 3 and R$_6$ and R$_7$ are independently selected from the group consisting of H, Na salt, and K salt. In another embodiment of the polymer, R$_2$ has the structure of Formula 3 and R$_6$ and R$_7$ are independently selected from the group consisting of H, Na salt, K salt, Zn salt, Ca salt, Sn salt, and amine cation salt. In another embodiment of the compound, R$_2$ has the structure of Formula 3, R$_6$ and R$_7$ are independently selected from the group consisting of H, Na salt, K salt, Zn salt, Ca salt, Sn salt, and amine cation salt, and n is 1.

In one embodiment of the polymer, R$_8$ is H. In another embodiment, R$_8$ is CH$_3$.

In one embodiment of the polymer, L$_1$ is a covalent bond. In another embodiment, L$_1$ has the structure of Formula 5. In another embodiment L$_1$ has the structure of Formula 5, the structure of X is selected from the group consisting of Formula 6, Formula 9 and Formula 11. In another embodiment, L$_1$ has the structure of Formula 5, X has the structure of Formula 6. In another embodiment, L$_1$ has the structure of Formula 5, X has the structure of Formula 7. In another embodiment, L$_1$ has the structure of Formula 5, X has the structure of Formula 9. In another embodiment, L$_1$ has the structure of Formula 5, X has the structure of Formula 11. In another embodiment, L$_1$ has the structure of Formula 5, X has the structure of Formula 6 and Y is alkanediyl. In another embodiment, L$_1$ has the structure of Formula 5, X has the structure of Formula 7 and Y is selected from the group consisting of alkanediyl and alkoxydiyl. In another embodiment, L$_1$ has the structure of Formula 5, X has the structure of of Formula 9 and Y is alkanediyl. In another embodiment, L$_1$ has the structure of Formula 5, X has the structure of Formula 11 and Y is alkanediyl.

In one embodiment of the polymer, said anionic group is selected from the group consisting of phosphate, phosphonate, sulfate, sulfonate or carboxylate. In another embodiment, said anionic group is sulfonate. In another embodiment, said anionic group is carboxylate. In another embodiment, said anionic group is phosphonate.

In one embodiment of the polymer, R$_{11}$ is H. In another embodiment, R$_{11}$ is CH$_3$. In another embodiment, L$_3$ is a covalent bond. In another embodiment, R$_{11}$ is H and L$_3$ is a covalent bond. In another embodiment, Ru is CH$_3$ and L$_3$ is a covalent bond.

In one embodiment, L$_3$ has the structure of Formula 15 and W has the structure of Formula 16. In another embodiment, L$_3$ has the structure of Formula 15 and W has the structure of Formula 19. In another embodiment, L$_3$ has the structure of Formula 15 and W has the structure of Formula 21. In one embodiment, L$_3$ has the structure of Formula 15 and W has the structure of Formula 16 and V is alkanediyl. In another embodiment, L$_3$ has the structure of Formula 15 and W has the structure of Formula 19 and V is alkanediyl. In another embodiment, L$_3$ has the structure of Formula 15 and W has the structure of Formula 21 and V is alkanediyl.

In one embodiment of the polymer, R$_{13}$, the chemical group resulting from polymer initiation, is selected from the structures of Formula 24-28:

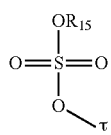

Formula 24

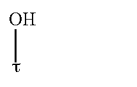

Formula 25

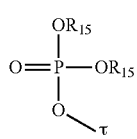

Formula 26

Formula 27

Formula 28

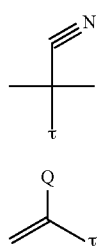

wherein:
R$_{15}$ is selected from the group consisting of —H, Na, K and amine cation salt;

τ is the site of attachment to polymer backbone and;
Q is the non-olefin residue of a monomer used in polymerization.

In a further embodiment, Q has the structure of Formula 29:

Formula 29

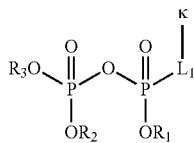

wherein: $L_1$, $R_1$, $R_2$ and $R_3$ are as previously noted and κ denotes the site of attachment to Formula 28.

In a further embodiment of the polymer, Q has the structure of Formula 30:

Formula 30

wherein: $L_3$, and δ are as previously noted and κ denotes the site of attachment to Formula 28.

In a further embodiment, Q is phosphono-phosphate. In a further embodiment Q is sulfonate. In a further embodiment Q is phosphonate.

In one embodiment of the polymer, $R_{14}$, the chemical group resulting from polymer termination, is selected from the group consisting of —H. In one embodiment of the compound, $R_{14}$, the chemical group resulting from polymer termination, is another polymer chain with a head to head attachment.

In one preferred embodiment of the polymer, $R_1$, $R_2$, and $R_3$ are independently selected from the group consisting of H, Na salt, K salt and amine cation salt, $R_8$ is H, $L_1$ is a covalent bond, $L_3$ is a covalent bond, the anionic group is sulfonate, $R_{13}$ is the structure of Formula 28, Q is the structure of Formula 29 or Formula 30 and $R_{14}$ is H.

Methods of Making the Polymers

Embodiments of the present invention can be made using these general following methods. The polymers of the present invention can be made by a wide variety of techniques, including bulk, solution, emulsion, or suspension polymerization. Polymerization methods and techniques for polymerization are described generally in Encyclopedia of Polymer Science and Technology, Interscience Publishers (New York), Vol. 7, pp. 361-431 (1967), and Kirk-Othmer Encyclopedia of Chemical Technology, 3rd edition, Vol 18, pp. 740-744, John Wiley & Sons (New York), 1982, both incorporated by reference herein. See also Sorenson, W. P. and Campbell, T. W., Preparative Methods of Polymer Chemistry. 2nd edition, Interscience Publishers (New York), 1968, pp. 248-251, incorporated by reference herein, for general reaction techniques suitable for the present invention. In one example, the polymers are made by free radical copolymerization, using water soluble initiators. Suitable free radical initiators include, but are not limited to, thermal initiators, redox couples, and photochemical initiators. Redox and photochemical initiators may be used for polymerization processes initiated at temperatures below about 30° C. Such initiators are described generally in Kirk-Othmer Encyclopedia of Chemical Technology, 3rd edition, John Wiley & Sons (New York), Vol. 13, pp. 355-373 (1981), incorporated by reference herein. Typical water soluble initiators that can provide radicals at 30° C. or below include redox couples, such as potassium persulfate/silver nitrate, and ascorbic acid/hydrogen peroxide. In one example, the method utilizes thermal initiators in polymerization processes conducted above 40° C. Water soluble initiators that can provide radicals at 40° C. or higher can be used. These include, but are not limited to, hydrogen peroxide, ammonium persulfate, and 2,2'-azobis(2-amidinopropane) dihydrochloride. In one example, water soluble starting monomers are polymerized in a water at 60° C. using ammonium persulfate as the initiator.

The identity of chemical functional groups at the terminal ends of a linear polymer depend upon how the polymerization of that polymer chain was initiated and terminated. For free radical polymerization, any free radical in the system can begin a new chain. This free radical can be a direct derivative of the initiator such as a sulfate radical from persulfate, or alkyl radical from the azo type initiators (such as but not limited to 2,2'azobis(2-amidinopropane) dihydrochloride). The free radical can also be the result of a transfer reaction, for instance between a water and another radical to produce a hydroxyl radical or between a phosphate and another radical to produce a phosphate radical. Non-limiting examples of these resulting structures are given below, where R represents an H or appropriate counter ion such as Na, K or an amine and T represents the site of attachment to the polymer.

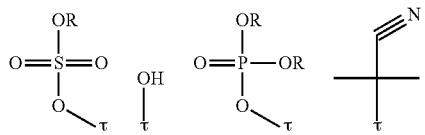

The free radical can also be the result of a chain transfer reaction, where the radical is transferred from a growing polymer chain to start a new chain. Chain transfer has been explicitly noted in polymerization of vinyl phosphonate monomers. Bingöl et al. Macromolecules 2008, 41, 1634-1639), incorporated by reference herein, describe how polymerization of alkyl esters of vinyl phosphonate result in chain transfer on the alkyl group. This transfer ultimately begins a new polymer chain with an olefin containing chemical group on the initiating end. A similar phenomenon appears to happen with vinyl phosphono-phosphate based polymerizations. A chain transfer stops growth of one chain and begins a new chain.

In the phosphono-phosphate containing polymers, vinyl $CH_2$ groups were observed in the final polymers compositions. These vinyl groups are hypothesized to form from one of two mechanisms. The first mechanism is a similar phenomenon to that observed by Bingöl, unlike Bingöl, however, the olefin is not from the alkyl ester of phoshonate, but potentially from the vinyl monomer on the newly initiated chain. Not wanting to be bound by theory, the below scheme is given as a possible route by which chain transfer could result in an olefin at the site of initiation for a generic free radical polymerizable monomer where the non-olefin portion of the monomer is simply depicted as Q for clarity. Q can represent any number of chemical functional groups and is not limited to a single chemical entity. Olefin terminated groups based on vinyl phosphonate and vinyl phosphono-phosphate have been observed.

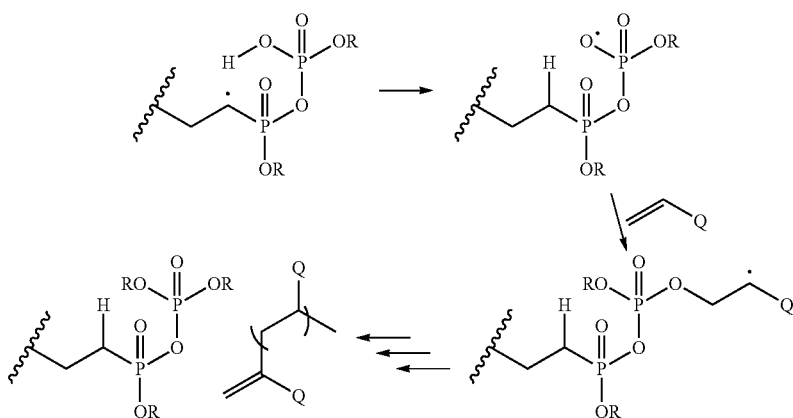

The second mechanism to introduce vinyl groups involves a backbiting reaction and beta scission. This mechanism has been extensively noted for acrylate polymers in the literature. A vinyl group and primary radical result after beta scission.

disproportionation. In chain transfer and backbiting, the terminating group is typically a hydrogen. In combination, the propagating radicals on two chains react to form a new chain. This reaction causes a "head to head" configuration at the point of attachment.

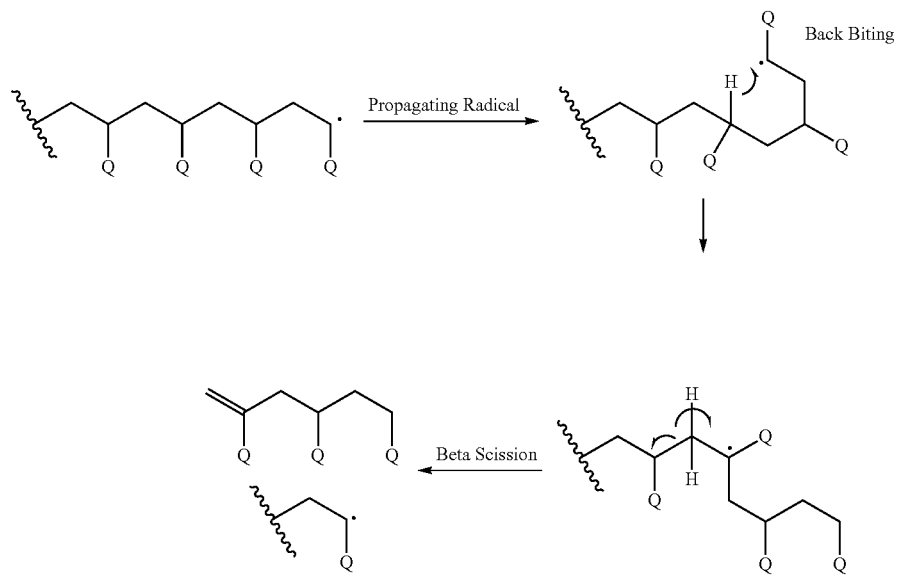

Using the previously used nomenclature of using T to represent the site of attachment to the polymer, the initial functional group can be written as follows. It should be noted that both the chain transfer and backbiting followed by beta scission mechanisms will produce a vinyl group with two protons on the same carbon atom.

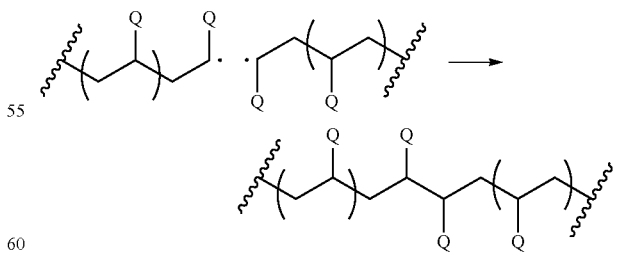

The chemical group on the terminating end of the polymer chain depends upon how the chain is terminated. The most common terminations are the previously mentioned chain transfer, and backbiting reactions as well as combination and disproportionation.

In disproportionation, a hydrogen is exchanged from one radical chain to another radical chain. The result is one chain is unsaturated while the other is saturated. Of note, the resulting unsaturated group is not a vinyl group. Each carbon in the unsaturation has only one hydrogen.

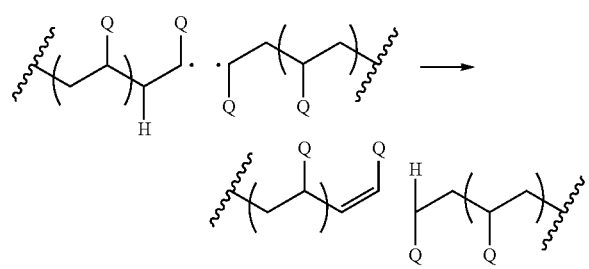

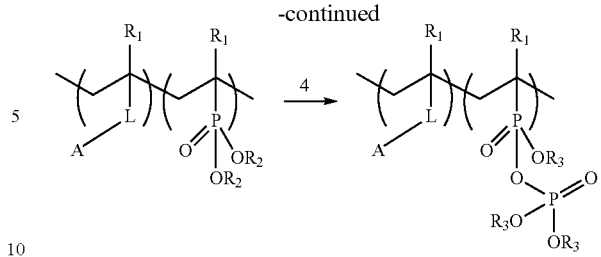

$R_1$ = H, $CH_3$
$R_2$ = H, Alkyl, Salts
$R_3$ = H, Salts, $P(O)(OR_3)_2$
L = Linking Group
A = Anionic Group A polymer comprising a phosphono-phosphate group and anionic group can have the phosphono-phosphate and anionic groups attached directly off the polymer backbone, on a side group, or on a side chain. This phosphono-phosphate group can be incorporated into the polymer by either polymerization of monomers having the phosphono-phosphate group, or by polymerization of monomers without a phosphono-phosphate group and subsequent post-polymerization modification of the resulting polymer to add the phosphono-phosphate group. Similarly, the anionic group can be incorporated into the polymer by either polymerization of monomers having the anionic group, or by polymerization of monomers without an anionic group and subsequent post-polymerization modification of the resulting polymer to add the anionic group. The examples in the subsequent paragraphs will depict different methods of incorporating phosphono-phosphate groups onto polymers with the anionic group either introduced as a co-monomer or as a result of incomplete reaction of a phosphonate when attempting to form a phosphono-phosphate group. This section will not depict all possible anionic monomers, nor will it depict the various methods of introducing anionic groups onto a polymer after polymerization, since they are well known to those skilled in the art.

As examples of polymers comprising a phosphono-phosphate group attached to a polymer backbone, consider the polymers made from the monomers vinyl phosphonate or methyl-vinyl phosphonate. Vinyl phosphonate or methyl-vinyl phosphonate can be chemically reacted to form phosphono-phosphate monomers as shown in reaction 1 in Scheme 1. These phosphono-phosphate containing monomers can then be co-polymerized with a monomer containing an anionic group as shown in reaction 2 of the same scheme to yield a phosphono-phosphate containing polymer with the phosphono-phosphate group attached directly to the polymer backbone. Alternatively, vinyl phosphonate or methyl-vinyl phosphonate can be first co-polymerized as shown in reaction 3 to yield a polymer. After polymerization, the phosphono-phosphate group can be created by post-polymerization modification by reacting the attached phosphonate moiety as shown in reaction 4 thus creating a phosphono-phosphate group attached directly to the polymer backbone.

A second manner of creating a phosphono-phosphate group and anionic group attached directly to the backbone by a post polymerization modification can be exemplified by starting with polyethylene. For an example of the first reaction in such a modification, see M. Anbar, G. A. St. John and A. C Scott, J Dent Res Vol 53, No 4, pp 867-878, 1974. As shown in Scheme 2, polyethylene is first phosphorylated oxidatively with oxygen and $PCl_3$ to form a randomly phosphonated polymer. This phosphonated polymer can then be modified to produce a randomly substituted phosphono-phosphate/phosphonate polymer. The reaction products shown are meant to show the random nature of the points of attachment of the phosphonate and phosphono-phosphate groups of the resulting polymer. Phosphonate groups are anionic.

Scheme 2

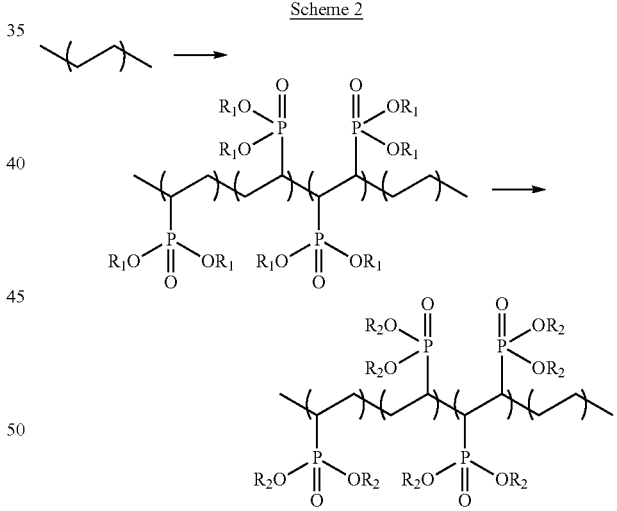

$R_1$ = H, Salts
$R_2$ = H, Salts, $P(O)(OR_2)_2$

As an example of the production of polymers having a phosphono-phosphate group attached to a side group, consider the vinyl benzyl chemistry depicted in Scheme 3. 4-Vinylbenzyl chloride can be reacted with diethyl phosphite to form vinyl benzyl phosphonate depicted in reaction 1 of Scheme 3. For an example of this reaction, see Frantz, Richard; Durand, Jean-Olivier; Carre, Francis; Lanneau, Gerard F.; Le Bideau, Jean; Alonso, Bruno; Massiot, Dominique, Chemistry—A European Journal, Volume 9, Issue 3, pp. 770-775, 2003. Vinyl benzyl phosphonate can be reacted to form vinyl benzyl phosphono-phosphate shown in reac- Scheme 1

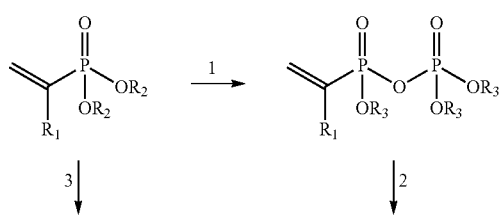

tion 2, as described in the example section below. This monomer can then be co-polymerized, to form a phosphono-phosphate and anionic containing polymer depicted by reaction 5, in which the phosphono-phosphate group is attached to a side group on the polymer. Alternatively, the first intermediate, vinyl benzyl phosphonate, can be polymerized shown in reaction 4 to make a polymer with vinyl benzyl phosphonate. For an example of this reaction, see M. Anbar, G. A. St. John and A. C Scott, J Dent Res Vol 53, No 4, pp 867-878, 1974. The polymer with vinyl benzyl phosphonate can then be reacted as shown in reaction 7 to produce a phosphono-phosphate and anionic containing polymer where the phosphono-phosphate group is attached to a side group on the polymer by a post polymerization modification. A second route involving a post polymerization modification is also shown in the same scheme. 4-Vinylbenzyl chloride can be co-polymerized to provide a polymer with vinyl benzyl chloride shown in reaction 3. This polymer can be phosphonated shown in reaction 6 (for example, see Sang Hun Kim, Young Chul Park, Gui Hyun Jung, and Chang Gi Cho, Macromolecular Research Vol 15 No 6 pp 587-597, 2007), and then the resulting polymer vinyl benzyl phosphonate reacted to produce the phosphono-phosphate and anionic containing polymer shown in reaction 7.

As a first example of polymers comprising a phosphono-phosphate group attached to a side chain, consider the poly ethylene glycol (PEG) side chains depicted in Scheme 4. A phosphonate containing PEG chain can be reacted with acryl chloride to produce an acrylic ester with an PEG terminated phosphonate. After reaction to produce a phosphono-phosphate, the phosphono-phosphate monomer can be co-polymerized with an anionic containing monomer to produce a phosphono-phosphate and anionic containing polymer where the phosphono-phosphate is attached to a side chain of the polymer.

Scheme 4

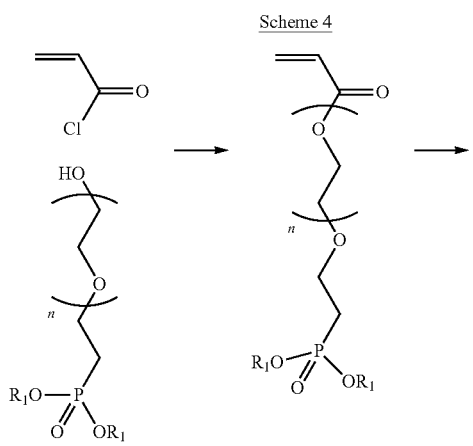

Scheme 3

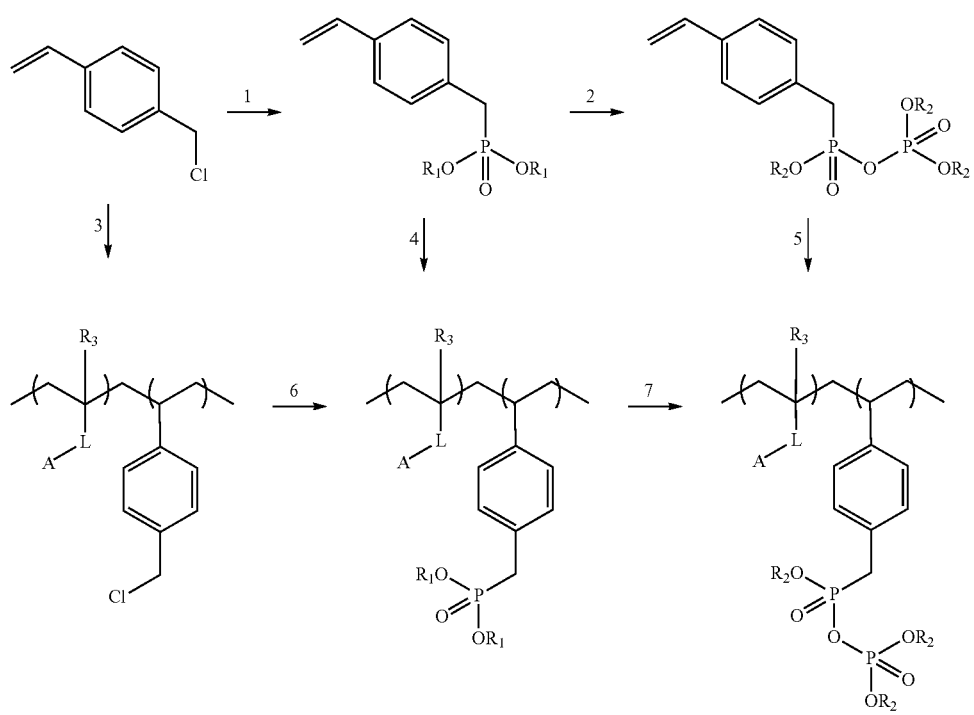

$R_1$ = H, Salts, Alkyl
$R_2$ = H, Salts, P(O)OR$_2$)$_2$
$R_3$ = H, CH$_3$
L = Linking Group
A = Anionic Group -continued

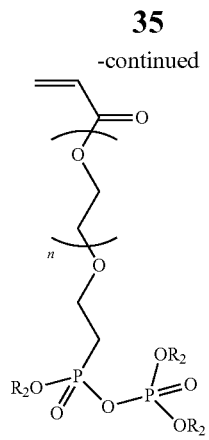

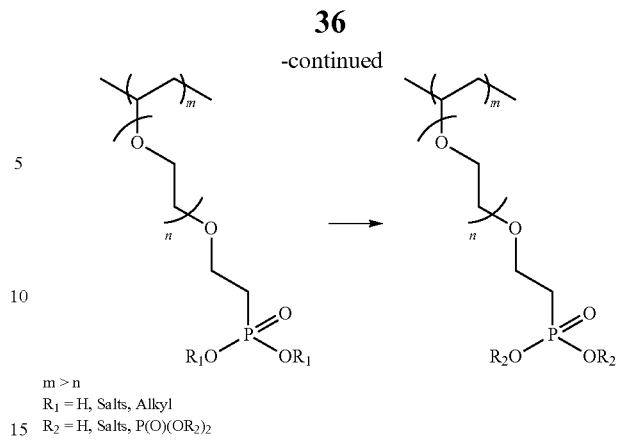

m > n
$R_1$ = H, Salts, Alkyl
$R_2$ = H, Salts, P(O)(OR$_2$)$_2$

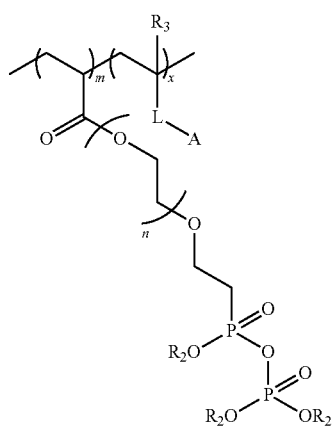

m + x > n
$R_1$ = H, Salts, Alkyl
$R_2$ = H, Salts, P(O)(OR$_2$)$_2$
$R_3$ = H, CH$_3$
L = Linking Group
A = Anionic Group As a second example of polymers comprising a phosphono-phosphate group attached to a side chain, consider the poly vinyl alcohol depicted in Scheme 5. The hydroxyl groups can be reacted with ethylene oxide to produce a polymer with PEG side chains. The terminating hydroxy on the side chains can be reacted with vinyl phosphonate, and then partially reacted to form a phosphono-phosphate/phosphonate polymer. This example thus depicts a phosphono-phosphate containing polymer where the phosphono-phosphate is attached to a side chain of the polymer and is added via a post polymerization modification. Phosphonate is an anionic group.

Scheme 5

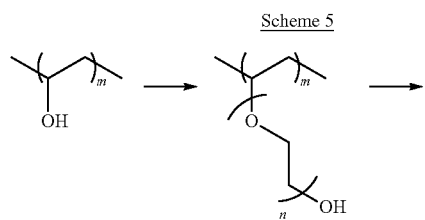

The schemes depicted are not meant to be exhaustive in nature, but are meant to convey the various manners in which phosphono-phosphate and anionic containing polymers may be produced. The examples provide both technical details for synthesis and numerous variations of polymers containing phosphono-phosphate and anionic groups, including polymers with phosphono-phosphate groups attached directly to the polymer backbone and polymers with phosphono-phosphate groups attached to side groups. For further examples of phosphonate containing monomers and polymers that can be transformed into phosphono-phosphonate containing monomers and polymers, see Sophie Monge, Benjamin Canniccioni, Ghislain David and Jean-Jacques Robin, RSC Polymer Chemistry Series No. 11, Phosphorus-Based Polymers: From Synthesis to Applications, Edited by Sophie Monge and Ghislain David, The Royal Society of Chemistry 2014, Published by the Royal Society of Chemistry, www.rsc.org.

Uses of the Phosphono-Phosphate Containing Polymers

The phosphono-phosphate containing polymers according to the present invention can be incorporated into a variety of compositions. These compositions include both aqueous and non-aqueous compositions. The compositions are useful for treating teeth, hair, body, fabric, paper, nonwovens and hard surfaces. The compositions find utility in water treatments, boiler treatments, treating ship hulls, oil wells, batteries, baking, leavening, ceramics, plastics stabilizers, glass manufacture, cheese production, buffers in food, abrasives in dentifrice, binders in meat, coffee creamers, antifreeze, dispersing agents in paints liquid soaps, metal cleaners synthetic rubber, textiles and flame retardants. The compositions are also useful for treating materials containing multivalent metal cations including but not limited to calcium, tin, magnesium and iron. Examples of such materials include hydroxyapatite, calcium carbonate (amorphous, calcite, aragonite), calcium phosphate, calcium hydroxide, magnesium carbonate, magnesium phosphate, soap scum (mixture of calcium, magnesium, and iron salts of stearic acid and carbonate), and hard water stains. In certain embodiments, the composition comprising phosphono-phosphate containing polymers is non-aqueous. In another embodiment, the composition is aqueous.

The phosphono-phosphate containing compounds and polymers can be applied to a variety of substrates. Embodiments of substrates include biological material, fabric, nonwoven materials, paper products and hard surface materials. In certain embodiments, the biological material comprises teeth. In another embodiment, the biological material comprises keratin, such as hair or skin.

Oral Care Compositions

The present invention further relates to oral care compositions comprising the polymers of the present invention comprising a phosphono-phosphate group and anionic group. The oral care compositions of the present invention can further comprise additional ingredients such as polymeric mineral surface agent agents, metal ion salts, water, humectants, fluoride source, buffering agents, anticalculus agents, abrasive polishing materials, thickening agents, surfactants, titanium dioxide, colorants, flavorants, antimicrobial agents, and mixtures thereof.

A preferred polymeric mineral surface active agent is a polyphosphate. A polyphosphate is generally understood to consist of two or more phosphate molecules arranged primarily in a linear configuration, although some cyclic derivatives may be present. Although pyrophosphates are technically polyphosphates, the polyphosphates desired are those having around three or more phosphate molecules so that surface adsorption at effective concentrations produces sufficient non-bound phosphate functions, which enhance the anionic surface charge as well as hydrophilic character of the surfaces. The pyrophosphates are discussed separately under additional anticalculus agents. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 3 to about 125. Preferred polyphosphates are those having n averaging from about 6 to about 21, such as those manufactured by FMC Corporation and commercially known as Sodaphos (n≈6), Hexaphos (n≈13), and Glass H (n≈21). A particularly preferred polyphosphate has n averaging about 21 such as Glass H. These polyphosphates may be used alone or in a combination thereof.

Oral compositions which comprise polyphosphates are disclosed in e.g., U.S. Pat. Nos. 5,939,052, 6,190,644, 6,187,295, and 6,350,436, all assigned to The Procter & Gamble Co. In these compositions, the polyphosphates are disclosed to provide benefits including tartar inhibition and reducing aesthetic negatives such as astringency and staining caused by other actives such as stannous. The use of polyphosphates for the prevention of dental erosion is not disclosed. The polyphosphate sources are also described in more detail in Kirk-Othmer Encyclopedia of Chemical Technology, Fourth Edition, Volume 18, Wiley-Interscience Publishers (1996). An effective amount of a polymeric mineral surface active agent will typically be from about 1% to about 35%, preferably from about 2% to about 30%, more preferably from about 5% to about 25%, and most preferably from about 6% to about 20%, by weight of the total oral composition.

The metal ions suitable for use in the present invention have strong affinity for enamel surface and include stannous, copper and zinc ions. These ions provide surface protection effects by reacting with tooth surface ions and/or other components of the composition to produce highly insoluble compounds on the surface. Additionally, these metal ions undergo oxidation and hydrolysis under salivary pH conditions and produce insoluble deposits on tooth surfaces. The present compositions may comprise a metal ion source that provides stannous ions, zinc ions, copper ions, or mixtures thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper. Preferred are stannous salts, such as stannous fluoride or stannous chloride.

Stannous, zinc and copper ions have been found to help in the reduction of gingivitis, plaque, sensitivity, and improved breath benefits. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al.

The combined metal ion source(s) will be present in an amount of from about 0.1% to about 11%, by weight of the final composition. Preferably, the metal ion sources are present in an amount of from about 0.5 to about 7%, more preferably from about 1% to about 5%. Preferably, the stannous salts may be present in an amount of from about 0.1 to about 7%, more preferably from about 1% to about 5%, and most preferably from about 1.5% to about 3% by weight of the total composition.

In preparing the present compositions, it is desirable to water and/or humectants to the compositions. Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water will generally comprise from about 5% to about 70%, and preferably from about 10% to about 50%, by weight of the composition herein. Generally, the level of water is up to about 50%, preferably from about 5% to about 30%, and more preferably from about 10% to about 25%, by weight of the oral composition. The amounts of water include the free water which is added plus that which is introduced with other materials, such as with sorbitol, silica, surfactant solutions, and/or color solutions.

The oral composition of the present invention may incorporate a soluble fluoride source capable of providing free fluoride ions. The fluoride ion source may preferably be in a separate phase than the polymeric surface active agent to aid in stability. Preferred soluble fluoride ion sources include sodium fluoride, stannous fluoride, indium fluoride, amine fluoride and sodium monofluorophosphate. Sodium fluoride and stannous fluoride the most preferred soluble fluoride ion source. Stannous fluoride and methods of stabilization are described in U.S. Pat. No. 5,004,597 issued to Majeti et al. and in U.S. Pat. No. 5,578,293 issued to Prencipe et al., in addition to other sources Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The present compositions may contain a buffering agent. Buffering agents, as used herein, refer to agents that can be used to adjust the pH of the compositions to a range of about pH 4 to about pH 10. The oral composition containing a polymeric mineral surface active agent will typically have a slurry pH of from about 4 to about 10, preferably from about 4.5 to about 8, and more preferably from about 5.5 to about 7. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Pyrophosphate salts may be used in the present invention as anticalculus agents. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. The pyrophosphate salts are described in more detail in Kirk-Othmer Encyclopedia of Chemical Technology, Third Edition, Volume 17, Wiley-Interscience Publishers (1982).

An abrasive polishing material may also be included in the oral compositions. The abrasive polishing material contemplated for use in the compositions of the present invention can be any material which does not excessively abrade dentin. The abrasive polishing material should be formulated in the oral composition so that it does not compromise the stability of any ingredients, such as stannous fluoride. Typical abrasive polishing materials include silica gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used. Silica dental abrasives of various types are preferred because of their unique benefits of exceptional dental cleaning and polishing performance without unduly abrading tooth enamel or dentine. The abrasive in the toothpaste compositions described herein is generally present at a level of from about 6% to about 70% by weight of the composition. Preferably, toothpastes contain from about 10% to about 50% of abrasive, by weight of the dentifrice composition.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

The present invention provides compositions in the form of toothpastes, dentifrices, tooth powder, topical oral gels, mouthrinses, denture product, mouthsprays, lozenges, oral tablets, and chewing gums. Typically these compositions will contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, xylitol, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include other agents, such as antimicrobial agents. These agents may be present at levels of from about 0.01% to about 1.5%, by weight of the dentifrice composition.

The oral compositions of the present invention are in the form of toothpastes, dentifrices, topical oral gels, mouthrinses, denture products, mouthsprays, lozenges, oral tablets, or chewing gums. The dentifrice compositions may be a paste, gel, or any configuration or combination thereof.

EXAMPLES

The following examples further describe and demonstrate the preferred embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

Powder Stain Prevention Model (PSPM)

The Powder Stain Prevention Model (PSPM) is a screening technique where hydroxyapatite powder (HAP) is used as a substrate for stain accumulation. The general purpose of this technique is to illustrate and quantify the stain prevention ability or staining potential of chemical agents used in oral care. Hydroxyapatite powder provides a large surface area to which tea chromogens adsorb. Pretreatment of HAP with oral care actives, either in rinse or dentifrice form, results in different levels of stain accumulation depending upon the ability of the actives to block or enhance the binding of these chromogens onto HAP surface. The magnitude of stain can then be quantified by image analysis. Steps involved in PSPM are described below.

1. HAP Pretreatment

Measure 200 mg-210 mg of HAP powder (BioGel® HTP-Gel Catalog #130-0421, Bio-Rad Laboratories (Hercules, Calif.) into 50 ml centrifuge tubes. Add 20 ml of treatment to each tube. For simple polymer the treatment is a 2 wt % of polymer or control at 100% active basis is used. For dentifrice formulations, weigh 8 g of each of the toothpaste into labeled 50 g round bottom centrifuge tubes. Add 24 g of deionized water into the tubes (so that the slurry ratio is 1:3). Vortex for 1 min to mix well to prepare the slurry with no chunks of toothpaste. Centrifuge the slurry for 15 min at 15,000 rpm using the centrifuge and use 20 mL of supernantent as the treatment. Tube is vortexed for 30 seconds to fully suspend HAP in treatment followed by centrifugation at 15,000 rpm for 15 mins. After centrifugation, supernatant is decanted and pellet redistributed by adding 25 ml of water, vortexing, centrifuging at 15,000 rpm for 15 mins, and decanting—making sure pellet breaks up during vortexing. The wash cycle is repeated two more times.

2. HAP Staining

After final water wash, 20 ml of filtered tea (1 Lipton tea bag per 100 ml of hot water seeped for 5 minutes, filtered and used at 50° C.) is added to each pellet and vortexed for 30 seconds to fully suspend HAP in tea. Powder suspension is centrifuged at 15,000 rpm for 15 mins and decanted. About 25 ml of water is added to the tube, vortexed and then centrifuging at 15,000 rpm for 15 mins. The liquid is decanted and wash cycle is repeated 2 more times.

3. HAP Prep for Color Analysis

Vortex pellet in approximately 10 ml of water until fully suspended followed by filtering under vacuum onto a Millipore filter disk (Membrane Filters 4.5 tm, 47 mm Catalog #HAWPO4700, Millipore Corporation, Bedford, Mass.). Prepare a control disk using. –200 mg of untreated, unstained HAP. Filter disks are then dried overnight in flat position and then laminated.

4. Color Analysis of Stained HAP

Whitelight system: HAP disk (untreated HAP control and HAP treatments) is placed in a stabilized sample holder. The color is measured using a digital camera having a lens equipped with a polarizer filter (Camera model no. CANON EOS 70D from Canon Inc., Melville, N.Y. with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle such that the light paths meet on the HAP disk. Image analysis is performed using Whitelight with Ultragrab, Optimas and Giant Imaging software.

5. Controls

Usual controls for a single polymer PSPM are water as a treatment followed by exposure to tea, and water without exposure to tea. Additionally, pyrophosphate and polyphosphate are run as internal controls.

6. Results

Calculate changes in L*(brightness), a*(red(+)/green(–)), b*(yellow (–)/blue(+)), and in E (total color) as follows:

$$\Delta L = L^*_{untreated\ HAP} - L^*_{treated\ HAP}$$

$$\Delta a = a^*_{untreated\ HAP} - a^*_{treated\ HAP}$$

$$\Delta b = b^*_{untreated\ HAP} - b^*_{treated\ HAP}$$

$$\Delta E = \sqrt{(\Delta L)^2 + (\Delta a)^2 + (\Delta b)^2}$$

Report results as average ΔL, Δa, Δb, and/or ΔE and percent prevention of stain (AL & AE) versus the negative control.

Powder Stain Removal Model (PSRM)

The Powder Stain Removal Model (PSRM) is a screening technique where hydroxyapatite powder (HAP) is used as a substrate for stain accumulation. The purpose of this technique is to illustrate and quantify the stain removal properties of chemical agents used in oral care. Hydroxyapatite powder provides a large surface area to which tea chromogens adsorb. Treatment of stained HAP with oral care actives, either in rinse or dentifrice form, results in different levels of stain removal depending upon the ability of the actives to disrupt the binding of these chromogens onto HAP surface. The magnitude of stain removal can then be quantified by image analysis. A trial of this model can be completed in three days. Steps involved in PSRM are described below.

1. HAP Staining

Prepare large batch of tea stain HAP by stirring 10 g of HAP powder in 200 ml of filtered tea for 5 minutes. Divide into centrifuge tubes and centrifuge at 15,000 rpm for 15 mins. Wash pellet by adding in 25 ml of water, vortexing, centrifuging at 15,000 rpm for 15 mins, and pipet out liquid. Make sure pellet breaks up during vortexing. Repeat wash.

Place centrifuge tubes in convection oven (55-65° C.) overnight to dry stained HAP. Once dried, pool stained HAP together and grind to a fine powder with pestle and mortar.

2. HAP Treatment

Measure 200 mg-210 mg of HAP powder (BioGel® HTP-Gel Catalog #130-0421, Bio-Rad Laboratories (Hercules, Calif.) into 50 ml centrifuge tubes. Add 20 ml of treatment to each tube. For simple polymer the treatment is a 2 wt % of polymer or control at 100% active basis is used. For dentifrice formulations, weigh 8 g of each of the toothpaste into labeled 50 g round bottom centrifuge tubes. Add 24 g of deionized water into the tubes (so that the slurry ratio is 1:3). Vortex for 1 min to mix well to prepare the slurry with no chunks of toothpaste. Centrifuge the slurry for 15 min at 15,000 rpm using the centrifuge and use 20 mL of supernantent as the treatment. Tube is vortexed for I minute to fully suspend HAP in treatment followed by centrifugation at 15,000 rpm for 15 mins. After centrifugation, supernatant is decanted and pellet redistributed by adding 25 ml of water, vortexing, centrifuging at 15,000 rpm for 15 mins, and decanting—making sure pellet breaks up during vortexing. The wash cycle is repeated one more time.

3. HAP Prep for Color Analysis

Vortex pellet in approximately 10 ml of water until fully suspended followed by filtering under vacuum onto a Millipore filter disk (Membrane Filters 4.5 tm, 47 mm Catalog #HAWPO4700, Millipore Corporation, Bedford, Mass.). Prepare a control disk using ≈200 mg of untreated, stained HAP. Filter disks are then dried overnight in flat position and then laminated.

4. Color Analysis of Stained HAP

Whitelight system: HAP disk (untreated HAP control and HAP treatments) is placed in a stabilized sample holder. The color is measured using a digital camera camera having a lens equipped with a polarizer filter (Camera model no. CANON EOS 70D from Canon Inc., Melville, N.Y. with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle such that the light paths meet on the HAP disk. Image analysis is performed using Whitelight with Ultragrab, Optimas and Giant Imaging software.

5. Controls

Usual controls for a single polymer PSRM are water as a treatment followed by exposure to tea, and water without exposure to tea. Additionally, pyrophosphate and polyphosphate are run as internal controls.

6. Results

Calculate changes in L*(brightness), a*(red(+)/green(−)), b*(yellow (−)/blue(+)), and in E (total color) as follows:

$$\Delta L = L^*_{treated\ HAP} - L^*_{untreated\ HAP}$$

$$\Delta a = a^*_{treated\ HAP} - a^*_{untreated\ HAP}$$

$$\Delta b = b^*_{treated\ HAP} - b^*_{untreated\ HAP}$$

$$\Delta E = \sqrt{(\Delta L)^2 + (\Delta a)^2 + (\Delta b)^2}$$

Report results as average ΔL, Δa, Δb, and/or ΔE and percent prevention of stain (AL & AE) versus the negative control.

In-Vitro Pellicle Tea Stain Model (iPTSM)

Tooth staining is a common undesirable side effect of the use of stannous fluoride compositions. Improved stannous fluoride dentifrices described herein provide reduced dental stain formation resulting from more efficient stannous delivery from stannous bound to the polymeric mineral surface active agent. The staining of the tooth surface typically caused by stannous is measured in the clinical situation by using a stain index such as the Lobene or Meckel indices described in the literature. For rapid screening of technologies to help mitigate stannous induced staining, an in vitro lab method is used that provides quantitative estimates of stain prevention potential of stannous fluoride formulations. This method, called iPTSM (in-vitro pellicle stain model), has been shown to correlates well with clinical observations.

The in vitro pellicle tea stain model (iPTSM) is a technique where an in vitro plaque biomass is grown on glass rods from pooled human stimulated saliva over the course of three days. The plaque biomass is treated with agents to determine potential dental staining levels of the various agents. The purpose of this technique is to provide a simple and quick method for determining if compounds have a direct effect on the amount of dental plaque stain. This method utilizes plaque grown on polished glass rods from pooled human saliva with treatments of 5 minutes duration, followed by a 10 minute tea treatment. A trial of this in vitro model can be completed in five days during which up to 12 treatments, including controls can be evaluated.

1. Roughening Glass Rods

Polish new glass rods (5 mm×90 mm) approximately 25 mm from the untapered end on a lathe with silicon carbide paper of 240, 320, 400, and 600 grit used sequentially. After the initial polishing, polish the rods with 600 grit paper only before each test.

2. Saliva Collection & Preparation

Collect saliva daily from a panel of 5-10 people by paraffin stimulation and refrigerate at 4° C. till needed. Pool saliva carefully (so not to pour in wax/mucus) and mix thoroughly.

3. Day 1: Clean glass rods by sonicating with dilute HCl acid, rinse, dry, and polish with 600 grit silicon carbide paper. Rinse rods again with DI water and dry. Insert rods into holders, adjust depth with the depth gauge on the treatment rack, and secure rods in place with rubber O-rings. In the early afternoon, pipette 7 ml of saliva, to which 0.1 wt % sucrose has been added, into 16×75 mm test tubes in a dipping rack. Sucrose is added to saliva on the first day only. Place the rod holders in a modified 37° C. incubator designed to dip roughened glass rods into test tubes to a depth of 1.5 cm at 1 rpm. Dip rods overnight. The design of the incubator is fully shown in Attachment 1. Prepare plaque growth media described above and autoclave for Day 2 (saliva is added on Day 2 before use).

4. Day 2: In the morning, add saliva to plaque growth media and mix thoroughly. Pipette 7 ml of plaque growth media into new 16/75 mm test tubes in new dipping rack. Remove old rack of used tubes, place new dipping rack into incubator, and dip rods for six hours MINIMUM before replacing rods into fresh saliva for overnight dipping.

5. Day 3: On the morning of the third day, pipette 10 ml of DI water into 17×100 mm test tubes in the second and third rows of the treatment rack. This applies to dentifrice treatments only. Rinse solutions may or may not have water rinse tubes in the treatment rack. Pipette fresh pooled saliva into a dipping rack and set aside. Begin tea preparation by adding 550 ml to a glass beaker and heating it in the microwave for 10 minutes. At the end of ten minutes, carefully remove beaker from microwave and drop in a magnetic stir bar to dissipate the possible presence of a super-heated water core. Place 5 Lipton tea bags and a Celsius thermometer into the water and stir on a hot plate. This solution needs to be monitored to insure that it will be no hotter than 50° C. when tea treatment begins. While tea treatment is heated and mixed, prepare dentifrice slurries (1 part dentifrice to 3 parts water, also called a 1 in 4 dilution) using a handheld homogenizer for 30 seconds. Centrifuge slurries for 15 minutes at 10000 rpm. Rinse or active solutions are treated neat. Pipette 7 ml of 50° C. tea solution into a separate dipping rack. Add 5 ml of supernatant/rinse to 16×75 mm glass test tubes in the first row of the treatment rack. Turn off incubator dipping mechanics and remove old saliva dipping rack. Remove all rod holders from the incubator and place submerged rods into old saliva dipping rack to prevent drying over. Using one rod holder at a time, treats by soaking for 5 minutes in the treatment rack. If applicable, wash rods with 2×10 sec dipping in the test tubes containing the DI water in the treatment rack. Place rod holders into prepared tea solution dipping rack and soak for 10 min. Repeat this process with all four rod holders, returning holders to dipping rack to prevent drying out. Place fresh saliva dipping rack into incubator. Return rods to the incubator after treatment/tea soak and dip in fresh saliva for at MINIMUM of 1 hour. This treatment cycle is repeated two more times with fresh treatment/tea/saliva solutions for a total of 3 treatments in a day. After the last treatment, return rods to the incubator and dip overnight in fresh saliva.

6. Day 4: On the morning of the fourth day, turn off incubator dipping mechanics and remove rods from the saliva. Allow rods to dry are then weigh to the nearest 0.1 mg. Record weight and calculate mean dry plaque biomass weights and standard deviations. Place rods into clean sterile cap-able test tubes containing 3 ml of 0.5M KOH, cap tightly and digest overnight at 37° C.

7. Day 5: On the fifth day, remove rods from the incubator and allow cooling. Vortex glass rods to insure all deposits are homogenized. Remove rods from test tubes, filter the solution through 0.45 µm cellulose acetate syringe filters and an read absorbance values for each rod at 380 nm in spectrophotometer. Record results and use absorbance values to calculate mean absorbance value per treatment, standard deviations per treatment, mean absorbance per mg plaque, Standard deviations of mean absorbance per mg plaque, and % increase in absorbance per mg plaque vs. control according to the following equation, % Stain Potential=((Test Product Abs/biomass−Non stannous control Abs/Biomass)/(High Stannous control Abs/Biomass−Non stannous control Abs/Biomass))*100

Example 1—Synthesis of Vinyl Phosphono-monoPhosphate (VPP) or [Vinylphosphonic Phosphoric Anhydride]

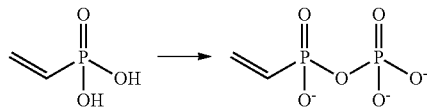

A magnetically stirred dry 500 ml 1 neck round bottom flask was charged with vinyl phosphonic acid (VPA, 25.0 g, 231.5 mmole) and 300 ml DMF under nitrogen. The resulting mixture was stirred for 10 minutes at room temperature yielding a homogenous solution. The tributylamine (64.3 g, 82.7 ml, 1.5 equivalents) was added and stirred 30 min at room temperature yielding a turbid solution that separated into a small upper layer and bulk lower layer on standing.

A second magnetically stirred dry 1000 ml 1 neck round bottom flask fitted with an addition funnel and under nitrogen was charged 1,1'-Carbonyldiimidazole (CDI), (45.1 g, 1.2 equivalents) followed by 300 ml DMF. The resulting mixture was stirred 10 min at room temperature yielding a homogenous solution. Next, the tributylamine/vinyl phosphonic acid solution was added to the CDI solution via the addition funnel over approximately two hours and the resultant mixture was stirred at room temperature overnight yielding a light yellow homogenous solution.

A third magnetically stirred 2000 mL 3 neck round bottom flask fitted with an addition funnel was charged with $H_3PO_4$ (56.7 g, 2.5 equivalents) followed by 400 ml DMF under nitrogen. Resulting mixture was stirred for 15 min at room temperature yielding a homogenous solution. To this mixture was added tributylamine (128.7 g, 165.4 ml, 3.0 equivalents) and the resultant was stirred 30 min yielding a turbid solution. To this turbid solution was added the solution from the second flask over approximately 2 hours via the addition funnel. The resultant was stirred overnight at room temperature to yield a light yellow turbid solution. This solution was stripped of solvent under vacuum (13 Torr) to a final temperature of approximately 70° C. to yield 226 g light yellow syrup.

The resultant was dissolved in 450 ml of water and the pH was adjusted to 10.5 with 50% NaOH (~110 g) yielding 2 phase system. The lower aqueous phase was separated from the upper organic phase. The aqueous phase was stripped of water to a final temperature of approximately 70° C. and vacuum of 13 Torr to yield 212 g of a yellow oil. This oil was heated to approximately 60° C. and 300 ml MeOH was added over 5 min to yield a white precipitate. The MeOH was decanted from the precipitate which was dried to 150.6 g in an oven. P-NMR on the precipitate showed the anticipated phosphono-monophosphate product with 1.22 molar equivalents of orthophosphate, 0.29 equivalents of pyrophosphate and 0.05 molar equivalents of starting vinyl phosphonic acid. H-NMR also showed product, starting material, residual solvents and approximately 0.4 molar equivalents imidazole.

For further purification, the precipitant was dissolved in 300 ml water. Under rapid stirring, 400 ml of MeCOH was added over 30 minutes. The resulting white precipitant was collected by filtration, rinsed with 100 ml MeOH and dried overnight to yield 102.4 g. P-NMR's on this precipitant showed it to be primarily orthophosphate with 0.06 mole equivalents of phosphono-monophosphate product and 0.29 mole equivalents of pyrophosphate.

The water MeOH filtrate was stripped of solvent to a final temperature of approximately 70° C. and pressure of 13 Torr to yield 81.94 g white solid. This solid was shown to be primarily vinyl phosphono-monophosphate with 0.077 molar equivalents of vinyl phosphonate and 0.091 molar equivalents of orthophosphate. Residual imidazole was extracted from this white solid by rapid stirring the solid in 300 ml MeOH at 40° C. 1 hr, filtering off the insoluble solids while the solution was hot, then rinsing the resulting solids twice with 50 ml of room temperature MeOH and drying the resultant solid under high vacuum overnight at room temperature to yield 54.8 g of white powder.

P-NMR on this final sample showed vinyl phosphono-monophosphate with 0.05 molar equivalents of orthophosphate, 0.04 equivalents of pyrophosphate and 0.02 equivalents of vinyl phosphonate. The H-NMR was consistent with vinyl phosphono-monophosphate product with 0.02 molar equivalents of imidazole and 0.09 equivalents of methanol. Using an internal standard, the total active was calculated to be 80.8%, which represents a yield of 82%.

Example 2—Synthesis of Methyl-Vinyl Phosphono-monoPhosphate (MVPP) or [Methylvinylphosphonic Phosphoric Anhydride]

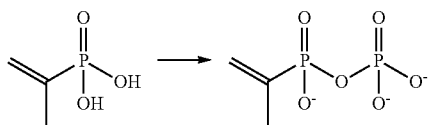

The procedure of Example 1 was followed with the substitution of methy-vinyl phosphonic acid for vinyl phosphonic at 1/14 molar scale of Example 1. Final purity was 71.9% and yield was 31.2%.

Example 3—Synthesis of (Methylenyl Phosphono-monoPhosphate)-Methacrylate [or ((Methacryloxyloxy)Methyl)Phosphonic Phosphoric Anhydride]

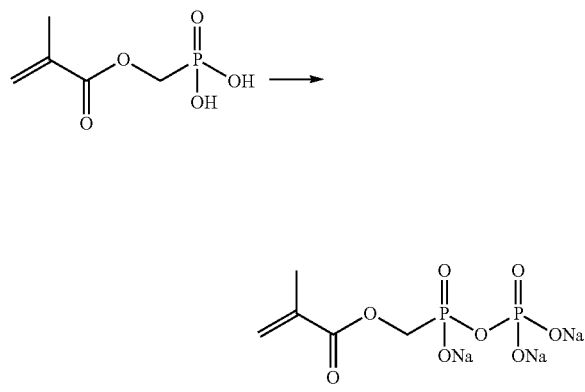

A magnetically stirred dry 50 ml 1 neck round bottom flask was charged with (Methylenyl Phosphonic Acid)-Methacrylate (0.5 g, 2.77 mmole) and 10 ml DMF under nitrogen. The resulting mixture was stirred for 10 minutes at room temperature yielding a homogenous solution. The tributylamine (0.77 g, 1.0 ml, 1.5 equivalents) was added and stirred 30 min at room temperature yielding a homogenous solution.

A second magnetically stirred dry 10 ml 1 neck round bottom flask fitted under nitrogen was charged 1,1'-Carbonyldiimidazole (CDI), (0.54 g, 1.2 equivalents) followed by 10 ml DMF. The resulting mixture was stirred 10 min at room temperature yielding a homogenous solution. Next, the tributylamine/(Methylene Phosphonic Acid)-Methacrylate solution was added to the CDI solution over 1 minute and the resultant mixture was stirred at room temperature 4 hours yielding a light yellow homogenous solution.

A third magnetically stirred 50 mL 1 neck round bottom flask was charged with $H_3PO_4$ (0.68 g, 2.5 equivalents) followed by 15 ml DMF under nitrogen. Resulting mixture was stirred for 15 min at room temperature yielding a homogenous solution. To this mixture was added tributylamine (1.54 g, 2.0 ml, 3.0 equiv.) and the resultant was stirred 30 min yielding a turbid solution. To this turbid solution was added the solution from the second flask over 1 minute. The resultant was stirred overnight at room temperature to yield a light yellow turbid solution. This solution was stripped of solvent under vacuum (13 Torr) to a final temperature of approximately 65° C. to yield 24.5 g light yellow syrup.

The resultant was dissolved in 100 ml of water and the pH was adjusted to 8 with 1N NaOH (~14 g) yielding a milky white system, which was subsequently concentrated at 65° C. and 13 Torr 25 to 24.5 g of light yellow syrup. This syrup was added to 50 ml MeOH was added over 5 min to yield a white precipitate. The MeOH was decanted to remove the precipitate, then the MeOH was stripped under vacuum to yield 7.4 g of gelatinous solids. P-NMR on the gelatinous solids showed the anticipated phosphono-monophosphate product with 1 equivalent product, 0.55 molar equivalents of orthophosphate, 0.40 equivalents of the anhydride of starting phosphonate.

The bulk of gelatinous solids was stirred in 50 ml EtOH 1 hr at RT yielding an insoluble ppt. The ppt was filtered, rinsed twice with 10 mL of fresh EtOH and hood dried O/N to 238 mg solids. The P-NMR of the solids showed product peaks doublets (1.1/1.0 ppm & −8.4/−8.5 ppm), phosphate (2.04 ppm), product anhydride (2.9 ppm) in a ratio of 100:70:10 as well as other minor unknowns. The H-NMR shows the dried solids to be consistent with product containing ~12 mole % imidazole, residual EtOH and other minor unknowns.

Example 4—Synthesis of (Ethyl Phosphono-mono-Phosphate) (Butyl) Acrylamide or [(2-(N-Butylacrylamido)Ethyl)Phosphonic Phosphoric Anhydride]

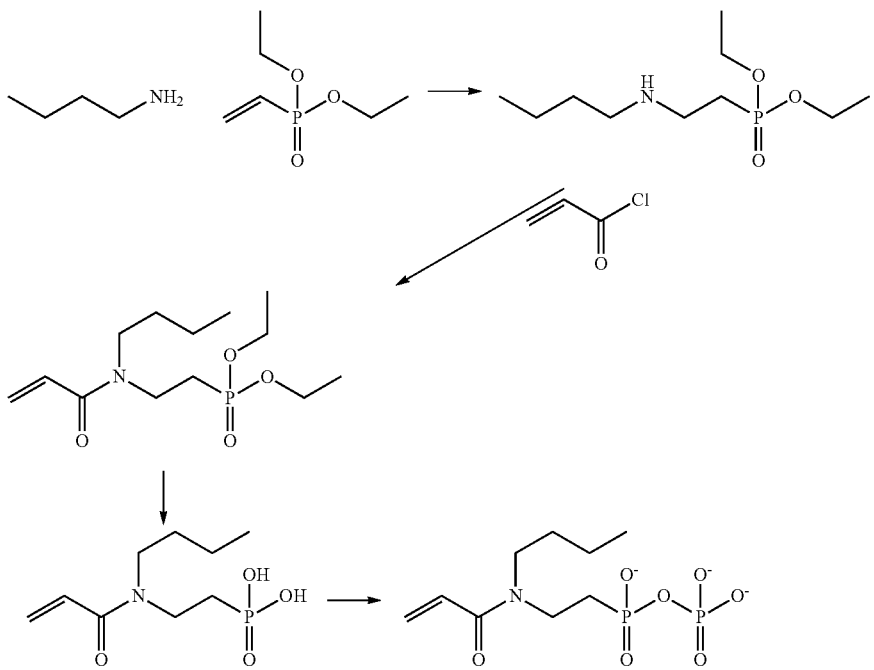

A magnetically stirred dry 25 ml 2 neck round bottom flask was charged with n-butylamine (6.3 mL, 63 mmole) and heated under dry nitrogen to 78° C. Diethyl vinyl phosphonate (1.0 ml, 6.3 mmole) was added and stirred overnight. Resulting mixture was rotary evaporated at around 45° C. and 20 mmbar to recover 1.38 g of material at high purity diethyl ethyl phosphonate butyl amine by P-NMR (92% recovery).

A magnetically stirred dry 25 ml 2 neck round bottom flask was charged with diethyl ethyl phosphonate butyl amine (1.1 g, 4.6 mmole), 2 mL of dichloromethane and 6 mL of 1N NaOH. Resultant was stirred and cooled in an ice bath. A mixture of 2 mL of dichloromethane and 0.368 g of acryloyl chloride was added dropwise to this flask over 30 minutes. Resultant was diluted with 10 mL of dichloromethane extracted in a separatory funnel 2×25 mL 1N HCl, 1×25 mL saturated NaCl with 10 mL rinses with dichloromethane of the aqueous phases. Resulting combined organic phases were dried over anhydrous sodium sulfate and filtered. Solvent was removed by rotary evaporation at approximately 35° C. to yield 0.84 g (72%) of product.

The ethyl ester groups on this product were removed by dissolving the entire lot in 4 mL of dichloromethane in a magnetically stirred 100 mL 2 neck flask under dry nitrogen in an iced bath then adding a mixture of 1 mL dichloromethane and 2 mL of trimethyl bromo silane over 20 minutes. An additional 1 mL of dichloromethane and then a mixture of 1 mL of dichloromethane and 1 mL of trimethyl bromo silane were then added. After 2 hours, 30 mL of MeOH was added and allowed to stir for 10 minutes followed by 0.21 mg of butylated hydroxy toluene in 1 mL dichloromethane. Volatiles were removed by rotary evaporate at around 40° C. Resultant was purified by dissolving in 50 mL of dichloromethane and extracting with a mixture of 25 mL of 0.1 N NaOH and 25 mL of 1 N NaOH. Aqueous phase was extracted a second time with 25 mL of dichloromethane than acidified with to pH 1 with 1N HCl then rotary evaporated to near dryness. Resulting residue was diluted with 50 mL of EtOH and rotary evaporated to near dryness 3 times to remove the water. Resultant residue was then diluted with 10 mL of pentane and evaporated to near dryness 2 times to remove residual EtOH. Final recovery near quantitative.

Addition of the phoshono-phosphate group was performed as in Example 3. The purification step was slightly modified. An diethyl ether (1 volume equivalent) extraction was performed on the crude reaction mixture then the solution was vacuum stripped at 30-35° C. Residues was dissolved in 25 mL of water and the pH adjusted to 7 with 1N NaOH followed by vacuum stripping of water at 40-45° C. to leave a liquid residue. Next, 100 mL of methanol was added to the residue resulting in a precipitant that was collected and dried under vacuum to yield approximately 9.1 grams at 80% active by P-NMR.

Example 5—Synthesis of (4-VinylBenzyl) Phosphono-monoPhosphate or [(4-Vinylbenzyl)Phosphonic Phosphoric Anhydride]

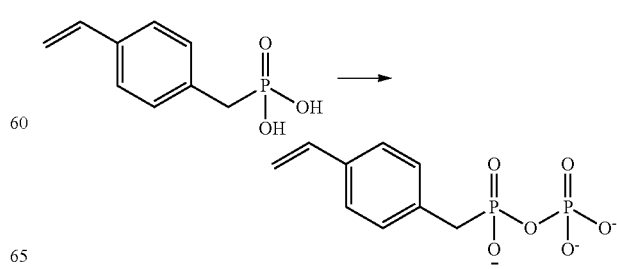

A magnetically stirred dry 50 ml 1 neck round bottom flask was charged with (4-VinylBenzyl) Phosphonic Acid (4.0 g, 20.2 mmole) and 20 ml DMF under nitrogen. The resulting mixture was stirred for 10 minutes at room temperature yielding a homogenous solution. The tributylamine (5.6 g, 7.2 ml, 1.5 equivalents) was added and stirred 30 min at room temperature yielding a homogenous solution.

A second magnetically stirred dry 10 ml 1 neck round bottom flask fitted under nitrogen was charged 1,1'-Carbonyldiimidazole (CDI), (4.9 g, 1.2 equivalents) followed by 25 ml DMF. The resulting mixture was stirred 10 min at room temperature yielding a homogeneous solution. Next, the tributylamine/(4-VinylBenzyl) Phosphonic Acid solution was added to the CDI solution over 1 minute and the resultant mixture was stirred at room temperature 4 hours yielding a light yellow homogeneous solution.

A third magnetically stirred 100 mL 1 neck round bottom flask was charged with $H_3PO_4$ (5.94 g, 3.0 equiv) followed by 25 ml DMF under nitrogen. Resulting mixture was stirred for 15 min at room temperature yielding a homogeneous solution. To this mixture was added tributylamine (13.1 g, 16.8 ml, 3.5 equivalents) and the resultant was stirred 30 min yielding a turbid solution. To this turbid solution was added the solution from the second flask over 1 minute. The resultant was stirred overnight at room temperature to yield a light yellow solution. This solution was stripped of solvent under vacuum (13 Torr) to a final temperature of approximately 65° C. to yield 49.8 g light yellow syrup.

The resultant was added to 30 ml of water and the pH was adjusted to 8.5 with 1N NaOH (~127 g) yielding a milky white system, which was subsequently concentrated at 65° C. and 13 Torr to 58.2 g of light yellow syrup. This syrup was added to 40 ml MeOH was added over 20 min to yield a white precipitate. P-NMR on the paste showed it to be approximately 95% phosphate. The MeOH was decanted to remove the precipitate, then the MeOH was stripped to yield 7.23 g of white paste. The P NMR on the white paste showed the anticipated phosphono-monophosphate product with 1 equivalent product, 0.16 molar equivalents of orthophosphate, 0.05 equivalents of pyrophosphate, 0.25 equivalents of the anhydride of starting phosphonate and 0.065 equivalents of starting phosphonate.

The bulk of the white paste was stirred in 75 ml MeOH 1 hr at room temperature. A portion of the paste dissolved, however a portion remained insoluble. The insoluble portion was filtered and rinsed twice with 10 mL of fresh MeOH. The resulting solid was dried under high vacuum O/N to yield 1.97 g solids. The P-NMR of the solids showed product peaks doublets (1.1/1.0 ppm & −8.4/−8.5 ppm), phosphate (2.04 ppm), product anhydride (2.9 ppm) in a ratio of 100:70:10 as well as other minor unknowns. The H-NMR shows the dried solids to be consistent with product containing ~12 mole % imidazole, residual EtOH and other minor unknowns. The yield of the final solids was 23.7% of theoretical.

Example 6—Synthesis of (Bis(Methylene Phosphonate Anhydride)Aminopropyl)-Methacrylate Polymer or [4-(3-(Methacryloyloxy)Propyl)-1,4,2,6-Oxazadiphosphinane-2,6-Bis(Olate) 2,6-Dioxide Polymer]

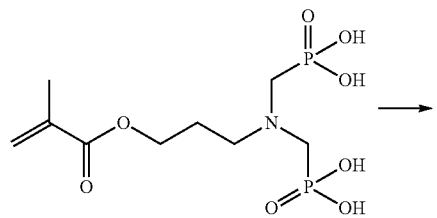

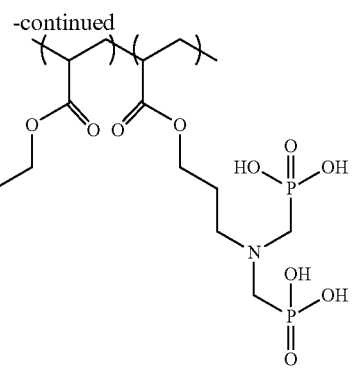

A magnetically stirred dry 250 ml 3 neck round bottom flask was charged with (Bis(Methylene Phosphonic Acid)aminopropyl)-Methacrylate (3.0 g, 9.06 mmole) and 100 ml DMF under nitrogen. The resulting mixture was stirred for 10 minutes at room temperature yielding a homogenous solution. The tributylamine (5.03 g, 6.5 ml, 3.0 equivalents) was added and stirred 30 min at room temperature yielding a homogeneous solution.

A second magnetically stirred dry 100 ml 1 neck round bottom flask fitted with an addition funnel and under nitrogen was charged 1,1'-Carbonyldiimidazole (CDI), (2.2 g, 1.5 equivalents) followed by 40 mL DMF. The resulting mixture was stirred 10 min at room temperature yielding a homogenous solution. The CDI solution was added via addition funnel over approximately one hour to the first flask and the resultant mixture was stirred at room temperature overnight followed by standing for 1 week to yield a white precipitate. The precipitant was collected by filtration, slurried in 100 mL water and the pH adjusted to ≈9 with 1N NaOH yielding a turbid solution. This solution was evaporated overnight under flowing air to 2.4 g. The H & P-NMR's showed the precipitate to be polymer with some monomer. The P-NMR showed polymeric target anhydride (at 12-13 ppm) and starting di-acid (at 6-7 ppm) as well as monomer peaks (at 11.8-12 ppm) in a ratio of 36:53:11. The bulk of the precipitant was sonicated in 100 mL water 1 hr yielding a turbid solution which was filtered using a 250 mL Stericup Durapore with 0.22 μm PVDF filter disk yielding a clear solution. This was brought up to 250 ml and purified by dialysis in a Thermo Scientific Slide-A-Lyzer dialysis flask (2K MWCO, 250 ml) against 5 gallons RO water (pH adjusted to 8.5 w 1N NaOH) for 7 days yielding 1.29 g white solid (17-DF-5835-5) after freeze drying. The P-NMR showed a broad anhydride peak at 12-13 ppm & a di-acid peak at 6.4-7.4 ppm in a 39.2:60.8 molar ratio. Activity was calculated to be 87.8% polymer & 12.2% water/inactives.

Example 7—Synthesis of (Ethyl Phosphono-mono-Phosphate)-Methacrylate or [(2-(Methacryloyloxy)Ethyl)Phosphonic Phosphoric Anhydride]

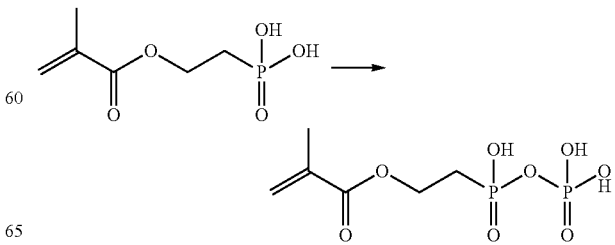

A magnetically stirred dry 100 ml 1 neck round bottom flask was charged with (Ethyl Phosphonic Acid)-Methacrylate (3 g, 15.5 mmole) and 30 ml DMF under nitrogen. The resulting mixture was stirred for 10 minutes at room temperature yielding a homogenous solution. The tributylamine (4.3 g, 5.5 ml, 1.5 equivalents) was added and stirred 30 min at room temperature yielding a homogeneous solution.

A second magnetically stirred dry 25 ml 1 neck round bottom flask fitted under nitrogen was charged 1,1'-Carbonyldiimidazole (CDI), (3.76 g, 1.5 equivalents) followed by 20 ml DMF. The resulting mixture was stirred 10 min at room temperature yielding a homogeneous solution. Next, the tributylamine/(Ethyl Phosphonic Acid)-Methacrylate solution was added to the CDI solution and the resultant mixture was stirred at room temperature 4 hours yielding a light yellow homogeneous solution.

A third magnetically stirred 500 mL 1 neck round bottom flask was charged with $H_3PO_4$ (4.55 g, 3.0 equivalents) followed by 25 ml DMF under nitrogen. Resulting mixture was stirred for 15 min at room temperature yielding a homogeneous solution. To this mixture was added tributylamine (12 g, 15.4 ml, 4.2 equiv.) and the resultant was stirred 30 min yielding a turbid solution. To this turbid solution was added the solution from the second flask over 1 minute. At about 1 hour of stirring, a white precipitant began to form. The resultant was stirred overnight at room temperature with additional precipitant forming. The P-NMR showed product peaks doublets (7.2/7.3 ppm & −8.75/−8.84 ppm), phosphate (2.14 ppm), product anhydride (8.9 ppm) & pyrophosphate (−9.26 ppm) in a ratio of 100:427:12:15.

To the crude Rx solution (≈90.7 g) was added with stirring 200 mL ethyl ether over 30 min yielding a white ppt which was collected by filtration, rinsed with additional ether and dried overnight under vacuum (<1 Torr) at room temperature to yield 7.85 g white precipitant. To the resultant filtrate was added an additional 200 mL ethyl ether with stirring over 30 min yielding a two layer system with a free flowing top layer and lower viscous oil layer. The top layer was decanted and the lower oil layer dried overnight under vacuum (<1 Torr) at room temperature to 2.33 g waxy solid. To the decanted layer was added an additional 400 ml ether over 30 min with stirring yielding a turbid solution. The turbid solution was placed in a freezer (−15° C.) overnight yielding a clear free flowing top layer and a viscous oil lower layer. The top layer was decanted and the lower oil layer dried overnight under vacuum (<1 Torr) at room temperature to 1 hr to 1.19 g waxy solid.

The white precipitant was shown by H-NMR to be a mixture of product:imidazole:tributyl amine in a molar ratio of 100:1150:220, while the P-NMR showed a mixture of product:phosphate:pyro in a molar ratio of 100:625:35.

The first waxy solid was shown by H-NMR to be a mixture of product:imidazole:tributyl amine in a molar ratio of 100:230:170. The P-NMR showed a mixture of product: phosphate in a molar ratio of 100:89.

The second waxy solid was shown by H-NMR to be a mixture of product:imidazole:tributyl amine in a molar ratio of 100:100:150. The P-NMR showed a mixture of product: phosphate in a molar ratio of 100:79.

Waxy solids were combined and dissolved in 50 mL deionized water. The pH of the resultant solution was adjusted from 2.9 to 8.6 with 19.3 g 1N NaOH yielding a turbid solution. This solution was extracted 1× with 50 mL ethyl ether. The resultant aqueous layer had a pH=7.5 was trimmed to 8.0 with additional 1N NaOH. Residual ether was removed form the aqueous layer on roto-vap at room and 20 Torr. The water was removed from the aqueous layer via freeze-drying yielding 2.61 g tan solid.

The H & P-NMR's showed a mixture of product:imidazole:NBut3 in a molar ratio of 100:160:50. The P-NMR shows a mixture of product:phosphate in a molar ratio of 100:101.

Tan solid was stirred in 50 mL MeOH for 30 min yielding an insoluble solid. Solid was collected by filtration, rinsed 2×10 ml fresh MeOH and dried overnight at room temperature at <1 Torr to yield 1.79 g cream colored solid. The H-NMR's was consistent with product containing ~1 mole % imidazole. The LCMS demonstrated a mass consistent with the M+H protonated form at 273. The H-NMR of methanol extract showed it to be primarily imidazole containing ~3 mole % product.

Activity was calculated by combined H-NMR and P-NMR and found to be 74.4%.

Example 8—Synthesis of (Propyl Phosphono-monoPhosphate)-Methacrylate or [(3-(Methacryloy-loxy)Propyl)Phosphonic Phosphoric Anhydride]

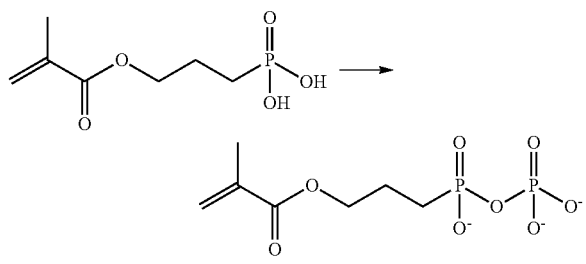

The procedure of Example 7 was followed substituting 5.5 g (26.4 mmol) (Propyl Phosphonic Acid)-Methacrylate for (Ethyl Phosphonic Acid)-Methacrylate. All reagents were scaled to keep the molar equivalence the same. After final evaporation, 5.17 g of cream solid was collected and shown to be 67.8% active.

Example 9—Synthesis of (Ethyl Phosphono-monoPhosphate)-Acrylamide or [(2-Acrylamidoethyl)Phosphonic Phosphoric Anhydride]

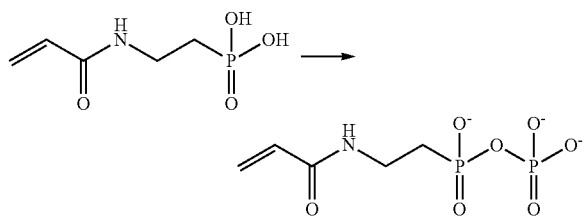

The procedure of example 5 was followed using (acrylamido)ethyl phosphonic acid (37 mmoles) in place of vinyl benzyl phosphonate for creation of the crude yellow solution, with increased quantities of all reagents at equivalent molar ratios to example 5.

The purification procedure of the crude solution was modified from example 5. DMF was partially removed at room temperature with flowing dry nitrogen to yield 46.8 g of a viscous yellow oil. This oil was dissolved in ≈75 mL of water and the pH adjusted to 8 by addition of 1 N NaOH over 20 minutes. A small organic layer 9.4 g of tributyl amine formed and was decanted. The aqueous phase was further dried under flowing dry nitrogen to 147.5 g, then 220 mL of MeOH was added over 30 minutes to yield a white precipitate. The precipitate was filtered and the resulting filtrate dried yield 22.7 g of brown paste, which P NMR showed to be mostly product. The brown paste was slurried in 100 mL of EtOH under vigorous stirring for 6 hour at room temperature. A solid formed and was collected by filtration, rinsed with fresh EtOH 2×25 mL and dried at <1 Torr overnight to yield 10.94 g of tan solid. The solid contained 69% phosphono-monophosphate product by NMR.

Example 10—Synthesis of (Methylene Phosphono-monoPhosphate)-Acrylate or [((acryloyloxy)methyl)phosphonic phosphoric anhydride]

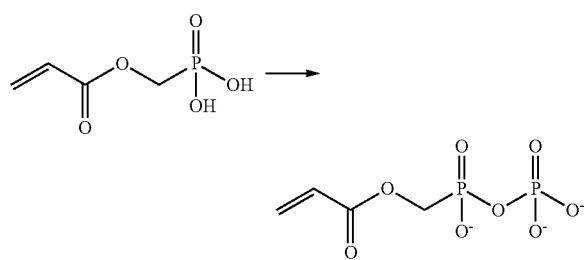

The procedure of Example 3 is followed substituting (Methylene Phosphonic Acid)-Acrylate for (Methylene Phosphonic Acid)-Methacrylate Example 11—Synthesis of (Ethyl Phosphono-monoPhosphate)-Vinyl Ether or [(2-(vinyloxy)ethyl) phosphonic phosphoric anhydride]

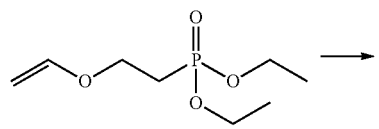

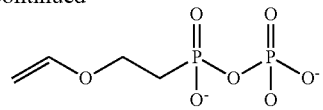

A dry, septum sealed, nitrogen flushed, magnetically stirred 250 mL three neck round bottom flask was charged with diethyl (2-(vinyloxy)ethyl)phosphonate (3 g, 14.4 mmol) and 30 ml $CH_2Cl_2$ and chilled to 0-5° C. To this flask was added bromotrimethylsilane (5.7 mL, 43.2 mmol, 3.0 equivalents) over 1 minute. After addition the solution was stirred for 2 hours at room temperature and the solution stripped of solvent at 30° C. and <1 Torr to yield 4.59 g yellow oil. To this was added 15 g of triethylamine, 30 g MeOH and 60 mg of phenothiazine (inhibitor) that had been pre-chilled over dry ice and acetone. Resultant was allowed to warm to room temperature under constant stirring, then put under vacuum at room temperature to remove solvent and volatiles for 1 hour yielding 3.84 g of viscous turbid yellow oil. P-NMR and H-NMR were consistent with amine mono-triethyl amine salt.

The procedure of Example 7 was followed to create and purify (Ethyl Phosphono-monoPhosphate)-Vinyl Ether resulting in 4.04 g of tan solid after methanol extraction. The H-NMR's was consistent with product containing ~5 mole % imidazole. The P-NMR was consistent with a product phosphono-monophosphate to residual phosphate ratio of 100:112. The LCMS demonstrated a mass consistent with the M+H protonated form at 231. Activity was calculated by combined H-NMR and P-NMR and found to be 52%.

Example 12—Synthesis of (Ethyl Phosphono-monoPhosphate)-Acrylate or [(2-(Acryloyloxy) Ethyl)Phosphonic Phosphoric Anhydride]

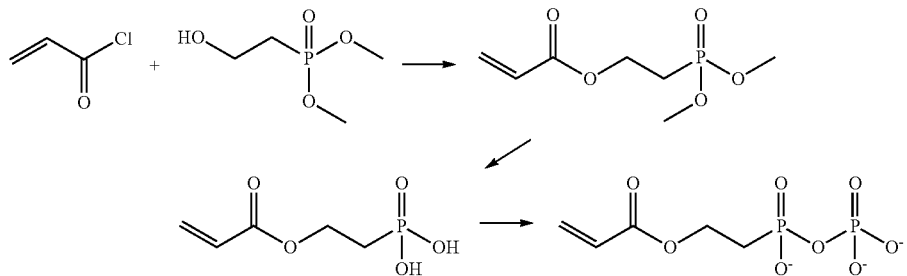

A dry magnetically stirred 1 L three neck round bottom flask was charged with dimethyl (2-hydroxyethyl)phosphonate (24.7 g, 16 mmol), triethyl amine (17.8 g 176 mmol) and 400 ml $CH_2Cl_2$ and chilled to 0-5° C. To this flask was added a solution of the acryloyl chloride (14.95 g 16.51 mmole) in 100 ml $CH_2Cl_2$ over 1.5 hours while maintaining reaction temperature of 0-5° C. After the addition was complete the reaction temp was maintained at 0-5° C. for an additional 2 hours followed by warming to RT and stirring overnight.

The resulting light brown turbid solution was extracted 2×200 ml deionized water, and the oil layer dried over anhydrous $MgSO_4$ and then filtered. The filtrate was stripped of solvent yielding 30.5 g brown oil. The H, C & P-NMR's were consistent with the first intermediate, (Ethyl, dimethyl phosphonate)-Acrylate. The yield was 91.4%.

The above brown oil was charged into a dry magnetically stirred 500 mL three neck round bottom flask with 250 mL of dichloromethane. The flask and contents were chilled to 10° C. and 67.3 g (3 equivalents) of bromotrimethylsilane was added over 30 minutes. The flask was allowed to warm to room temperature and stirred overnight. Resultant solution was stripped of solvent at 30° C. followed by stirring under high vacuum (<1 Torr) overnight to yield 37 g of light oil. To the oil, 200 mL of methanol was added over 10 minutes at room temperature followed by stirring at room temperature for 3 hours. Resultant solution was stripped of solvent at 30° C. followed by stirring under high vacuum (<1 Torr) overnight to yield 26.1 g of a viscous tan oil. H NMR and P NMR were consistent with product. The yield was 98.9%.

The procedure of example 5 was followed using (acryloyloxy)ethyl phosphonic acid in place of vinyl benzyl phosphonate for creation of the crude yellow solution. P NMR and H NMR showed 72% yield of desired product.

Example 13—Synthesis of Mixed Vinyl Phosphono-Phosphates

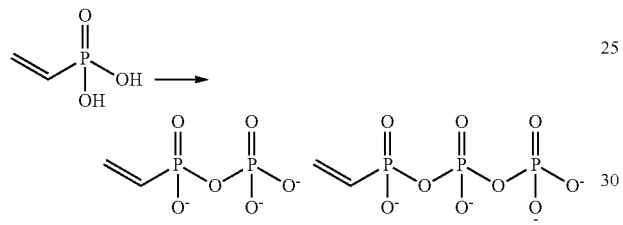

The procedure of Example 1 was followed with the substitution of pyrophosphoric acid for phosphoric acid at 1/12 molar scale of Example 1. After removal of the DMF solvent to yield a yellow oil and addition of 1N NaOH, 24.1 g of white solid was collected after sparging overnight with nitrogen. This sample was shown by PNMR to contain vinyl phosphono-pyrophosphate (VPPP), vinyl phoshono-monophosphate, starting material, starting material anhydride, phosphate, pyrophosphate and triphosphate. The ratio of vinyl phosphono pyrophosphate:vinyl phosphono-monophosphate was 1:1.7.

Example 14 Synthesis of Vinyl Sulfonate Methyl Ester (VSME)

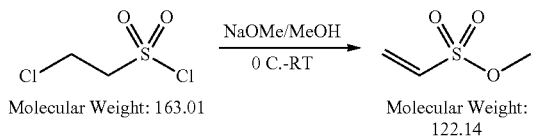

A magnetically stirred dry 500 ml 3 neck round bottom flask equipped with an addition funnel and a thermometer was charged with 250 mL of methanol under nitrogen and cooled to 0° C. The 2-chloroethanesulfonyl chloride (Aldrich) was added to the flask over 15 minutes with no observed exotherm. Next 25% NaOMe/MeOH (Aldrich) was added over 2 hours at rate to maintain a temperature of approximately 0° C. During the addition a white precipitant, (NaCl) formed. The resultant was stirred an additional hour at 0° C. and then allowed to warm to room temperature and stirred overnight. The precipitant was removed by filtration and the filtrate was stripped of solvent yielding 20.33 g white gel. This gel was slurried in 200 ml $CH_2Cl_2$ for 1 hour. The resultant was filtered and the filtrate stripped of solvent yielding 9.47 g tan oil.

$^1$H & $^{13}$C-NMR's showed a mixture of desired product, VSMS, and methyl 2-methoxyethane-1-sulfonate in a 3:0.6 ratio, 79.8% product by weight. The H-NMR also shows and acid peak at ~10 ppm. A test of 0.05 g tan oil in 1 ml water showed a pH of approximately 1 by litmus.

8.8 g of tan oil was dissolved in 100 ml $CH_2Cl_2$ and stirred over 5 g sodium bicarbonate. The resultant was filtered and the filtrate stripped of solvent yielding 8.02 g light yellow clear oil.

A test of 0.05 g of the yellow clear oil in 1 mL water showed a pH of approximately 6-7 by litmus. Ratio of VSME to methyl 2-methoxyethane-1-1sulfonate was the same, yielding 79.8% active.

Example 15 Synthesis of Sodium Vinyl Benzyl Sulfonate

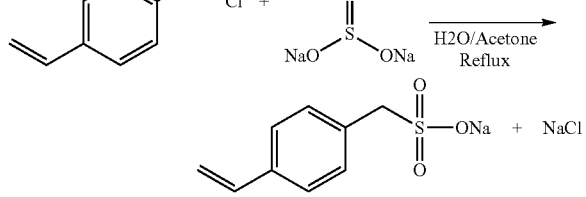

A magnetically stirred dry 250 ml 3 neck round bottom flask equipped with a heating mantel, addition funnel and reflux condenser was charged with 9.5 g of sodium sulfite (75.5 mmol) and 100 ml water. The resultant solution was heated to 100° C. under nitrogen. Next, 4-vinylbenzyl chloride (9.6 g, 62.9 mmol) in 15 ml acetone was added over 30 minutes. The resultant was refluxed 12 hours, cooled to room temperature and allowed to stand overnight with no resulting precipitant. Next, under rapid stirring, 100 ml acetone was added resulting in a lower paste-like layer. The water/acetone supernatant was decanted. The paste was rinsed with 25 mL of fresh acetone which was then decanted. The paste was dried overnight under vacuum, 14 torr, and room temperature to yield 8.5 g solids. This dried layer was shown to be primarily homopolymer by $^1$H-NMR. The water/acetone decanted layers were evaporated to approximately 75 ml yielding a white ppt. The ppt was collected by filtration, rinsed 2×25 ml acetone and dried overnight under vacuum, 14 torr, and room temperature to yield 2.14 g solids.

The $^1$H-NMR of this second precipitant was consistent with monomer product at close to 100% activity.

Example 16 Co-Polymerization of Vinyl Phosphonic Acid (VPA) and Sodium Vinyl Sulfonate (SVS)

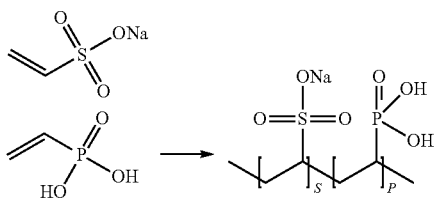

VPA (2.0 g, 18.5 mmoles) and SVS (25% aqueous solution, 7.9 g, 15.2 mmoles), initial molar ratio of SVS to VPA of 45 to 55, were charged in a round bottom flask. The flask was purged with nitrogen for 15 minutes and heated to 90° C. Two separate aqueous solutions containing 2,2'-azobis(2-methylpropionamidine) dihydrochloride (AAPH, Aldrich, 25.8 mg in 1.2 mL water, 0.3% molar basis to total monomers added) and 1-Octanethiol (CTA, Aldrich 55.6 mg in 1.2 mL of water, 1.1% molar basis to total monomers added) were also prepared. These two solutions were then added to the heated stirred flask containing the monomers every 30 minutes over the course of 6 hours. After the final addition, the resulting solution was allowed to stir overnight at 90° C.

$^1$H-NMR & $^{31}$P-NMR were run on the crude reaction solutions. Typical monomer conversions of 95-99% were observed with a broad P polymer peak at ~31 ppm from the phosphonate group.

The crude reaction solutions were diluted to 1 wt % polymer in water and the pH adjusted to 6. These solutions were dialyzed with 2K molecular weight cut off dialysis membranes against reverse osmosis water for 5-7 days.

The resultant solution was stripped of water under vacuum to yield white to cream color solids which was further dried in a vacuum oven overnight to yield 2.74 g of solid.

The phosphonate content in the polymers were determined by preparing an NMR sample with purified polymer & trimethyl phosphate (TMP) in D$_2$O. The $^1$H & $^{31}$P-NMR's were run from which the phosphonate content was calculated from the H and P peaks of the internal standard (TMP) relative to the polymer peaks and water. Based on this analysis, the polymer contained 55.7 mol % repeat units resulting from SVS and 44.3 mol % repeat units resulting from VPA. The water content was calculated to 9.6% on a weight basis. The total recovery of monomers in the post dialysis polymer was calculated to be 57% on a molar basis.

Example 17 Co-Polymerizations of Vinyl Phosphonic Acid and Sodium Vinyl Sulfonate (SVS)

The procedure of Example 16 was repeated for different starting ratios of VSA and VPA. The resulting polymer compositions from different starting ratios and total yield, including Example 16 are shown in the Table 1 below. A Wyatt Gel Permeation Chromatography (GPC) system, using a Polymer Standards Service (PSS) MCX 1000A column and both a Wyatt HELEOS II light scattering detector and a Wyatt Optilab Differential refractive index detector, was used for calculation of polymer molecular weight using the internal Wyatt Astra 6 software.

TABLE 1

| % Total Monomer SVS Loaded | % Total Monomer VPA Loaded | % AAPH Loaded | % CTA Loaded | % Sulfonate in Polymer | % Phosphonate in Polymer | Total Molar Yield | Mn (kDa) | Mw (kDa) |
|---|---|---|---|---|---|---|---|---|
| 75.0% | 25.0% | 0.3% | 1.0% | 80% | 20% | 85% | 5.4 | 7.9 |
| 70.0% | 30.0% | 0.3% | 1.1% | 69% | 31% | 66% | 4.2 | 5.9 |
| 50.0% | 50.0% | 0.3% | 1.0% | 57% | 43% | 73% | — | — |
| 45.1% | 54.9% | 0.3% | 1.1% | 56% | 44% | 57% | 3.4 | 4.5 |
| 40.0% | 60.0% | 0.3% | 1.0% | 44% | 56% | 64% | 4.2 | 5.3 |
| 20.0% | 80.0% | 0.3% | 1.0% | 34% | 66% | 58% | — | — |

Example 18 Co-Polymerization of Vinyl Phosphonic Acid (VPA) and Acrylic Acid (AA)

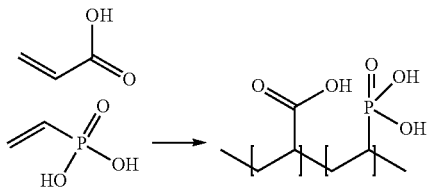

The procedure in Example X was repeated using an initial charge of 19 mmol of VPA in 1.5 mL of water. Acrylic acid, 28.5 mmol in 1.6 mL of water was added (0.3 mL) along with the 0.1 mL of AAPH and CTA every 30 minutes. An additional 3 mL of water was added half way through the additions. The final polymer collected was 2.87 g after dialysis and was found to be 30% phosphonate and 70% acrylate.

Example 19 Co-Polymerization of Vinyl Phosphono-monoPhosphate (VPP) and Sodium Vinyl Sulfonate (SVS)

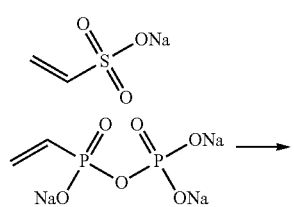

-continued

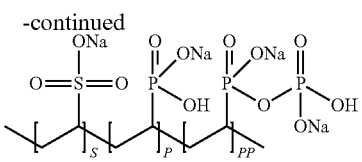

VPP (Example 1, 2.05 g active, 8.87 mmoles) and SVS (25% aqueous solution, 3.77 g, 7.25 mmoles), initial molar ratio of SVS to VPP of 45 to 55, were charged in a round bottom flask, and the headspace of the flask purged with flowing nitrogen for 15 minutes. The flask was sealed and heated to 60° C. at which time Ammonium Persulfate (APS, Aldrich, 183 mg, 5% relative to total monomers) was added in 0.50 ml water. The resultant was stirred 24 hrs at 60° C.

$^1$H-NMR & $^{31}$P-NMR were run on the crude reaction solutions. Typical monomer conversions of 95-99% were observed with broad P polymer peaks at ~18 to 23 ppm from the phosphonate group and −6 to −10 from the phosphate bound to the phosphonate group.

The crude reaction solutions were diluted to 1 wt % polymer in water and the pH adjusted to 8.5. These solutions were dialyzed with 2K molecular weight cut off dialysis membranes against reverse osmosis water for 5-7 days.

Water was removed from the product by freeze drying yielding 2.22 g white solid.

The phosphonate content in the polymers were determined by preparing an NMR sample with purified polymer & trimethyl phosphate (TMP) in D$_2$O. The $^1$H & $^{31}$P-NMR's were run from which the phosphonate content was calculated from the H and P peaks of the internal standard relative (TMP) relative to the polymer peaks and water. The P-NMR shows broad phosphono-phosponate peaks at ~18 to 23 ppm and −6 to −10 ppm in approximately 1:1 ratio and also a phosphonate peak at ~26-28 ppm. Based on the $^{31}$P-NMR areas at 18-23 and 26-28 ppm, the phosphono-phosphonate:phosphonate ratio is 94.9:5.1. Based on this analysis, the polymer contained 56 mol % repeat units resulting from SVS, 42 mol % repeat units resulting from VPP and 2 mol % repeat units resulting from VPA. The water content was calculated to 23% on a weight basis. The total recovery of monomers in the post dialysis polymer was calculated to be 65% on a molar basis.

Example 20 Co-Polymerizations of Vinyl Phosphono-monoPhosphate (VPP) and Sodium Vinyl Sulfonate (SVS)

The procedure of Example 19 was repeated for different starting ratios of VSA and VPP. The resulting polymer compositions from different starting ratios and total yield, including Example 19 are shown in Table 2 below.

Example 21 Co-Polymerization of Methyl-Vinyl Phosphono-monoPhosphate (MVPP) and Sodium Vinyl Sulfonate (SVS)

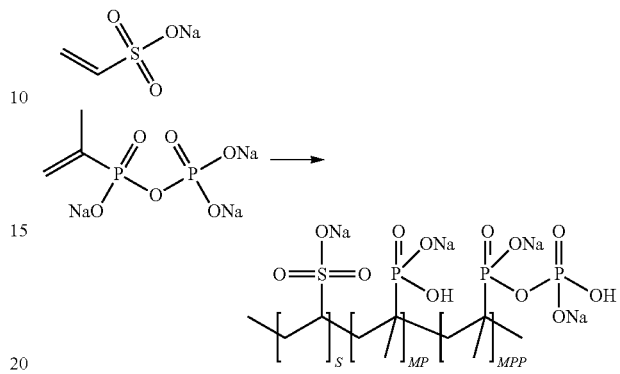

The procedure of Example 19 was repeated using MVPP (Example 2) in place of VPP and a ratio MVS to MVPP of 55 to 45, respectively, with the following changes.

At 24 hours of run time, the MVPP monomer conversion via NMR was around 75%, so an additional 3 mole % APS in water was added and the reaction allowed to stir for an additional 24 hours at 60° C. At this point, the MVPP monomer conversion was around 95%.

Dialysis and freeze drying were conducted as in Example 19.

Based on this NMR analysis, the polymer contained 62 mol % repeat units resulting from SVS, 35 mol % repeat units resulting from MVPP and 3 mol % repeat units resulting from methyl vinyl phosphonic acid. The water content was calculated to 10.3% on a weight basis. The total recovery of monomers in the post dialysis polymer was calculated to be 65% on a molar basis.

Example 22 HomoPolymerization of Vinyl Phosphono-monoPhosphate

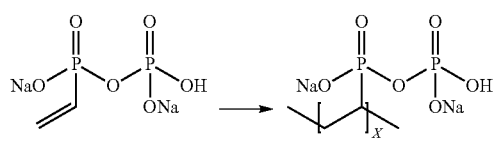

VPP (Example 1, 16.4 mmoles) water, 6 mL, and sodium bicarbonate (0.69 g, 8.2 mmoles) were charged in a 25 mL

TABLE 2

| % Total Monomer SVS Loaded | % Total Monomer VPP Loaded | % APS Loaded | % Sulfonate in Polymer | % Phosphono-Phosphate in Polymer | % Phosphonate in Polymer | Total Molar Yield | Mn (kDa) | Mw (kDa) |
|---|---|---|---|---|---|---|---|---|
| 74.9% | 25.1% | 5.0% | 81% | 15% | 4% | 75% | — | — |
| 75.0% | 25.0% | 5.0% | 79% | 20% | 1% | 79% | — | — |
| 65.0% | 35.0% | 5.0% | 67% | 30% | 3% | 55% | — | — |
| 56.0% | 44.0% | 5.0% | 62% | 35% | 3% | 63% | — | — |
| 55.2% | 44.8% | 5.5% | 66% | 30% | 3% | 77% | — | — |
| 50.0% | 50.0% | 5.2% | 59% | 40% | 2% | 65% | 2.8 | 5.5 |
| 45.0% | 55.0% | 5.0% | 56% | 42% | 2% | 58% | — | — | round bottom flask which was then purged with nitrogen for 15 minutes. Ammonium Persulfate (APS, 186.6 mg) was dissolved in 0.50 mL water and added to the mixture. The resulting solution was allowed to stir 6 hours at 60° C. At this time, NMR showed 25% polymerization monomer. An additional 186.6 mg of APS in 0.50 mL of water was added. The resultant was allowed to stir for a total of 24 hours at 60° C. NMR showed no remaining monomer.

The crude reaction solution was diluted with 500 mL in water with a resulting pH of 8.7. This solution were dialyzed with 2K molecular weight cut off dialysis membranes against reverse osmosis water with an adjusted pH of 8.5.

The resultant solution was stripped of water under vacuum to yield white to cream color solids which was further dried in a vacuum oven overnight to yield 2.8 g of solid. P-NMR showed only VPP with no VPA. The resultant was 91% polymer on a weight basis with the remaining water and impurities. The total recovery of monomers in the post dialysis polymer was calculated to be 58% on a molar basis.

Example 23 Co-Polymerization of Vinyl Phosphono-monoPhosphate (VPP) and Sodium 2-Acrylamido-2-Methyl Propane Sulfonic Acid (AMPS)

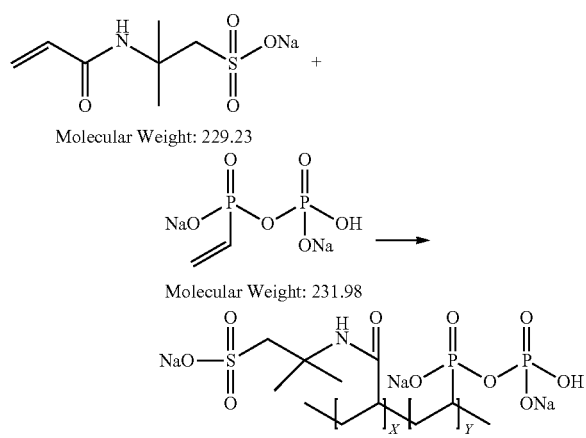

VPP (Example 1, 6.55 mmoles) and water 2 mL were charged in a round bottom flask, and the headspace of the flask purged with flowing nitrogen for 15 minutes. The flask was sealed and heated to 60° C. for 15 minutes to yield a homogenous solution. Ammonium Persulfate (APS, 149.3 mg) was dissolved in 1.2 g water. Every 30 minutes, 0.1 mL of the APS solution and 0.206 mL of AMPS (3 g of 50% solution, 6.55 mmoles) was added to the reaction over a total of 6 hours. The resultant was stirred 24 hrs at 60° C.

The crude reaction solution was diluted with 250 mL of water and dialyzed with 2K molecular weight cut off dialysis membranes against reverse osmosis water for 6 days.

Water was removed from the product by freeze drying yielding 2.66 g white solid.

The phosphonate content in the polymers were determined by preparing an NMR sample with purified polymer & trimethyl phosphate (TMP) in $D_2O$. The $^1H$ & $^{31}P$-NMR's were run from which the phosphonate content was calculated from the H and P peaks of the internal standard relative (TMP) relative to the polymer peaks and water. The P-NMR shows broad phosphono-phosponate peaks at ~18 to 23 ppm and −6 to −10 ppm in approximately 1:1 ratio and also a phosphonate peak at ~26-28 ppm. Based on the $^{31}P$-NMR areas at 18-23 and 26-28 ppm, the phosphono-phosphonate:phosphonate ratio is 98:2. Based on this analysis, the polymer contained 64.2 mol % repeat units resulting from AMPS, 35.1 mol % repeat units resulting from VPP and 0.7 mol % repeat units resulting from VPA. The water content was calculated to 13.3% on a weight basis.

Example 24 Co-Polymerization of Vinyl Phosphono-monoPhosphate (VPP) and 3-Sulfopropyl Acrylate Potassium Salt (SPA)

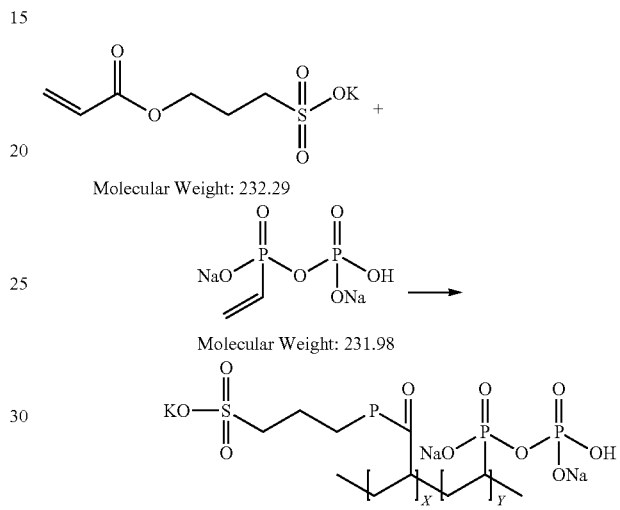

The procedure of example 23 was followed with the substitution of SPA (Aldrich) for AMPS. Freeze drying of product yielded 2.04 g white solid.

Based on NMR analysis, the polymer contained 62 mol % repeat units resulting from SPA, 36 mol % repeat units resulting from VPP and 2 mol % repeat units resulting from VPA. The water content was calculated to 15.5% on a weight basis.

Example 25 Co-Polymerization of VPP with Acrylamide

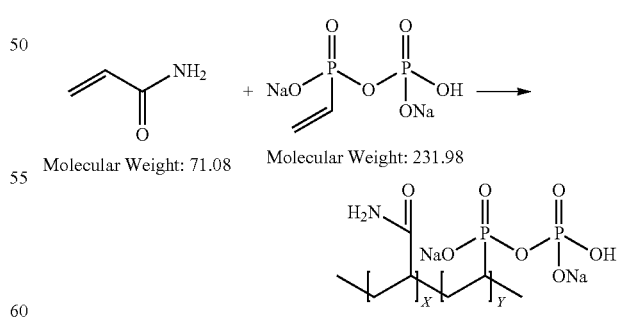

VPP (Example 1, 9.9 mmoles) and water, 3 mL, were charged in a round bottom flask, and the headspace of the flask purged with flowing nitrogen for 15 minutes. The flask was sealed and heated to 60° C. for 15 minutes to yield a homogenous solution. Ammonium Persulfate (APS, 225.9 mg) was dissolved in 1.2 g water. Acrylamide (Aldrich, 9.9 mmoles) was dissolved in 1.5 g water Every 30 minutes, 0.1 mL of the APS solution and 0.125 mL of the acrylamide solution was added to the reaction over a total of 6 hours. The resultant was stirred 24 hrs at 60° C. Progress was monitored by NMR.

The crude reaction solution was diluted with 250 mL of water and dialyzed with 2K molecular weight cut off dialysis membranes against reverse osmosis water for 5 days.

Water was removed from the product by freeze drying yielding 2.85 g white solid.

The phosphonate content in the polymers were determined by preparing an NMR sample with purified polymer & trimethyl phosphate (TMP) in $D_2O$. The $^1H$ & $^{31}P$-NMR's were run from which the phosphonate content was calculated from the H and P peaks of the internal standard relative (TMP) relative to the polymer peaks and water. The P-NMR shows broad phosphono-phosphonate peaks at ~18 to 23 ppm and −6 to −10 ppm in approximately 1:1 ratio. No phosphonate peak was observed at ~26-28 ppm. Based on this analysis, the polymer contained 53 mol % repeat units resulting from acrylamide, 47 mol % repeat units resulting from VPP. The water content was calculated to 16% on a weight basis.

Example 26 Co-Polymerization of VPP with VSMS

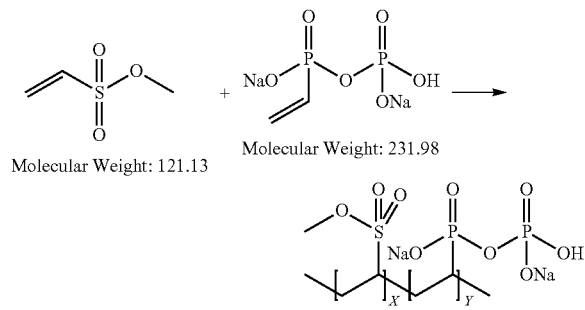

VPP (Example 1, 7.67 mmoles), bicarbonate (Aldrich 11.5 mmol) and water, 5 mL, were charged in a round bottom flask, and the headspace of the flask purged with flowing nitrogen for 15 minutes. The flask was sealed and heated to 60° C. for 15 minutes to yield a homogeneous solution. Ammonium Persulfate (APS, 174.9 mg) was dissolved in 1.2 g water. Every 15 minutes, 0.1 mL of the APS solution and 0.084 mL of VSME (Vinyl sulfonate methyl ester (Example 14, 79.8% Active, 7.67 mmole total) was added to the reaction over a total of 3 hours. The resultant was stirred an additional 3 hrs at 60° C. The crude reaction solution was diluted with 250 mL of water and dialyzed with 2K molecular weight cut off dialysis membranes against reverse osmosis water at a pH of 8.5 for 5 days.

Water was removed from the product by freeze drying yielding 2.05 g white solid.

The phosphonate content in the polymers were determined by preparing an NMR sample with purified polymer & trimethyl phosphate (TMP) in $D_2O$. The $^1H$ & $^{31}P$-NMR's were run from which the phosphonate content was calculated from the H and P peaks of the internal standard relative (TMP) relative to the polymer peaks and water. The P-NMR shows broad phosphono-phosphonate peaks at ~18 to 23 ppm and −4 to −10 ppm in approximately 1:1.1 ratio but no phosphonate peak at ~26-28 ppm. The total phosphorous content was 40.8%. The methyl proton from MSME was visible in the $^1H$ NMR and allowed quantification of VSME hydrolysis. Based on the total analysis, the polymer contained 39 mol % repeat units resulting from VSME, 20 mole % VSA, and 41 mol % repeat units resulting from VPP. The resultant was 73% polymer on a weight basis with the remaining water and impurities.

Example 27 Co-Polymerization of (Phosphono-monoPhosphate Ethyl) (Butyl) Acrylamide with AMPS

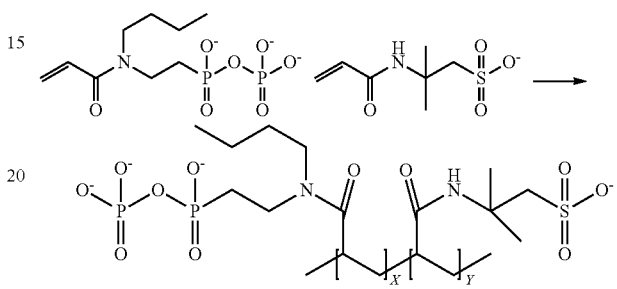

(Phosphono-monoPhosphate Ethyl) (Butyl) Acrylamide (Example 4, 21.6 mmoles) and AMPS (23.6 mmoles) were polymerized as in Example 23. The crude reaction solutions were dialyzed with 1K molecular weight cut off dialysis membranes against reverse osmosis water overnight, followed by 2 hours dilation against 0.5 M NaCl and then 1 hr against 0.05M NaCl. After freeze drying, 11.5 grams of material was collected. NMR as in other examples found the polymer to be approximately 67 mol % repeat units resulting from AMPS, and 33% from (Phosphono-monoPhosphate Ethyl) (Butyl) Acrylamide. The solid containing around 16% water, by weight and was 55% polymer by weight.

Example 28 Co-Polymerization of VPP with VPA

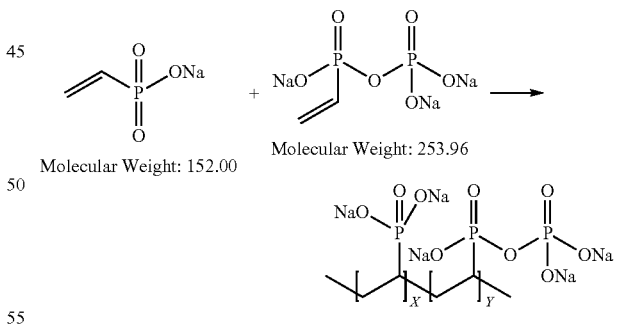

VPA (1.2 g, 11.1 mmoles) and water 6 mL were charged in a 25 mL round bottom flask. Sodium bicarbonate (2.8 g, 33.3 mmoles) was added over 60 minutes and the flask was then purged with nitrogen left to stir over night at room temperature. VPP (Example 1, 11.1 mmoles) was added and the solution purged with nitrogen and heated to 60° C. yielding a turbid solution. Ammonium Persulfate (APS, 253.5 mg) was dissolved in 0.75 mL water and added to the mixture. The resulting solution was allowed to stir 6 hours at 60° C. At this time, NMR showed 40% polymerization of all monomers. An additional 253.3 mg of APS in 0.75 mL of water was added. The resultant was allowed to stir for a total of 24 hours at 60° C. NMR showed 10% remaining monomer.

The crude reaction solution was diluted with 500 mL in water with a resulting pH of 8.7. This solution were dialyzed with 2K molecular weight cut off dialysis membranes against reverse osmosis water with an adjusted pH of 8.5.

The resultant solution was stripped of water under vacuum to yield white to cream color solids which was further dried in a vacuum oven overnight to yield 2.66 g of solid. P-NMR showed the ratio of VPP:VPA to be 61:39 in the polymer. The resultant was 88% polymer on a weight basis.

Example 29 Co-Polymerization of VPP with Methyl Acrylate

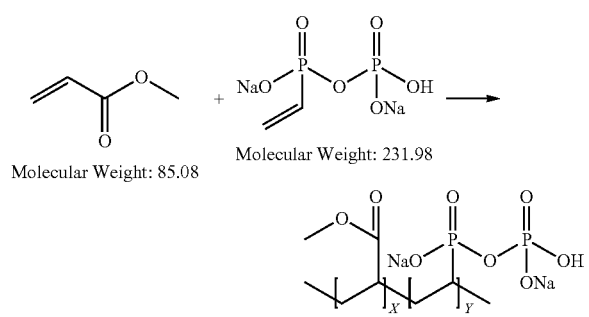

VPP (Example 1, 9.9 mmoles) and water, 4 mL, were charged in a round bottom flask, and the headspace of the flask purged with flowing nitrogen for 15 minutes. The flask was sealed and heated to 60° C. for 15 minutes to yield a homogeneous solution. Ammonium Persulfate (APS, 225.7 mg) was dissolved in 1.2 g water. Every 30 minutes, 0.1 mL of the APS solution and 0.073 mL Methyl Acrylate (Aldrich, 9.9 mmoles, 0.88 mL total) solution was added to the reaction over a total of 6 hours. At 3 hours a milky white color began to form. The resultant was stirred 24 hours at 60° C. yielding a milky white solution. Progress was monitored by NMR and showed 20% remaining VPP at 24 hours and no remaining methyl acrylate.

The reaction solution was added to 20 mL of additional water and 5 mL of MeOH was then added over 5 minutes under rapid stirring. Resultant was allowed to sit at room temperature for 10 minutes yielding a white precipitate. The precipitate was filtered and the MeCOH was removed from the filtrate.

The filtrate was diluted with 250 mL of water and dialyzed with 2K molecular weight cut off dialysis membranes against reverse osmosis water for 5 days at a pH of approximately 6.5.

Water was removed from the product by freeze drying yielding 1.4 g white solid.

The phosphonate content in the polymers were determined by preparing an NMR sample with purified polymer & trimethyl phosphate (TMP) in $D_2O$. The $^1H$ & $^{31}P$-NMR's were run from which the phosphonate content was calculated from the H and P peaks of the internal standard (TMP) relative to the polymer peaks and water. Analysis showed the resulting polymer to be 29% methyl acrylate, 16% Acrylate, 50% VPP, and 5% vinyl phosphonate. The resulting solid was 77% polymer on a weight basis.

Example 30 Co-Polymerization of (4-VinylBenzyl) Phosphono-monoPhosphate with SVS

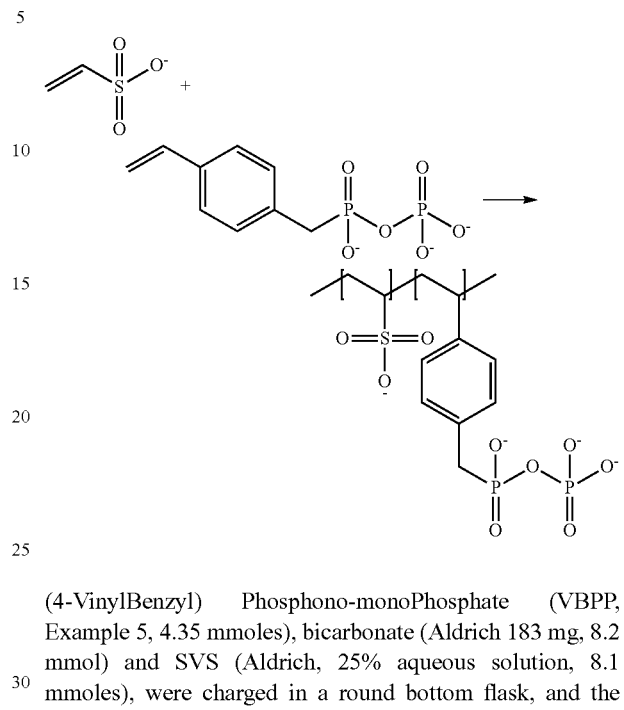

(4-VinylBenzyl) Phosphono-monoPhosphate (VBPP, Example 5, 4.35 mmoles), bicarbonate (Aldrich 183 mg, 8.2 mmol) and SVS (Aldrich, 25% aqueous solution, 8.1 mmoles), were charged in a round bottom flask, and the headspace of the flask purged with flowing nitrogen for 15 minutes. The flask was sealed and heated to 60° C. at which time a gas was evolved. Additional bicarbonate (total of 300 mg) was incrementally added until no additional off gassing was observed. Ammonium Persulfate (APS, Aldrich, 284 mg, 10% relative to total monomers) was added in 0.5 ml water. The resultant was stirred 24 hrs at 60° C.

$^1H$-NMR & $^{31}P$-NMR were run on the crude reaction solutions. The polymer composition approximately 25/75 SVS/VBPP.

The crude reaction solution was diluted with 500 mL water and the pH adjusted to 8.5 with 1 N NaOH. This solution was dialyzed with 2K molecular weight cut off dialysis membranes against reverse osmosis water for 6 days. Water was removed from the product by freeze drying yielding 1.85 g white solid.

The phosphonate content in the polymers were determined by preparing an NMR sample with purified polymer & trimethyl phosphate (TMP) in $D_2O$. The $^1H$ & $^{31}P$-NMR's were run from which the phosphonate content was calculated from the H and P peaks of the internal standard (TMP) relative to the polymer peaks and water. The P-NMR shows broad phosphono-phosponate peaks at ~13 to 15 ppm and −5 to −7 ppm in approximately 1:1 ratio and also a phosphonate peak at ~21-23 ppm. Based on the $^{31}P$-NMR areas at 13-15 and 21-23 ppm, the phosphono-phosphonate:phosphonate ratio is 93:7. Based on this analysis, the polymer contained 30 mol % repeat units resulting from SVS, 65 mol % repeat units resulting from VBPP and 5 mol % repeat units resulting from (4-VinylBenzyl)Phosphonate. The water content was calculated to 18% on a weight basis.

Example 31 Co-Polymerization of (Phosphono-monoPhosphate Ethyl)-Acrylamide with SVS

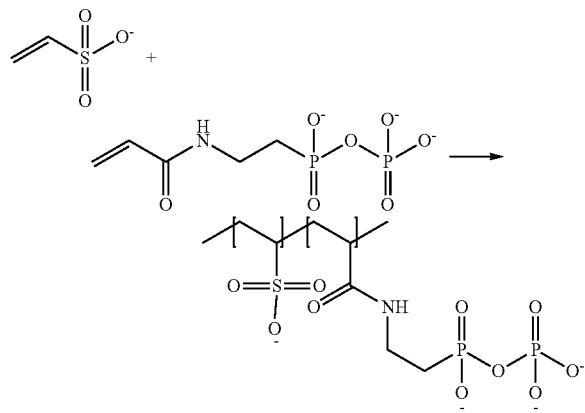

SVS, (Aldrich, 25% aqueous solution, 4.73 mmoles), was charged in a round bottom flask, and the headspace of the flask purged with flowing nitrogen for 15 minutes. The flask was sealed and heated to 60° C. Ammonium Persulfate (APS, Aldrich, 141 mg, 5% relative to total monomers) was added in 1.0 g water. Phosphono-monoPhosphate(Ethyl)-Acrylamide (Example 9, 4.95 mmoles) was added to 5.25 g water. To the flask with SVS, 0.1 mL APS solution and 1.0 mL (Phosphono-monoPhosphate Ethyl)-Acrylamide was added every 20 minutes for 3 hours. The resultant was stirred and additional 4 hours at 60° C.

The crude reaction solution was diluted with 500 mL water and the pH adjusted to 8.5 with 1 N NaOH. This solution was dialyzed with 2K molecular weight cut off dialysis membranes against reverse osmosis water for 6 days. Water was removed from the product by freeze drying yielding 3.4 g tan solid. H-NMR & P-NMR were run on the crude reaction solutions. The polymer composition is approximately 62:36:2 SVS:(Phosphono-monoPhosphate Ethyl)-Acrylamide:(Phosphonate Ethyl)-Acrylamide.

Example 32 Post Polymerization Modification of Co-Polymer of VPA and AA

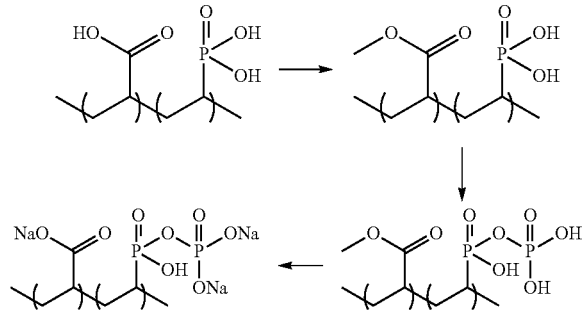

The polymer from example 18 was esterified by refluxing 2.3 grams in 150 mL of MeOH in a 250 mL 1 neck round bottom flask equipped with a heater and magnetic stirring. After 1 hour of refluxing, a short path distillation head was added and approximately ⅓ of the MeOH was removed. This MeOH was then replace with fresh anhydrous MeOH a total of 4 times. This procedure yielded about 47% conversion to the methyl ester of acrylic repeat units. Next, 2 drops of concentrated sulfuric acid were added and the solution was refluxed for 48 hours. This procedure increased the total methyl ester content to 83% by H NMR. In addition, around 9% of the phosphonate esters were converted to mono-methyl phosphonate esters by P NMR.

A magnetically stirred dry 50 ml 1 neck round bottom flask was charged with the methyl ester containing polymer (0.5, 1.63 mmole P) and 15 ml DMF under nitrogen. The resulting mixture was stirred overnight at room temperature yielding a swelled ball of polymer. Next, tributylamine (0.78 mL, 2.0 equivalents relative to P monomer) was added and stirred overnight at room temperature yielding a homogeneous solution. CDI (330 mg, 1.25 equivalents relative to P monomer) and 5 mL DMF were premixed and added to solution. The resulting mixture was stirred overnight yielding a homogeneous solution.

$H_3PO_4$ (479 mg, 3 equivalents), tributylamine (1.26 mL 3.5 equivalent) and 5 mL of DMF were mixed and sonicated then added to the polymer containing solution. Resultant was stirred overnight at room temperature. Resulting solution was stripped of solvent under vacuum (9 Torr) to a final temperature of approximately 60° C.

The resultant was dissolved in 50 ml of 1 N NaOH yielding a solution at pH 13.15 and stirred overnight. Resultant was stripped of water with flowing dry nitrogen to yield a white paste. The paste was dissolved in 60 mL of MeOH over 1 hour and the resulting solid collected and dried to 2.52 grams.

The crude solid was dissolved in water, pH adjusted to 9 and resulting solution dialyzed as described in previous examples. 0.67 g of white fluffy solid was collected after lyophilization. P NMR showed around 20% yield of phosphono-monophosphate groups from initial phosphonate groups.

Example 33 Co-Polymerization of (Phosphono-monoPhosphate Ethyl)-Methacrylate with SVS

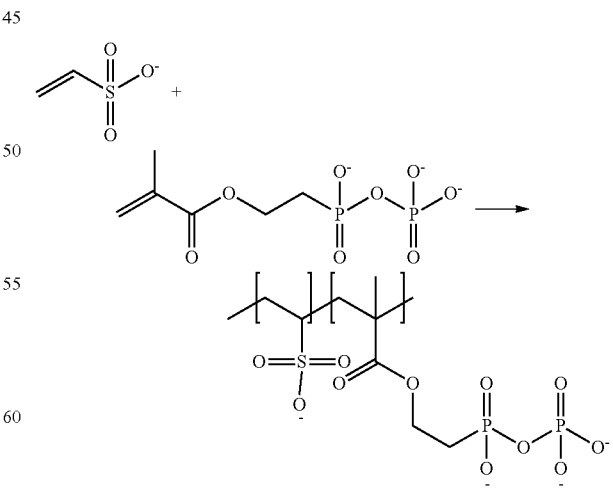

The procedure of example 31 was followed using 5.7 mmoles of SVS, and 3.79 mmoles of (Phosphono-mono-Phosphate Ethyl)-Methacrylate from Example 7. After freeze drying, 1.5 g white solid was collected at 86% polymer, 14% water/inactives. The polymer composition approximately 63:35:2 SVS:(Phosphono-monoPhosphate Ethyl)-Methacrylate:(Phosphonate Ethyl)-Methacrylate.

Example 34 Co-Polymerization of (Propyl Phosphono-monoPhosphate)-Methacrylate with SVS

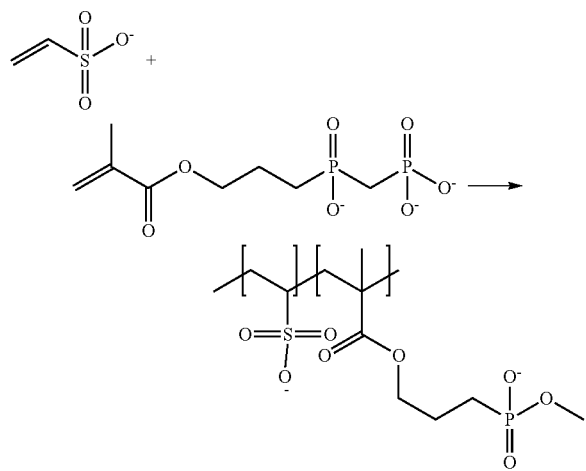

The procedure of example 31 was followed using 3.7 mmoles of SVS, and 3.5 mmoles of (Propyl Phosphono-monoPhosphate)-Methacrylate from Example 8. After freeze drying, 1.84 g white solid was collected at 86% polymer, 14% water/inactives. The polymer composition approximately 56:44 VSA:(Propyl Phosphono-monoPhosphate)-Methacrylate.

Example 35 Post Polymerization Modification of Homopolymer of VPA

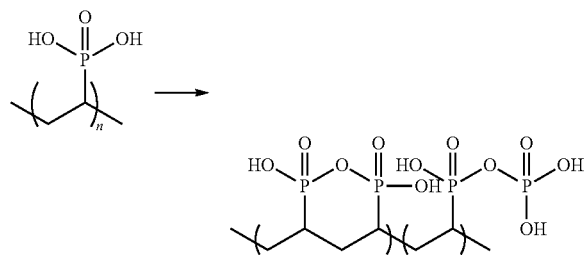

Poly(vinylphosphonic acid) (500 mg) was added to a 100 ml round bottom flask followed by methanol (20 ml). Tributylamine (1.1 mL) was added to the mixture and stirred for 30 minutes and the mixture became homogeneous. Resultanting solution was concentrated under vacuum followed by the addition of pyridine (10 mL) and removal under vacuum three times. Resulting solid was dissolved in 10 mL pyridine. Diphenyl phosphoryl chloride (956 µL, 1 equivalent) was slowly added however, a precipitate formed in the reaction mixture so it was diluted with additional pyridine (50 ml). After 1 hour mono(tributylamine) phosphate was added (3.3 mL, 3 equivalents) and this was stirred overnight.

Solvent was removed under vacuum and the resulting solid was dissolved in water and dialyzed. After dialysis the water was removed via freeze drying to yield a sticky solid. PNMR analysis indicated 87.7% of the phosphonates had for an anhydride with an adjacent phosphonate, while 12.3% were phosphono-monophosphate.

Example 36 Post Polymerization Modification of Poly Methyl-VinylPhosphonate

Following a similar procedure to Example 32 a magnetically stirred dry round bottom flask is charged with poly methyl-vinyl phosphonate, DMF and purged with nitrogen. Next, tributylamine (2.0 equivalents relative to P monomer) is added and stirred overnight at room temperature yielding a homogeneous solution. CDI (1.25 equivalents relative to P monomer) and DMF are premixed and added to solution which is stirred overnight. $H_3PO_4$ (3 equivalents), tributylamine (3.5 equivalent) and DMF are mixed and sonicated then added to the polymer containing solution. Resultant is stirred overnight at room temperature. Resulting solution is stripped of solvent under vacuum (9 Torr) to a final temperature of approximately 60° C. to yield a phosphono-phosphate containing polymer.

Example 37 Post Polymerization Modification of Random Phosphonate Containing Polymer Phosphonated polyethylene is synthesized by following the description of Anbar (M. Anbar, G. A. St. John and A. C Scott, J Dent Res Vol 53, No 4, pp 867-878, 1974) or Schroeder and Sopchak (J, P. Schroeder and W. P. Sopchak, Journal of Polymer Science Volume 47 Issue 149 p 417 (1960)). Briefly 10 g polyethylene is reacted in a dry flask with 200 g of $PCl_3$ at reflux until the polymer dissolves. Next dry oxygen is flowed through the dissolved solution. Resulting solution is distilled to reduce the overall volume by half and is poured over ice chips to create phosphonated polyethylene. This phosphonated polyethylene is reacted following the procedure of Example 36.

Example 38 Post Polymerization Modification of Poly(Vinylbenzylphosphonic Acid) Containing Polymer Poly(vinylbenzylphosphonic acid) is synthesized by polymerizing (4-VinylBenzyl) Phosphonic Acid using either heat in methanol as described by Anbar et al. or by using an initiator such as ammonium persulfate at 5-10% loading relative to monomer. The resulting polymer is reacted following the procedure of Example 36.

Example 39 Synthesis of a Phosphono Phosphate Monomer and Polymer on a Side Chain

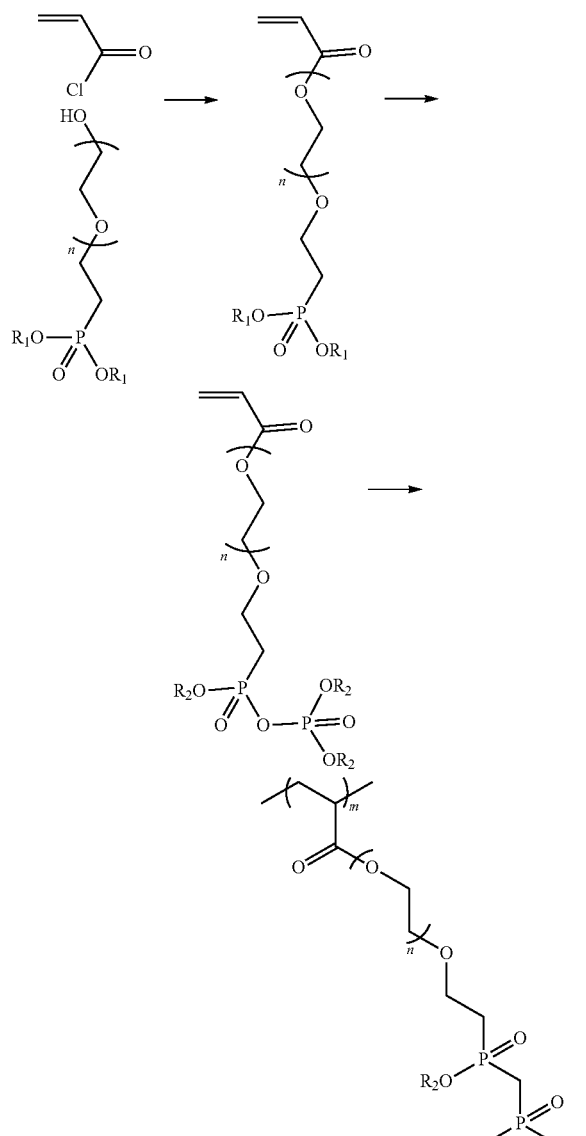

m > n
R$_1$ = H, Salts, Alkyl
R$_2$ = H, Salts, P(O)(OR$_2$)$_2$

The procedure of Example 12 is followed substituting an ethylene glycol dimer, trimer, tetramer or polymer with a primary hydroxy group such as diethyl (2-hydroxyethoxy) ethoxy)ethyl)phosphonate for dimethyl (2-hydroxyethyl) phosphonate. Ethyl phosphonate terminated ethylene glycol units can be synthesized by following the procedure of Brunet et al. (Ernesto Brunet,* Man´a Jose´ de la Mata, Hussein M. H. Alhendawi, Carlos Cerro, Marina Alonso, Olga Juanes, and Juan Carlos Rodri´guez-Ubis Chem. Mater. 2005, 17, 1424-1433). Briefly, the desired ethylene glycol dimer, trimer, tetramer or polymer (1 equivalent) is added over 2-4 days to a 90° C. mixture of Cs$_2$CO$_3$ (1.2 equivalents) diethylvinylphosphonic acid (12.5 equivalents). Purification is performed by extracting with water dichloromethane followed by flash chromatography. Polymerization of the phosphono-phosphate containing monomer is performed as described in Example 22 to yield a homopolymer or with co-monomers as described in Examples 19, 20, 23, 24, 25, or 26 to yield co-polymers.

Example 40 Synthesis of a Phosphono Phosphate Polymer on a Side Chain by Post-Polymerization Modification

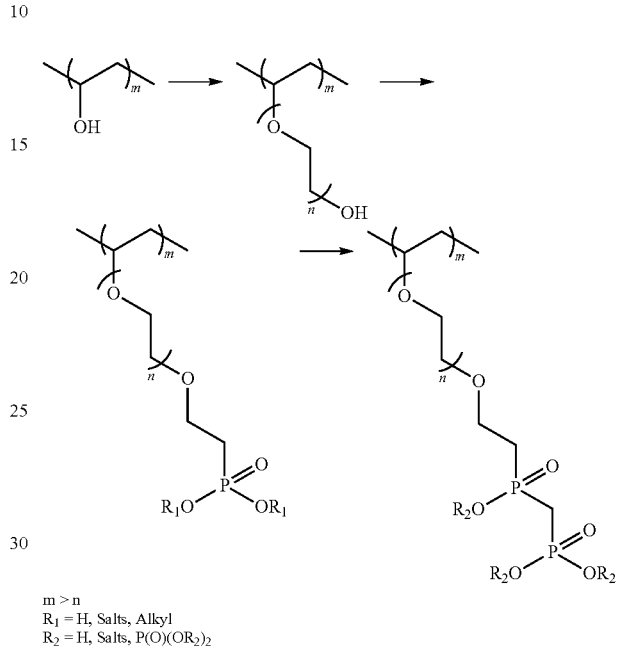

m > n
R$_1$ = H, Salts, Alkyl
R$_2$ = H, Salts, P(O)(OR$_2$)$_2$

Ethoxylated polyvinyl alcohol is reacted as described in Example 38 to create a phosphonate terminated ethoxylated polyvinyl alcohol polymer. Ethoxylated polyvinyl alcohol is synthesized by reacting polyvinyl alcohol in a sealed reactor at a temperature of 85-120° C. and a pressure of 20-200 psig with a base catalyst such as methoxide or sodium hydroxide and ethylene oxide added slowly over several hours. This phosphonate terminated polymer is reacted as described in Example 36 to create a phosphono-phosphate containing polymer where the phosphono-phosphate is attached to a side chain of the polymer by post-polymerization modification.

Example 41 Co-Polymerization of Di-Methyl Vinyl Phosphonate (DMVP) with SVS

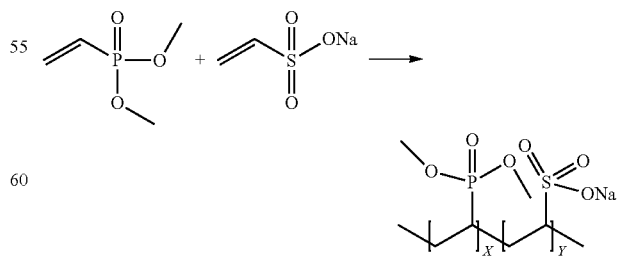

SVS (Aldrich, 25% aqueous solution, 11.0 mmoles) was charged in a round bottom flask, and the headspace of the flask purged with flowing nitrogen for 15 minutes. The flask was sealed and heated to 60° C. for 15 minutes. Ammonium Persulfate (APS, 225 mg) was added in 1.0 g water. Every 30 minutes, 0.1 mL of the APS solution and 0.1 mL of DMVP (Aldrich, 1.5 g, 1.3 mL, 11.0 mmoles) were added to the reaction over a total of 6 hours. The resultant was stirred 24 hrs at 60° C.

The crude reaction solution was diluted with 250 mL of water and dialyzed with 2K molecular weight cut off dialysis membranes against reverse osmosis water for 4 days. The initial pH of the dialysis water was 5.8 but dropped to 2.5.

Water was removed from the product by freeze drying yielding 2.4 g white solid.

Based on NMR analysis the polymer contained 56.9 mol % repeat units resulting from SVS, 43.1 mol % DMVP. The water content was calculated to 10.4% on a weight basis.

Example 42 Co-Polymerization of Example 23 Co-Polymerization of (Ethyl Phosphono-monoPhosphate)-Vinyl Ether and (AMPS)

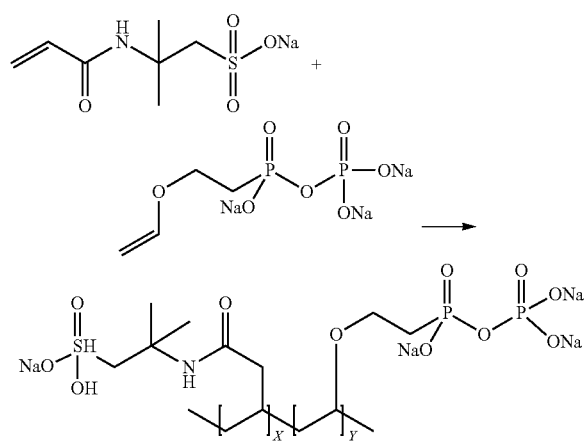

(Ethyl Phosphono-monoPhosphate)-Vinyl Ether (Example 11, 4.7 mmoles), water 5 mL, and AMPS (4 g of 50% solution, 8.7 mmoles) were charged in a round bottom flask, and the headspace of the flask purged with flowing nitrogen for 15 minutes. The flask was sealed and heated to 60° C. for 15 minutes to yield a homogenous solution. Ammonium Persulfate (APS, 306 mg) was dissolved in 1.1 g water. Every 30 minutes, 0.1 mL of the APS solution was added to the reaction over a total of 4 hours. The resultant was stirred 4 hours at 60° C.

The crude reaction solution was diluted with 750 mL of water and dialyzed with 2K molecular weight cut off dialysis membranes against reverse osmosis water for 8 days.

Water was removed from the product by freeze drying yielding 2.12 g tan solid.

Based on NMR analysis, the polymer contained 90.8 mol % repeat units resulting from AMPS, 9.2 mol % repeat units resulting from (Ethyl Phosphono-monoPhosphate)-Vinyl Ether. The solid was found to contain 77% water by weight.

Example 43 PSPM on VPA SVS Co Polymers

The polymers from Example 17 were tested according the PSPM model along with homopolymers of Poly Vinyl Sulfonate and Poly Vinyl phosphonate purchased from PolySciences Inc. Results are shown in FIG. 1 and Table 3 (below) along with pyrophosphate and polyphosphate.

TABLE 3

| Source/Name | % S | % P | Delta L |
| --- | --- | --- | --- |
| PolyScience | 100% | 0% | 16.3 |
| Example 17 | 80% | 20% | 8.7 |
| Example 17 | 69% | 31% | 9.0 |
| Example 17 | 57% | 43% | 6.0 |
| Example 17 | 56% | 44% | 6.7 |
| Example 17 | 44% | 56% | 9.3 |
| Example 17 | 34% | 66% | 12.9 |
| PolyScience | 0% | 100% | 15.8 |
| Pyrophosphate | | | 16.3 |
| Polyphosphate | | | 2.0 |

Example 44 PSRM on VPA SVS Co Polymers

Figure 2:
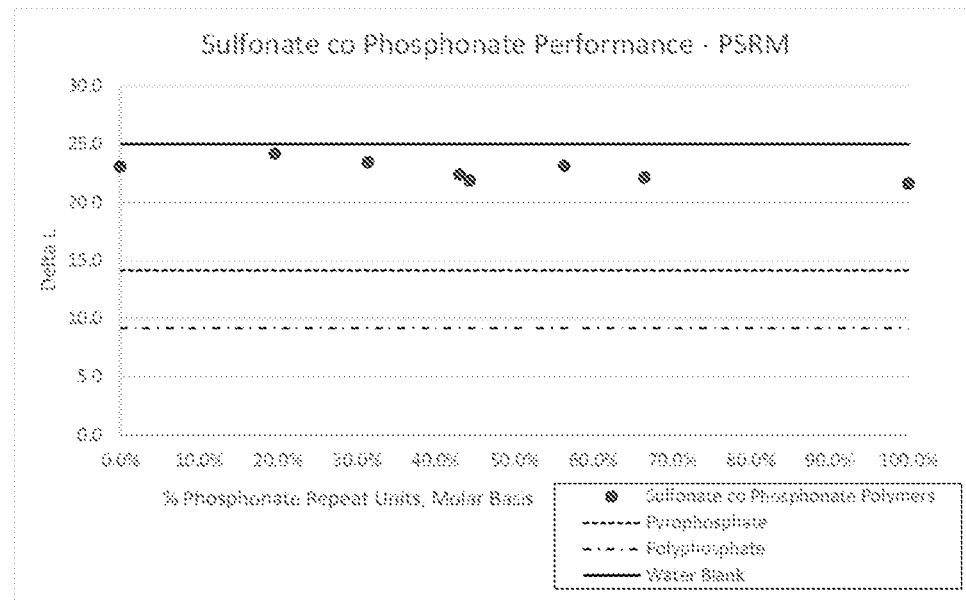
FIG. 2 is a chart showing polymer performance.

The polymers from Example 17 were tested according the PSRM model along with homopolymers of Poly Vinyl Sulfonate and Poly Vinyl phosphonate purchased from PolySciences Inc. Results are shown in FIG. 2 and Table 4 (below) along with pyrophosphate, polyphosphate and the water treatment.

TABLE 4

| Source/Name | % Sulfonate in Polymer | % Phosphonate in Polymer | Delta L |
| --- | --- | --- | --- |
| PolyScience | 100.0% | 0% | 23.1 |
| Example 17 | 80% | 20% | 24.2 |
| Example 17 | 69% | 31% | 23.5 |
| Example 17 | 57% | 43% | 22.4 |
| Example 17 | 56% | 44% | 21.9 |
| Example 17 | 44% | 56% | 23.2 |
| Example 17 | 34% | 66% | 22.2 |
| PolyScience | 0.0% | 100% | 21.6 |
| Pyrophosphate | | | 14.2 |
| Polyphosphate | | | 9.2 |
| Water Blank | | | 25.0 |

Example 45 PSPM on VPP SVS Co Polymers

Figure 3:
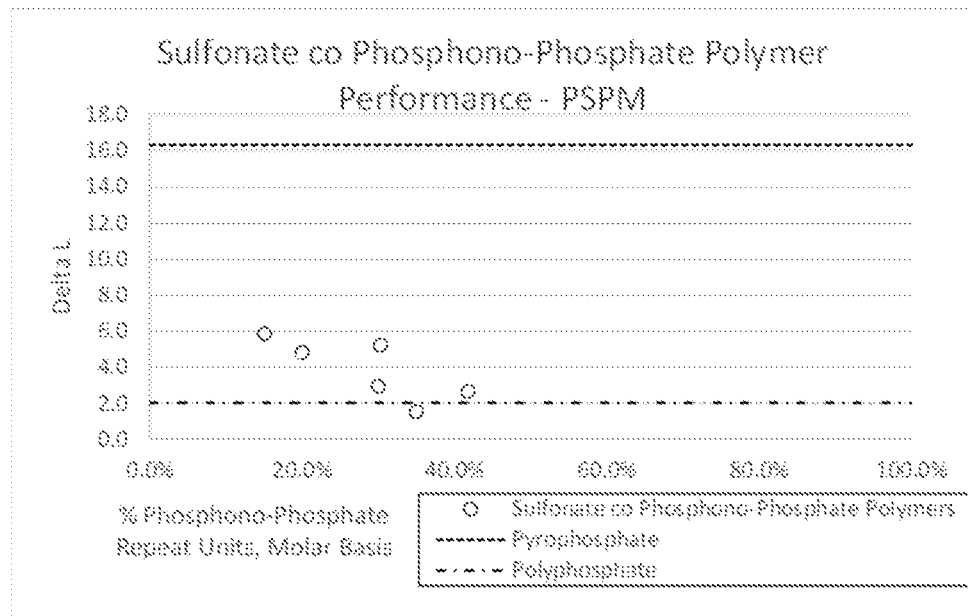
FIG. 3 is a chart showing polymer performance.

The polymers from example 20 were tested according the PSPM model. Results are shown in FIG. 3 and Table 5 (below) along with pyrophosphate and polyphosphate.

TABLE 5

| Source/Name | % Sulfonate in Polymer | % Phosphonate in Polymer | % Phosphono-Phosphonate in Polymer | Delta L |
| --- | --- | --- | --- | --- |
| Example 20 | 81% | 4% | 15% | 5.9 |
| Example 20 | 79% | 1% | 20% | 4.8 |
| Example 20 | 67% | 3% | 30% | 3.0 |
| Example 20 | 62% | 3% | 35% | 1.6 |
| Example 20 | 66% | 3% | 30% | 5.2 |
| Example 20 | 56% | 2% | 42% | 2.7 |
| Pyrophosphate | | | | 16.3 |
| Polyphosphate | | | | 2.0 |

Example 46 PSRM on VPP SVS Co Polymers

Figure 4:
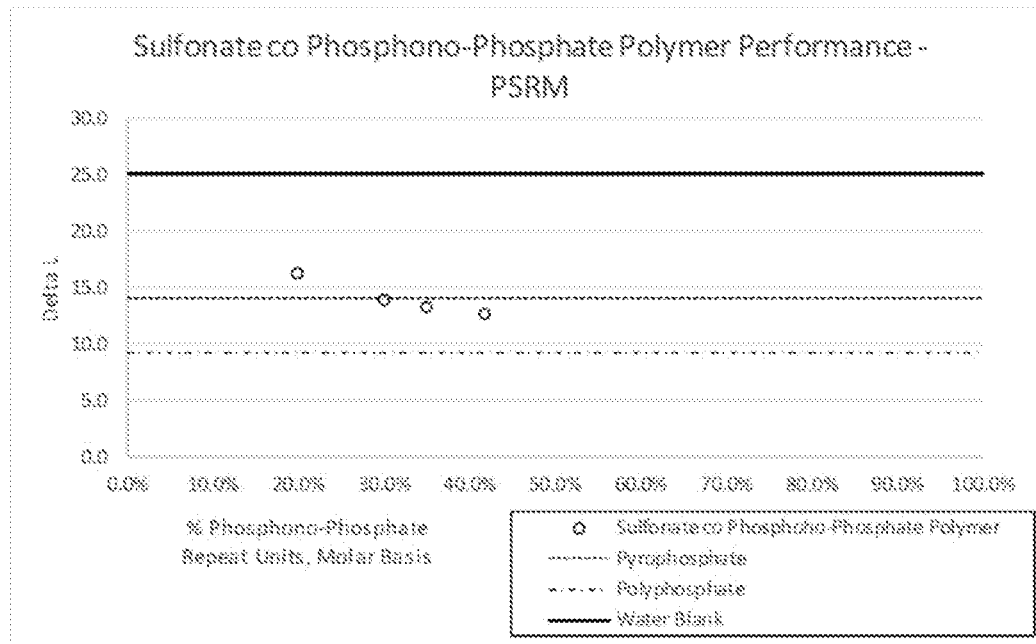
FIG. 4 is a chart showing polymer performance.

The polymers from example 20 were tested according the PSRM model. Results are shown in FIG. 4 and Table 6 (below) along with pyrophosphate, polyphosphate and the water treatment.

TABLE 6

| Source/Name | % Sulfonate in Polymer | % Phosphonate in Polymer | % Phosphono-Phosphonate in Polymer | Delta L |
|---|---|---|---|---|
| Example 20 | 79% | 1% | 20% | 16.2 |
| Example 20 | 67% | 3% | 30% | 13.9 |
| Example 20 | 62% | 3% | 35% | 13.3 |
| Example 20 | 56% | 2% | 42% | 12.6 |

TABLE 6-continued

| Source/Name | % Sulfonate in Polymer | % Phosphonate in Polymer | % Phosphono-Phosphonate in Polymer | Delta L |
|---|---|---|---|---|
| Pyrophosphate | | | | 14.2 |
| Polyphosphate | | | | 9.2 |
| Water Blank | | | | 25.0 |

Example 47 PSRM and PSPM on Mixed Co Polymers

The polymers from previous examples as noted below were tested according the PSRM and PSPM models. Results are shown in Table 7 below along with pyrophosphate, polyphosphate and the water treatment.

| Compound | Structure | PSRM | PSPM |
|---|---|---|---|
| Ex. 29 | 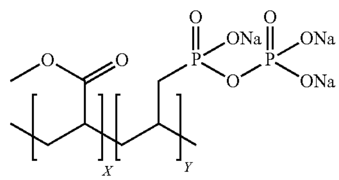 | 11.0 | 10.5 |
| Ex. 22 | 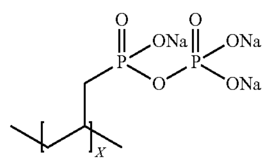 | 10.9 | 8.0 |
| Ex. 28 | 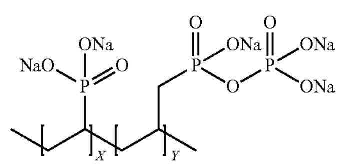 | 12.9 | 7.1 |
| Ex. 30 | 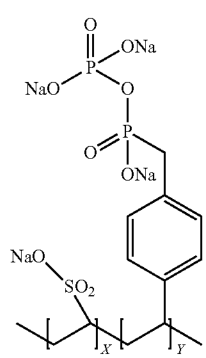 | 17.1 | 22.9 |

-continued

| Compound | Structure | PSRM | PSPM |
|---|---|---|---|
| Ex. 6 | 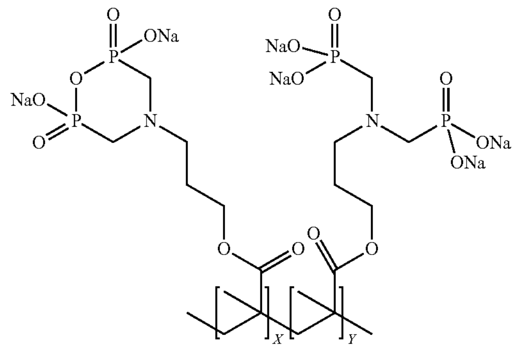 | 20.7 | 29.8 |
| Ex. 31 | 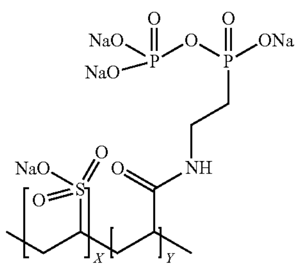 | 17.8 | 17.1 |
| Ex. 33 | 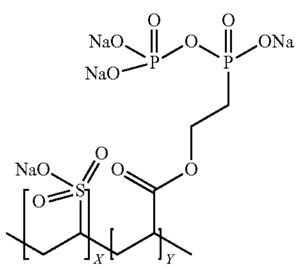 | 16.3 | 17.4 |
| Ex. 23 | 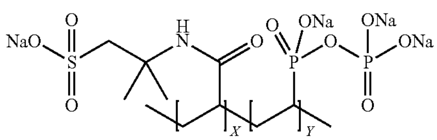 | 13.3 | 10.1 |
| Ex. 41 | 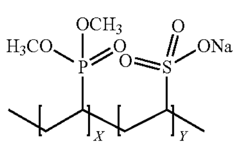 | 24.7 | 16.4 |
| Ex. 24 | 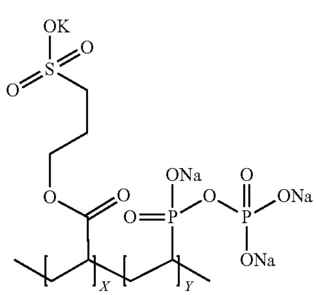 | 11.7 | 9.2 |
| Ex. 21 | 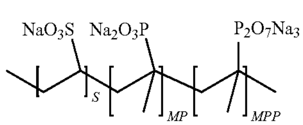 | 18.0 | 5.8 |

| Compound | Structure | PSRM | PSPM |
|---|---|---|---|
| Ex. 25 | 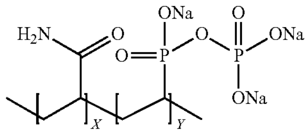 | 12.9 | 11.6 |
| Ex. 26 | 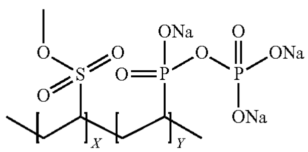 | 15.8 | 8.9 |
| Ex. 42 | 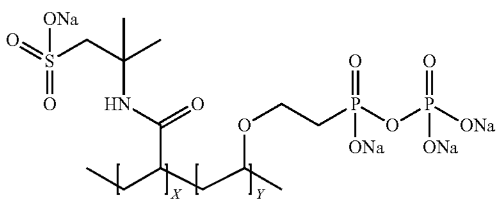 | 15.8 | 19.2 |
| Ex. 27 | 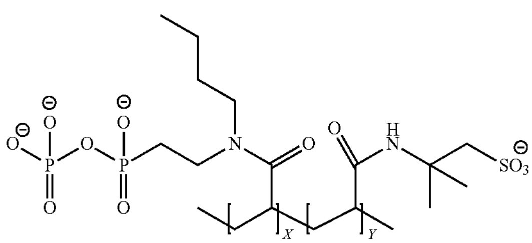 | 21.2 | 18.3 |
| Ex. 34 | 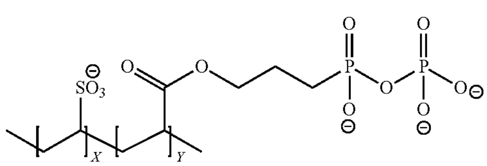 | 6.4 | 11.7 |
| Water Control | — | 26.8-30.0 | 25.0-29.0 |
| 2% Pyro | — | 13.0-18 | 12.2-16.0 |
| 2% GlassH | — | 3.5-11.0 | 3.0-8.6 |
| HAP blank | — | 0.0 | 0.0 |

General Chemical Scheme for Examples 48-52—Synthesis of Vinyl Phosphono-monoPhosphate (VPP) or [Vinylphosphonic Phosphoric Anhydride] and Other Extended Vinyl Phosphono-Phosphates (eVPP) by Removal of Water The following chemical scheme shows general reaction scheme in examples 48-52 used to form the primary desired products, VPP and VPPP, along with some of the other products observed in some but not all of the following experiments. Please refer to individual examples for final identified product distributions.

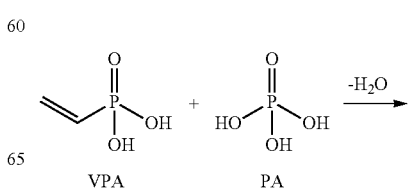

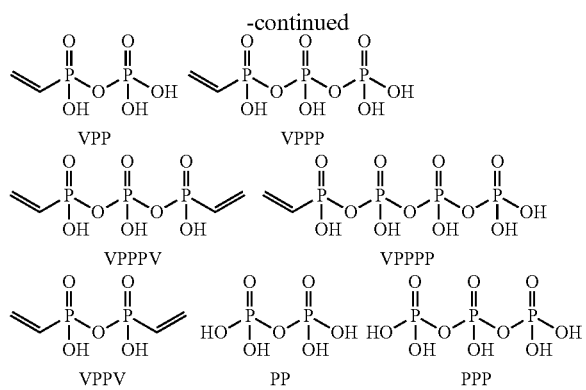

Example 48—Synthesis of VPP and eVPP by Evaporation Using a Sweep Gas with 3 Equivalents of PA A 50 mL 3 neck round bottom flask, equipped with a magnetic stirrer and a short path distillation head in the middle neck, was charged with 1 gram of vinyl phosphonic acid (VPA) and 2.72 g (3 equivalents) of 99% phosphoric acid (PA). One side neck was stoppered, and nitrogen was swept through the other side neck and out through the distillation head. The flask was placed in oil bath heated to 105° C. and stirred at that temperature for 27 hours. Samples (~1 drop) were removed at desired time points, dissolved in 1 mL D7-DMF with 0.25 mL tributyl amine, and evaluated by P-NMR. The final product was found to contain VPA, Vinyl-Phosphono-monoPhosphate (VPP), Vinyl-Phosphono-Pyrophosphate (VPPP), Vinyl-Phosphonic Acid Anhydride (VPPV), Phosphoric acid (PA), Pyrophosphoric Acid (PP) & Tri-Phosphoric Acid (PPP). Species identification was confirmed using LCMS. In addition H-NMR was run on the final 27 hour sample from which it was determined that no polymerization occurred during the reaction.

Final molar distributions of all vinyl containing species in the melt at 27 hours was found to be 43% VPA, 38% VPP, 9% VPPP, and 10% VPPV.

Example 49—Synthesis of VPP and eVPP by Evaporation Using Vacuum and a Sweep Gas with 3 Equivalents of PA The procedure of example 48 was followed with the following changes. The short path distillation head was connected to a Buchi vacuum pump rather than venting to atmosphere. The round bottom flask was evacuated to 50-60 Torr for the duration of the experiment with constant flow of nitrogen from one side neck. Sampling at 32 and 48 hours showed little change between the time points with a vinyl containing distribution of 31-32% VPA, 40-41% VPP, 14% VPPP, and 13-14% VPPV. Signals corresponding to VPPPV were also observed in P-NMR but were not quantified do to overlap with other peaks.

Example 50—Synthesis of VPP and eVPP by Evaporation Using Vacuum and a Sweep Gas with 6 Equivalents of PA The procedure of example 49 was followed with 6 equivalents of PA relative to VPA. The distribution of vinyl containing species at 72 hours was 31% VPA, 40% VPP, 21% VPPP, and 8% VPPV. Signals corresponding to VPPPV were also observed in P-NMR but were not quantified do to overlap with other peaks.

Example 51—Synthesis of VPP and eVPP by Reaction with Phosphorous Anhydride ($P_2O_5$, Phosphorous Pentoxide)

To a magnetically stirred 20 mL scintillation vial was added 2.24 g of 85 weight % phosphoric acid in water, 1.01 g 90% vinyl phosphonic acid and 2.5 phosphorous pentoxide (in that order). The molar ratio of vinyl phosphonate to total phosphate (calculated as the sum of the moles of phosphate plus twice the moles of $P_2O$) as 6. The vial was heated to 175° C. and sampled for P NMR at 1 hour using the procedure of example X. The molar composition of identified vinyl containing species was 34% VPA, 41% VPP, 19% VPPP and 5% VPPV. Additional vinyl peaks were visible in P NMR that likely correspond to larger species including VPPPP, and VPPPPP. LCMS confirmed the existence of higher order phosphono-phosphates with peaks for VPP, VPPP, VPPPP, VPPPPP, VPPPPPP, and VPPPPPPP all visible in negative ion mode.

Example 52—Scale Up and Purification of Example 49

The procedure of example 49 was followed with a 5-fold increase in total materials. Sampling at 32 hours showed a distribution of vinyl containing species of 35% VPA, 37% VPP, 12% VPPP, 12% VPPV and 4% VPPPV.

After cooling, the bulk of the crude reaction mixture was dissolved in 40 ml anhydrous DMF. The dissolved solution was added to a solution of 28.1 g triethyl amine (1.5 equivalents based on total starting acid) in 100 mL of anhydrous DMF with rapid stirring over 5 min. The P-NMR was run on the resultant solution and was consistent with distributions from the crude reaction mixture.

The resultant solution was stripped of DMF at 70° C. & 25 Torr yielding 38.4 g viscous yellow oil. This was dissolved in 100 mL $H_2O$ yielding a solution with a pH of 2.5, which was adjusted to 11.0 with 110 g 10% NaOH yielding a clear solution. The P-NMR was run on the resultant solution which showed a consistent product distribution as previous samples, but with an approximate 20% reduction in VPPV. Upon standing at room temperature for 1 hour, a white precipitant formed which was collected by filtration, dried overnight in ambient air to 4.65 g This precipitant was found to be about 90% pyrophosphate, with 4% phosphate and less than 3% each of VPA, VPP and PPP. The filtrate was stripped of solvent yielding 49.4 g clear viscous oil. The pH of the resultant oil was checked by litmus and found to be around 7. This was brought up to approximately 125 g with additional water yielding a pH of 7.5 which was adjusted to 11.0 with 15.2 g 1N NaOH. To this pH 11 solution was added 250 ml MeOH with rapid stirring over 30 min. at room temperature. A white precipitant formed over the course of one hour. This precipitant was collected by filtration, rinsed one time with 50 mL 2:3 H2O:MeOH and dried under ambient air overnight to 17.9 g. This precipitant was found to be approximately 43% pyrophosphate, 39% phosphoric acid, 10% PPP, 3% VPP and 4% VPPP. The MeOH water solution was concentrated under flowing nitrogen overnight at room temperature to yield 31.1 g of viscous oil. The oil was found to have a molar phosphorous distribution of approximately 33% VPA, 33% VPP, 8% VPPP, 11% PA, 10% VPPV and 3% VPPPV. The oil was also found to have residual water and DMF.

To the oil, 300 ml MeOH was added over 1 hr at room temperature yielding a white precipitant which was collected by filtration, rinsed 1×50 mL MeOH and dried under vacuum at room temperature for 2 hrs to yield 4.3 g white powder. The powder was found to have a molar phosphorous distribution of 49% VPP, 26% PA, 6% PP, 15% VPPP and 3% VPA. The MeOH solution was concentrated under flowing nitrogen at room temperature 7.0 g white paste. The composition of the white paste was found to be approximately 73% VPA, 23% VPP and 5% VPPPV.

Example 53—Polymerization to Create VPPP Containing Polymer and Testing with PSPM and PSRM The white powder from example 52 containing 49% VPP, 26% PA, 6% PP, 15% VPPP and 3% VPA, was polymerized following the procedure of Example 19 and 20 using a 50/50 mixture (total molar vinyl basis) of the white VPPP containing powder (8.6 mmol vinyl groups) and SVS (8.6 mmol vinyl groups). After dialysis and freeze drying, 3.6 g of polymer was collected and found to contain 57% monomers based on SVS, and 43% based on phosphonates. The phosphonate distribution was 3% from VPA, 78% from VPP and 18% from VPPP. The polymer was 78% active on a weight basis with 22% impurities/water. This polymer was tested in the PSPM and PSRM models with values of $\Delta L$ of 5.5 and 11.0 respectively. The controls for the PSPM were: Water 28.0, HAP Blank 0.0, Pyrophosphate 18.0, Polyphosphate 4.0, and the controls for the PSRM were: Water 24.2, HAP Blank 0.0, Pyrophosphate 12.4 Polyphosphate 8.6.

Examples 54-57—Scale up and Testing in Oral Care Formulations

The following examples demonstrate formulation of the polymers containing phosphono-phosphates into a dentrifice and subsequent testing in the stain models.

Example 54—20-30 g Scale Up of Example 19 and 20

The procedure of examples 19 and 20 was scaled up using 96.7 mmoles of VPP and 96.7 mmoles of VSA with an equivalent increase of other reagents and solvents. After dialysis and freeze drying, 27.1 g of polymer was collected and found to contain 59% monomers based on SVS, 40% based on VPP and 2% based on VPA. The polymer was 83% active on a weight basis with 17% impurities/water.

This polymer was tested in the PSPM and PSRM models with values of $\Delta L$ of 6.8 and 13.0 respectively. The controls for the PSPM were: Water 28.0, HAP Blank 0.0, Pyrophosphate 14.3, Polyphosphate 3.1, and the controls for the PSRM were: Water 25.0, HAP Blank 0.0, Pyrophosphate 13.5, Polyphosphate 10.7.

Example 55—20-30 g Scale Up of Example 16 and 17

The procedure of examples 16 and 17 was scaled up using 148 mmoles of VPP and 122 mmoles of VSA with an equivalent increase of other reagents and solvents. After dialysis and freeze drying, 26.8 g of polymer was collected and found to contain 54% monomers based on SVS, 46% based on VPA. The polymer was 90% active on a weight basis with 10% impurities/water. This polymer was tested in the PSPM and PSRM models with values of $\Delta L$ of 10.2 and 20.2 respectively. The controls for the PSPM were: Water 28.0, HAP Blank 0.0, Pyrophosphate 14.3, Polyphosphate 3.1, and the controls for the PSRM were: Water 25.0, HAP Blank 0.0, Pyrophosphate 13.5, Polyphosphate 10.7.

Example 56—100 g Scale up of Example 19 and 20

The procedure of examples 19 and 20 was scaled up using 354.5 mmoles of VPP and 433 mmoles of VSA with an equivalent increase of other reagents and solvents. After neutralization the bulk solution was brought up to 9819 g with water and pH adjusted to 10 with 1N NaOH. Low MW impurities were reduced in the resultant solution by Tangential Flow Filtration (TFF) using Tami Industries 1000 MWCO column (E190613N001). The solution was pumped from a reservoir through the column and back into the reservoir. The effluent that passed through the pores of the column was collected in a flask on a balance. In the first run, the solution was pumped until 3.5 kg of effluent was collected. The remaining solution in the reservoir was then brought back up to around 9 kg. The procedure was repeated with 4.8 kg removed and the reservoir brought up to 11 kg. In the final run, 6 kg of effluent was removed. After the final TFF the concentrated solution was filtered thru a 0.22 μm filter (Stericup 500 ml Filter Unit, Aldrich).

The water was removed from the final TFF concentrate after filtering by evaporation under flowing nitrogen for for 5 days at room temperature yielding 173 g tan paste. This was further dried under vacuum at >1 Torr for 48 hours yielding 137.2 g light tan solid. The solid was found to contain 66% monomers based on SVS, 34% based on VPP. The polymer was 80% active on a weight basis with 20% impurities/water. This polymer was tested in the PSPM and PSRM models with values of $\Delta L$ of 6.5 and 11.5 respectively. The controls for the PSPM were: Water 28.0, HAP Blank 0.0, Pyrophosphate 18.0, Polyphosphate 4.0, and the controls for the PSRM were: Water 24.2, HAP Blank 0.0, Pyrophosphate 12.4 Polyphosphate 8.6.

Example 57—Formulation and Testing of Examples 54-56

All percentages in this example are by weight unless otherwise noted.

The compositions were prepared as follows:

Composition #1 was commercially purchased Crest Cavity Protection Regular Flavor.

Composition #2 was commercially purchased Crest Pro-Health Clean Mint Smooth Formula.

Composition #3 is the same as Composition #2 with the addition of Polymer Example 54.

Composition #2 was weighed into a Speedmix jar. The polymer Example 54 was then added to the Speedmix jar and mixed in a Speedmixer until homogeneous. The pH was then determined with a pH electrode and 2N HCl was added and mixed in a Speedmixer to adjust the pH to a target of ~6.

Composition #4 is the same as Composition #2 with the addition of Polymer Example 55. Composition #2 was weighed into a Speedmix jar. The polymer Example 55 was then added to the Speedmix jar and mixed in a Speedmixer until homogeneous. The pH was then determined with a pH electrode and 50% NaOH solution was added and mixed in a Speedmixer to adjust the pH to a target of ~6.

Composition #5 was prepared in a pilot scale mixer by adding approximately half of the sorbitol to the mixer, heating to 65° C. with a heating/cooling jacket on the tank and pulling vacuum. In a separate container 1 weight percent of the silica and all the hydroxyethyl cellulose were dry blended until homogeneous and then drawn by vacuum into the mixing vessel. A both an anchor agitator and high shear rotor/stator device were used to mix and homogenize the mixture to assure homogeneity and hydration of the hydroxyethyl cellulose. Once homogeneous, the rotor/stator device was turned off. The remaining sorbitol, about 25% of the water and all the blue dye were added and mixed until homogeneous using the anchor agitator. In a separate container, 1 weight percent of the silica, all the saccharin and all the carrageenan were dry blended and drawn into the main mix vessel under vacuum with the high shear rotor/stator device and anchor agitator running. Once homogenous, the rotor/stator was turned off. Next the remaining silica was drawn into the main mix vessel under vacuum and mixed using the achor agitator at a vacuum not less than 26 inches of mercury. The batch was then cooled to approximately 49° C. via the heating/cooling jacket while continuing to be mixed with the anchor agitator. Once the batch reached 49° C., the achor agitator was stopped, the mixer was opened and the flavor and sodium lauryl sulfate solution were added to the top of the batch. Vacuum was then pulled to 24 inches of mercury and the anchor agitator and rotor/stator were turned on until the batch was homogeneously mixed. After mixing, the rotor/stator was turned off and vacuum was pulled to 27 inches of mercury to remove air. In a separate container, the remaining 75% of the water was heated to 65 C. Sodium gluconate was added to the water and mixed until dissolved. Stannous fluoride was then added to the gluconate solution and mixed until dissolved. Stannous chloride was then added to the gluconate solution and mixed until dissolved. Once this solution was prepared, it was added under vacuum to the main mix vessel and mixed using the anchor agitator until homogeneous. After the mixing, the sodium hydroxide was added under vacuum to the main mix vessel and the anchor agitator and rotor/stator were used to mix homogeneously. Once homogeneous, the rotor/stator was turned off and the heating/cooling jacket was reduced to 30° C. and vacuum was pulled to 26 inches of mercury. The batch was mixed under vacuum until the temperature reached 35° C., it was pumped out of the main mix vessel.

Composition #6 is the same as Composition #5 with the addition of Polymer Example 56. Composition #5 was weighed into a Speedmix jar. The polymer Example 56 was then added to the Speedmix jar and mixed in a Speedmixer until homogeneous. The pH was then determined with a pH electrode and no further adjustment was needed to achieve a pH of ~6.

Composition #7 is the same as Composition #2 with the addition of Polymer Example 56. Composition #2 was weighed into a Speedmix jar. The polymer Example 56 was then added to the Speedmix jar and mixed in a Speedmixer until homogeneous. The pH was then determined with a pH electrode and 50% NaOH solution was added and mixed in a Speedmixer to adjust the pH to a target of ~6.

| | Composition #1 iPTSM Negative Control | Composition #2 Formula #1 Nil Polymer | Composition #3 Formula #1 w/ Example 54 | Composition #4 Formula #1 w/ Example 55 | Composition #5 Formula #2 Nil Polymer (iPTSM Positive Control) | Composition #6 Formula #2 w/ Example 56 | Composition #7 Formula #1 w/ Example 56 |
|---|---|---|---|---|---|---|---|
| H2O | 11.165 | 21.156 | 20.599 | 20.719 | 13 | 12.684 | 20.492 |
| NaF | 0.243 | | | | | | |
| SnF2 | | 0.454 | 0.442 | 0.445 | 0.454 | 0.443 | 0.44 |
| NaOH (50%) | | 0.87 | 0.847 | 0.881 | 0.8 | 0.781 | 0.843 |
| Sorbitol | 65.508 | 48 | 46.737 | 47.009 | 55.159 | 53.819 | 46.493 |
| Monosodium Phosphate dihydrate | 0.419 | | | | | | |
| Trisodium Phosphate Dodecahydrate | 1.1 | | | | | | |
| Carboxy Methyl Cellulose | 0.75 | | | | | | |
| Carbomer 956 | 0.3 | | | | | | |
| Z119 | 15 | 0.056 | 0.055 | 0.055 | 20 | 19.514 | 0.054 |
| Z109 | | 17.5 | 17.039 | 17.139 | 0 | 0 | 16.951 |
| TiO2 | 0.525 | 0.5 | 0.487 | 0.49 | 0.25 | 0.244 | 0.484 |
| Carrageenan | | 1.5 | 1.461 | 1.469 | 0.8 | 0.781 | 1.453 |
| Xanthan Gum | | 0.875 | 0.852 | 0.857 | 0 | 0 | 0.848 |
| Hydroxyethyl Cellulose | | 0 | | | 0.5 | 0.488 | 0 |
| Sodium Lauryl Sulfate (29% Sol'n) | 4 | 5.00 | 4.868 | 4.897 | 4 | 3.903 | 4.843 |
| Saccharin | 0.13 | 0.45 | 0.438 | 0.441 | 0.455 | 0.444 | 0.436 |
| Flavor | 0.81 | 1.30 | 1.266 | 1.273 | 1 | 0.976 | 1.259 |
| ZnCitrate | | 0.53 | 0.519 | 0.522 | 0 | 0 | 0.516 |
| NaGluconate | | 1.30 | 1.266 | 1.273 | 2.082 | 2.031 | 1.259 |
| SnCl2*2H2O | | 0.51 | 0.492 | 0.495 | 1.5 | 1.464 | 0.49 |

-continued

|  | Composition #1 iPTSM Negative Control | Composition #2 Formula #1 Nil Polymer | Composition #3 Formula #1 w/ Example 54 | Composition #4 Formula #1 w/ Example 55 | Composition #5 Formula #2 Nil Polymer (iPTSM Positive Control) | Composition #6 Formula #2 w/ Example 56 | Composition #7 Formula #1 w/ Example 56 |
|---|---|---|---|---|---|---|---|
| 2N HCl Dye Solution | 0.05 | 0.28 | 0.277 | 0 |  | 0 | 0.726 |
| Example 54 (VSA/VPP) |  | 2.35 | 2.355 | 0 |  | 0 | 0 |
| Example 55 (VSA/VPA) |  | 0 | 0 | 2.036 |  | 0 | 0 |
| Example 56 (VSA/VPP) |  |  |  | 0 |  | 2.43 | 2.412 |
| Total | 100 | 100 | 100 | 100 | 100 | 100 | 100 |
| PSPM (ΔL/ΔE) | 24.3/ 31.07 | 19.47/ 27.84 | 6.79/ 10.34 | 12.62/ 18.10 | 30.91/ 43.91 | 20.15/ 30.80 | 7.02/ 10.64 |
| PSRM (ΔL/ΔE) | 19.47/ 24.72 | 18.15/ 24.55 | 18.38/ 25.31 | 16.96/ 22.71 | 21.02/ 30.71 | 19.95/ 27.69 | 17.39/ 22.31 |
| iPTSM % Stain Potential | 0% | 3% | −41% | −49% | 100% | — | — |

Example 58—Synthesis of VPP and eVPP by reaction with Phosphoric Acid and Urea

For all samples in the example, the following general procedure was followed:

A scintillation vial was charged with VPA, 85% or 99% $H_3PO_4$, urea & water as noted in the Table 1 below. The resultant was stirred at 60° C. for approximately 15 minutes until a homogenous solution was obtained. The resultant solution was transferred hot into an 800 mL beaker. This was placed in a programmable lab oven with circulating air flow and exterior ventilation. All samples were heated as follows:
1) Ramped from room temperature to 110° C. over 15 minutes.
2) Hold at 110° C. 3 hours.
3) Ramped from 110° C. to 150° C. over 15 minutes.
4) Hold at 150° C. for either 15 or 60 minutes as noted in table below.
5) Cooled to room temperature and allow to stand overnight.

P-NMR was run on the crude reaction products (~50 mg reaction product in 1 mL $D_2O$ with 5 drops 30% NaOD). The products were found to contain VPA, vinyl-phosphono-phosphate (VPPA), vinyl-phosphono-pyrophosphate (VPPPA), vinylphosphonic anhydride (SM-An), phosphoric acid (PA), pyrophosphoric acid & tri-phosphoric acid (PPP). Areas from P-NMR are shown in Table 3 below. H-NMR's were also run on the reaction products to check for polymerization of the VPA during the heating. No polymer was observed.

TABLE 3

| | % Areas from P NMR | | | | | Sample Prep & Rx Conditions | | | | | | | |
|---|---|---|---|---|---|---|---|---|---|---|---|---|---|
| Rx # | VPA | VPPA | VPPPA | SM-An | VPPA + VPPPA | g VPA | g H2O | g H3PO4/% | g Urea | Equiv VPA | Equiv H3PO4 | Equiv Urea | Time 150 C. |
| 1 | 46.9 | 22.7 | 5.0 | 25.4 | 27.7 | 0.5 | 1.5 | 0.58 g 85% | 0.33 | 1 | 1.1 | 1.2 | 15 min |
| 1 | 48.9 | 29.5 | 7.1 | 14.4 | 36.6 | 0.5 | 1.5 | 1.16 g 85% | 0.66 | 1 | 2.2 | 2.4 | 15 min |
| 3 | 33.4 | 38.5 | 13.4 | 14.8 | 51.8 | 0.5 | 1.5 | 1.75 g 85% | 1 | 1 | 3.3 | 3.6 | 15 min |
| 4 | 36.4 | 40.2 | 15.7 | 7.6 | 56.0 | 0.5 | 1.5 | 3.48 g 85% | 2 | 1 | 6.6 | 7.2 | 15 min |
| 5 | 100.0 | 0.0 | 0.0 | 0.0 | 0.0 | 0.5 | 1.5 | 3.48 g 85% | 0 | 1 | 6.6 | 0 | 15 min |
| 6 | 33.1 | 38.1 | 19.2 | 9.6 | 57.3 | 0.5 | 0 | 2.95 g 99% | 2 | 1 | 6.6 | 7.2 | 15 min |
| 7 | 48.5 | 34.3 | 10.5 | 6.7 | 44.8 | 0.5 | 1.5 | 3.48 g 85% | 2 | 1 | 6.6 | 7.2 | 60 min |
| 8 | 45.8 | 36.2 | 11.1 | 6.9 | 47.3 | 0.5 | 0 | 3.48 g 85% | 2 | 1 | 6.6 | 7.2 | 60 min |
| 9 | 54.7 | 29.5 | 7.4 | 8.4 | 36.9 | 0.5 | 0 | 1.75 g 85% | 1 | 1 | 3.3 | 3.6 | 60 min |
| 10 | 54.1 | 32.1 | 8.3 | 5.5 | 40.4 | 0.5 | 0 | 2.95 g 99% | 2 | 1 | 6.6 | 7.2 | 60 min |
| 11 | 32.1 | 38.1 | 21.9 | 7.8 | 60.1 | 0.5 | 0 | 3.48 g 85% | 2 | 1 | 6.6 | 7.2 | 15 min |
| 12 | 41.7 | 32.4 | 14.0 | 11.9 | 46.4 | 0.5 | 0 | 1.75 g 85% | 1 | 1 | 3.3 | 3.6 | 15 min |
| 13 | 33.0 | 36.5 | 22.0 | 8.5 | 58.5 | 0.5 | 0 | 2.95 g 99% | 2 | 1 | 6.6 | 7.2 | 15 min |
| 14 | 40.2 | 29.6 | 17.0 | 13.2 | 46.6 | 0.5 | 0 | 3.48 g 85% | 4 | 1 | 6.6 | 14.4 | 15 min |
| 15 | 42.7 | 25.7 | 22.7 | 8.9 | 48.4 | 0.5 | 0 | 1.75 g 85% | 2 | 1 | 3.3 | 7.2 | 15 min |

Example 59—Synthesis of Polymer Containing VPP and eVPP by Reaction of Polymer with Phosphoric Acid and Urea

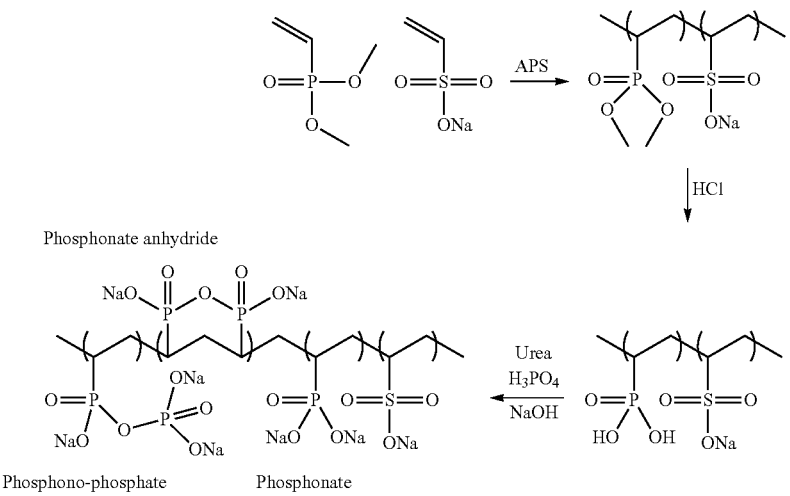

Phosphonate anhydride

Phosphono-phosphate    Phosphonate

Dimethyl vinyl phosphonate, DMVP (10.6 g, 77.9 mmoles) and sodium vinyl sulfonate solution, SVS (25% aqueous solution, 40.5 g, 77.9 mmoles), were charged in a 100 mL round bottom flask. The flask was purged with nitrogen for 15 minutes and heated to 60° C. Ammonium persulfate APS, 888 mg, 2.55% of total monomer, was brought up in 4 g of water and degassed with nitrogen for 5 minutes. The APS solution was added to the solution containing DMVP and SVS and resultant solution was allowed to stir for 24 hours under nitrogen at 60° C.

$^1$H-NMR & $^{31}$P-NMR were run on the crude reaction solution, and a monomer conversion of around 99% was observed with a broad P polymer peak at ~37 ppm from the phosphonate group.

The crude reaction solution was diluted to 10 wt % polymer in water with 207 g of water. To this was added 300 mL of acetone over 30 minutes under continuous stirring at room temperature to yield a turbid solution. After standing in a separatory funnel for 30 minutes a lower viscous polymer rich syrup and upper fluid organic layer were formed. The lower layer was collected, solvent evaporated under nitrogen overnight followed by vacuum, 2 hours at 1 Torr to yield 15.3 grams of a tacky tan solid. $^1$H-NMR & $^{31}$P-NMR were run on this solid with an internal standard, trimethyl phosphate, to show a 50:50 ratio of DMVP:SVS derived groups.

The tacky tan solid was mixed with 30 grams of water and 45 grams of concentrated HCl (≈37%) to yield a milky white solution. This mixture was refluxed for 48 hours to yield a transparent solution with a slight brown color. The water and HCl were stripped from the solution on a roto-vap operating at 60° C. and 20 torr to a total volume of ≈20 mL. 100 additional mL of water was added to this remaining fraction and the stripping was repeated, then 200 mL of water was added, the sample was frozen and lyophilized to yield 11.8 g of tan solid. $^{31}$P-NMR showed a shift in the polymer beak from ≈37 to ≈32 ppm, while the $^1$H-NMR showed the disappearance of the peak polymer peak at ≈3.8 ppm that corresponded to the methyl ester peak. Analysis with an internal standard indicated a ratio of P containing groups to sulfur containing groups of approximately 47 to 53, and a weight activity of 82.4%

A 100 mL beaker was charged with 4.85 grams of 85% phosphoric acid and 2.77 grams of urea and heated to 60° C. for 15 minutes then cooled to room temperature to yield a clear solution. 5 grams of 82.4% active polymer with a calculated ratio of P to S of 47 to 53 was dissolved in 15 mL of water and this was added to the phosphoric acid/urea mixture in the 100 mL beaker. This was placed in a programmable lab oven with circulating air flow and exterior ventilation and heated as follows:
1) Ramped from room temperature to 110° C. over 15 minutes.
2) Hold at 110° C. 3 hours.
3) Ramped from 110° C. to 150° C. over 15 minutes.
4) Hold at 150° C. for 15 minutes.
5) Cooled to room temperature and allow to stand overnight. 11.4 grams of spongy white product was collected. P-NMR was run on the crude reaction products (~150 mg reaction product in 1 mL D$_2$O with 2 drops 30% NaOD). P-NMR demonstrated a broad peak at ≈−5 ppm corresponding to a phosphono-phosphate group on a polymer chain. A portion of this peak is overlapped by pyrophosphate making quantification difficult.

The bulk of the crude, 11.4 g, was dissolved in 50 mL of water, charged to a round bottom flask under stirring and 50 mL of methanol added over 30 minutes to yield a turbid solution. Upon standing in a separatory funnel for 30 minutes, a lower viscous polymer rich syrup layer resulted which was separated (9.5 g). The ratio of polymer to phosphate to pyrophosphate was evaluated by P-NMR and found to be 161 to 43 to 113.

The precipitation was repeated on the above 9.5 grams of syrup using 50 mL of water and 50 mL of methanol. 2.13 g syrup resulted. P-NMR showed the polymer to phosphate to pyro ratio to be 158 to 3 to 18.

The resultant syrup was brought up to 250 mL of reverse osmosis (RO) water further purified by dialysis in a Thermo Scientific Slide-A-Lyzer dialysis flask (2K MWCO) against RO water (pH adjusted to 8.5 w sat sodium bicarbonate solution) for 6 days. The water was removed by freezing and lyophilization yielding 1.59 grams white solid. $^1$H-NMR & $^{31}$P-NMR showed the collected polymer to be ≈41% P monomers, and 59% S monomers. Analysis of the P containing groups showed ≈22% phosphono-phosphate groups with a small amount of phosphono-pyrophosphate groups. The remaining P containing groups appeared to be a mixture of phosphonate and phosphonate anhydride structures. The polymer was calculated as 87.4% weight active.

Example 60 Co-Polymerization of Vinyl Phosphono-monoPhosphate (VPP) and Sodium Vinyl Sulfonate (SVS) with Purification

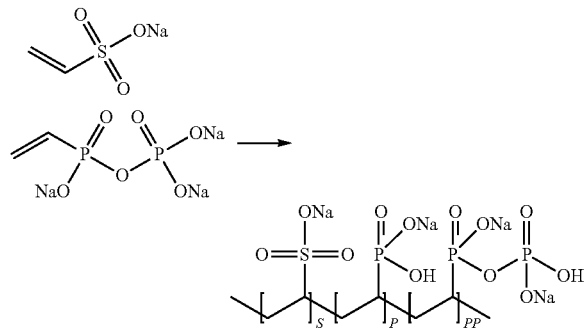

VPP (made on larger scale as described in Example 1, 64.6 g active, 254 mmoles) and SVS (25% aqueous solution, 161.6 g, 310 mmoles), initial molar ratio of SVS to VPP of 55 to 45, were charged in a 500 mL round bottom flask, stirred and the headspace of the flask purged with flowing nitrogen for 60 minutes. The pH of the solution was raised from 8.5 to 10.5 by addition of 9.5 mL of 1M NaOH. The flask purged with flowing nitrogen and heated to 60° C. at which time Ammonium Persulfate (APS, Aldrich, 7.73 mL of a 10% solution in water, mg, 0.6% relative to total monomers) was added. The resultant was stirred 24 hrs at 60° C.

$^1$H-NMR & $^{31}$P-NMR were run on the crude reaction solutions. Total monomer conversion of 78% was observed with broad P polymer peaks at ~18 to 23 ppm from the phosphonate group and −6 to −10 from the phosphate bound to the phosphonate group.

The polymer was purified by adding methanol aliquots over 15 minutes to a stirred solution containing 10% active polymer. A turbid solution resulted and was transferred to a separatory funnel and allowed to stand for an additional 15 minutes to fully separate into a lower viscous polymer rich syrup and an upper fluid layer. The lower polymer layer was collected and the upper layer reprecipitated using an additional aliquot of methanol and following repeating the same procedure. All samples were then dried under vacuum for two days with the final mass recorded in the Table 4 below.

TABLE 4

| Fraction | ml MeOH | Dried Mass |
|---|---|---|
| 1 | 150 | 38.6 |
| 2 | 100 | 11.0 |
| 3 | 50 | 6.4 |
| 4 | 50 | 3.1 |
| 5 | 100 | 4.2 |
| 6 | 150 | 4.0 |

Figure 5:
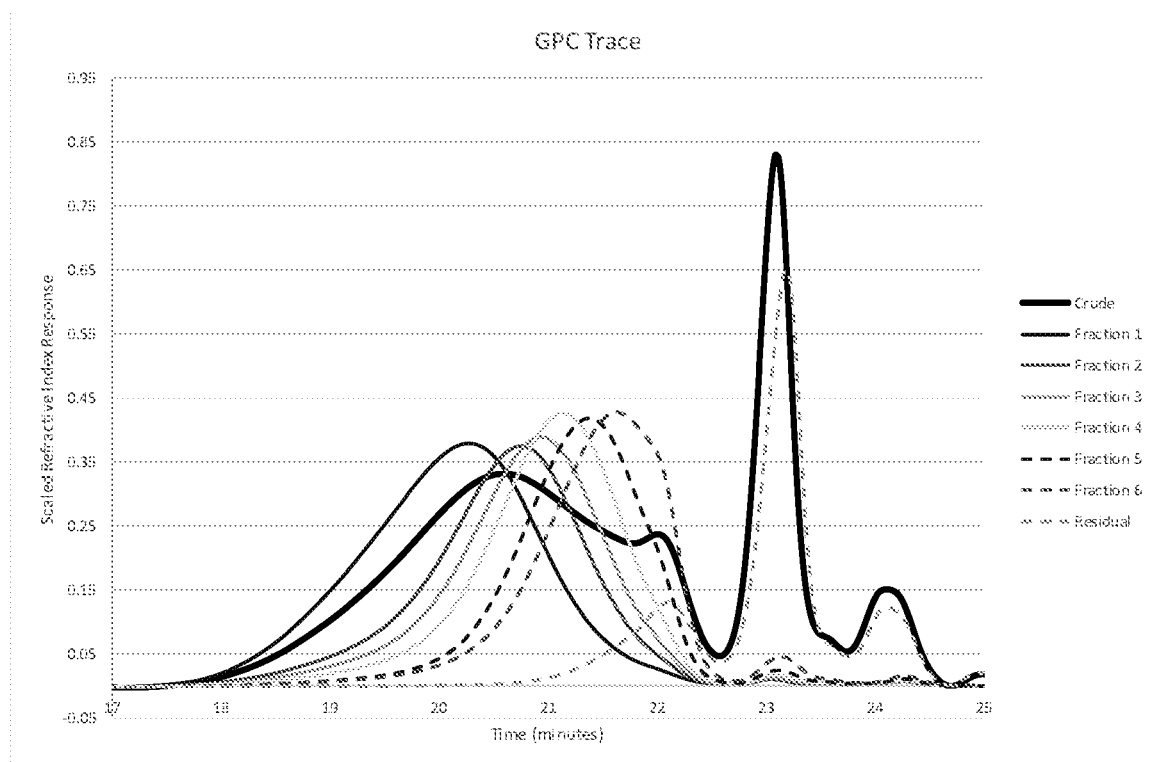
FIG. 5 is a GPC trace plot resulting from polymer analysis.

In addition, approximately 50 ml of the remaining upper H$_2$O/MeOH layer was concentrated under N$_2$ stream overnight at room temperature followed by drying for 24 hours under vacuum at room temperature yielding 2.5 g white solid. Size exclusion chromatography/gel permeation chromatography (SEC or GPC, 3-columns in series, Polymer Standards Service MCX1000A, MCX500A and MCX100A all 5 μm, with guard column, 0.2M NaNO$_3$ mobile phase 1 mL/min) showed sequential decreases in molecular weight from fraction 1 with the highest molecular weight and fraction 6 with the lowest. The GPC trace plot resulting from the polymer analysis is provided as FIG. 5. Higher molecular weight is represented by a shorter retention time, while lower molecular weight has a higher retention time. The large peaks after 22.5 minutes represent non polymer species such as residual monomers, and salt impurities in the sodium vinyl sulfate solution.

Example 61 Additional Purification of Vinyl Phosphono-monoPhosphate (VPP) and Sodium Vinyl Sulfonate (SVS) Samples from Example 60

Additional purification was performed on fractions 1-3 and 4-6. A 15 weight % polymer solution in water was created from the combined fractions 1-3. To this was added a mass of methanol equal to 20% of the mass of the entire water fraction of 60 minutes with stirring. Stirring was stopped and the solution phase separated to give a viscous polymer rich lower layer. This fraction was collected and dried. This procedure was repeated three additional times with an additional 10% methanol relative to the starting mass of solution added each time. All samples were oven dried with the percent of original mass recorded in the table below. Fractions 1-4 were 77-81% active with less than 0.5% phosphate, less than 0.2% vinyl phosphate or vinyl phosphono-phosphate, with no detectable vinyl sulfonate.

TABLE 5

| Fraction | % MeOH | % of Total |
|---|---|---|
| 1 | 20% | 73% |
| 2 | 30% | 14% |
| 3 | 40% | 5% |
| 4 | 50% | 4% |
| Residual |  | 4% |

A 20 weight percent polymer solution was created from the combined fractions 4-6. To this solution was added a mass of methanol equal to 60% of the total mass of the solution. The resulting precipitant was dried under vacuum for two days. The recovered polymer mass was 93% of the initial, 83% active, with less than 0.5% phosphate, less than 0.1% vinyl sulfonate, and less than 0.1% vinyl phosphonate or vinyl phosphonate.

Figure 6:
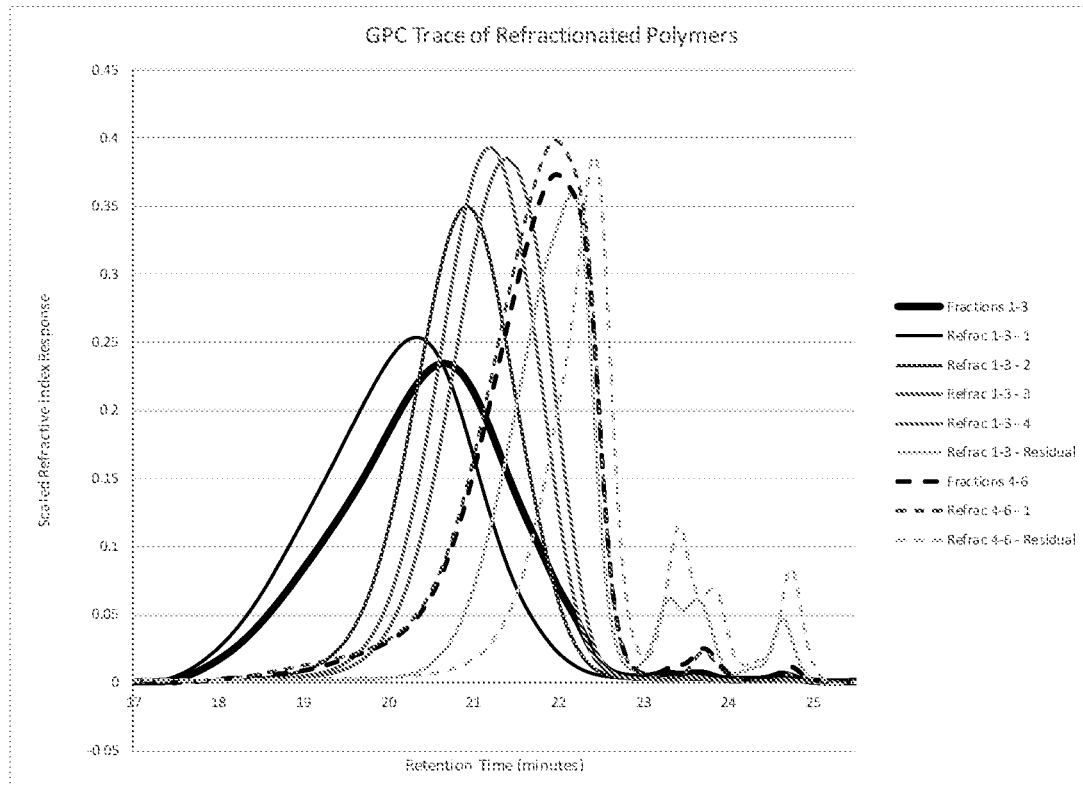
FIG. 6 is a GPC trace plot resulting from polymer analysis.

The GPC trace plot of the resulting refractioned materials is shown in FIG. 6.

In addition to RI detection, light scattering was also performed. While the low retention time samples provide good light scattering, higher retention samples do not. This phenomenon was independently confirmed with a stand-alone light scattering instrument not attached to GPC. Low molecular weight fractions appear to cluster which manifests as high molecular weight and high error after work up of light scattering signal into molecular weight. For this reason, only the molecular weights of the less retained materials are given. For more retained fraction, the trend of increasing calculated Mn and Mw continues with uncertainties approaching 50%. Polymer with Mw of 60,000 Daltons was detected for Refrac 1-3—1. This corresponds to a polymer of between 250 and 450 repeat units depending upon the composition of vinyl sulfonate and vinyl phosphono-phosphate derived units.

TABLE 6

|  | Mn (kDa) | Uncertainty | Mw (kDa) | Uncertainty |
|---|---|---|---|---|
| Fractions 1-3 | 4.4 | 2.50% | 6.5 | 1.60% |
| Refrac 1-3-1 | 5.6 | 1.10% | 6.8 | 0.90% |
| Refrac 1-3-2 | 3.5 | 4.30% | 4.0 | 3.90% |
| Refrac 1-3-3 | 4.0 | 7.50% | 4.9 | 12.30% |
| Refrac 1-3-4 | 4.6 | 7.60% | 6.1 | 18.90% |

Example 62 Identification of End Groups by Different Analytical Techniques

HNMR of the refractionated samples from example 61 showed broad polymer peaks in the olefin region of 6.5-5 ppm. Integration of these peaks versus the non-olefin peaks from 4.0-1.0 ppm can be used to approximate how many olefins are present. Olefin areas were divided by 2 assuming a vinyl like group, while the non-olefins were divided by 3 assuming a $CH_2$—CHX where X is a P or S. From the composition of each fraction, calculated with an internal standard combined HNMR and PNMR, the Mn can be approximated under the assumption that every olefin corresponds to a terminal group. The closeness of this calculation with the light scattering (LS) result for Mn can then be used to gauge if each polymer has an olefin at a terminal position. The comparative results are given in Table 7.

TABLE 7

|  | Mn-LS (kDa) | MW-LS (kDa) | Mn-HNMR (kDa) |
|---|---|---|---|
| Fractions 1-3 | 4.4 | 6.5 | 3.5 |
| Refrac 1-3-1 | 5.6 | 6.8 | 6.8 |
| Refrac 1-3-2 | 3.5 | 4 | 2.7 |
| Refrac 1-3-3 | 4 | 4.9 | 2.3 |
| Refrac 1-3-4 | 4.6 | 6.1 | 2.0 |
| Refrac 1-3-Residual | — | — | 0.8 |
| Fractions 4-6 | — | — | 1.3 |
| Refrac 4-6-1 | — | — | 1.4 |
| Refrac 4-6-Residual | — | — | 1.2 |

For the less retained and presumably higher molecular weight species, the match is quite close, with values of 5.6 vs 6.8 and 3.5 vs. 2.7 for Refrac 1-3—1 and 2. Unlike light scattering, olefin based analysis also indicates that Mn does decrease with higher fractions that are more retained on the columns. To confirm the $CH_2$ nature of the olefins, edited heteronuclear single quantum coherence (Edited-HSQC) NMR was run on sample Refrac 4-6—1. The olefin peaks were confirmed to be of $CH_2$ character.

Sample Refrac 1-3—4 was also analyzed by ion chromatography (Dionex IonPac AS 16-4 µm) followed by high resolution mass spectrometry. In addition to a large broad polymer peak with many signals, a sharp early eluting (less total charge) peak was also seen. This early eluting peak was found to contain and match the multiple masses for a "trimer" of phosphono-phosphate, including the proton form, sodium form, mixtures of proton and sodium as well as masses corresponding to the loss or gain of water and loss of a phosphate group. This species was found to contain an unsaturation, either olefinic or cyclic. Given the Edited-HSQC result, the structure of the fully protonic form is shown.

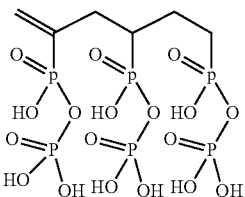

It is assumed that other end groups besides olefins are also present. In the synthesis of the refractionated samples, 0.6% initiator relative to total moles of polymerizable monomers was used. Typical initiator efficiency is less than 100%, but for the sake of calculation this value will be used. Each persulfate can split to form 2 radicals. If each radical starts a polymer chain and the reaction proceeds to completion, each chain is expected to have 83 repeat units. The initial combined fraction 1-3 had an average of 19 repeat units while 4-6 had 6 repeat units from the HNMR data. Therefore, assuming every initiator radical perfectly initiated a polymer, a minimum of 4 chain transfers or backbiting and beta scission combinations took place on that chain, with each transfer likely producing an olefin. Assuming only 40% efficiency of initiation, 208 repeat units is expected meaning 11 chain transfers or backbiting and beta scission combinations occurred from each initiator radical.

It is understood that the examples and embodiments described herein are for illustrative purposes only and that various modifications or changes in light thereof will be suggested to one skilled in the art without departing from its spirit and scope.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising a polymer comprising a phosphono-phosphate group and an anionic group, wherein said polymer has the structure:

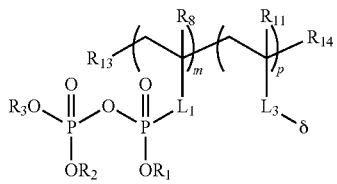

Formula 23 wherein:
R$_1$ is selected from the group consisting of —H, alkyl, alkanediyl-alkoxy, metal salt having Na, K, Ca, Mg, Mn, Zn, Fe, or Sn cation, amine cation salt, and a structure of Formula 2:

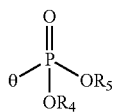

Formula 2 wherein:
θ is the site of attachment to Formula 23,
R$_4$ and R$_5$ are independently selected from the group consisting of —H, alkyl, alkanediyl-alkoxy, metal salt having Na, K, Ca, Mg, Mn, Zn, Fe, or Sn cation, and amine cation salt;
R$_2$ is selected from the group consisting of —H, alkyl, alkanediyl-alkoxy, metal salt having Na, K, Ca, Mg, Mn, Zn, Fe, or Sn cation, amine cation salt, and a structure of Formula 3:

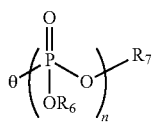

Formula 3 wherein:
θ is the site of attachment to Formula 23,
R$_6$, and R$_7$ are independently selected from the group consisting of —H, alkyl, alkanediyl-alkoxy, metal salt having Na, K, Ca, Mg, Mn, Zn, Fe, or Sn cation, and amine cation salt, and
n is an integer from 1 to 22; and
R$_3$ is selected from the group consisting of —H, alkyl, alkanediyl-alkoxy, metal salt having Na, K, Ca, Mg, Mn, Zn, Fe, or Sn cation, and amine cation salt, and said anionic group is covalently bound to the polymer backbone, side group, or side chain and is selected from the chemical group consisting of phosphate, phosphonate, phosphinate, sulfate, sulfonate, sulfinate, mercapto, carboxylate, hydroxyamino, amine oxide, and hydroxamate,
R$_8$ is selected from the group consisting of —H and —CH$_3$;
L$_1$ is selected from the group consisting of a chemical bond, arenediyl, and a structure of Formula 5:

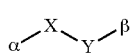

Formula 5 wherein:
α is the site of attachment to the polymer backbone;
β is the site of attachment to the phosphono-phosphate;
X is selected from the group consisting of the structures in Formulas 6-12;

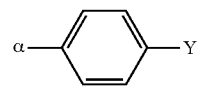

Formula 6

Formula 7

Formula 8

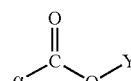

Formula 9

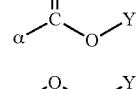

Formula 10

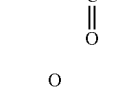

Formula 11

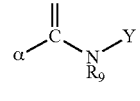

Formula 12

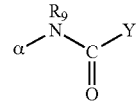

wherein:
R$_9$ is selected from the group consisting of —H, alkyl$_{(C1-8)}$, phosphonoalkyl, and phosphono(phosphate)alkyl; and
Y is selected from the group consisting of alkanediyl, alkoxydiyl, alkylaminodiyl and alkenediyl,
R$_{11}$ is selected from the group consisting of —H and —CH$_3$;
δ is the site of attachment to the anionic group;
L$_3$ is selected from a chemical bond, arenediyl, and a structure of Formula 15;

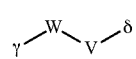

Formula 15 wherein:
γ is the site of attachment to the polymer backbone;
δ is the site of attachment to the anionic group;
W is selected from the structures in Formulas 16-22:

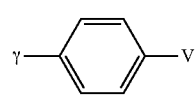

Formula 16

-continued

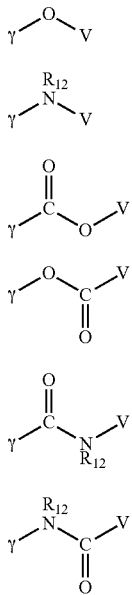

Formula 17

Formula 18

Formula 19

Formula 20

Formula 21

Formula 22 wherein:
 $R_{12}$ is selected from the group consisting of —H and alkyl$_{(C1-8)}$; and
 V is selected from the group consisting of alkanediyl, alkoxydiyl, alkylaminodiyl or alkenediyl;
 $R_{13}$ is a chemical group resulting from polymer initiation;
 $R_{14}$ is a chemical group resulting chain termination;
 m is an integer from 2 to 450; and
 p is an integer from 2 to 450.

2. The oral care composition of claim 1 wherein $R_2$ is a group having a structure:

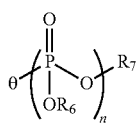

Formula 3 wherein:
 θ is the site of attachment to Formula 23,
 $R_6$, and $R_7$ are independently selected from the group consisting of —H, alkyl, alkanediyl-alkoxy, metal salt having Na, K, Ca, Mg, Mn, Zn, Fe, or Sn cation, and amine cation salt, and
 n is an integer from 1 to 3.

3. The oral care composition of claim 1 wherein $R_8$ is H.

4. The oral care composition of claim 1 wherein $L_1$ is a group having the structure:

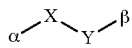

Formula 5 wherein:
 α is the site of attachment to the polymer backbone;
 β is the site of attachment to the phosphono-phosphate;
 X is selected from the group consisting of the structures:

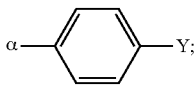

Formula 6

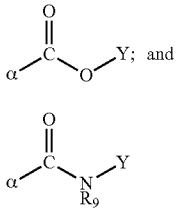

Formula 9

Formula 11 wherein:
 $R_9$ is selected from the group consisting of —H, alkyl$_{(C1-8)}$, phosphonoalkyl, and phosphono(phosphate)alkyl; and
 Y is selected from the group consisting of alkanediyl, alkoxydiyl, alkylaminodiyl and alkenediyl.

5. The oral care composition of claim 1 wherein said anionic group is selected from the group consisting of phosphate, phosphonate, sulfate, sulfonate, and carboxylate.

6. The oral care composition of claim 1 wherein $R_{11}$ is H.

7. The oral care composition of claim 1 wherein $L_3$ is a group having the structure:

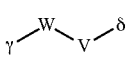

Formula 15 wherein:
 W is selected from the group consisting of the structures:

Formula 16

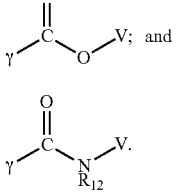

Formula 19

Formula 21

8. The oral care composition of claim 1 wherein $R_{13}$ is selected from the group consisting of the structures:

Formula 24

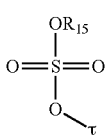

Formula 25

-continued

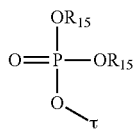

Formula 26

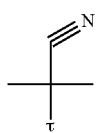

Formula 27

Formula 28 wherein:
$R_{15}$ is selected from the group consisting of —H, Na, K and amine cation salt;
τ is the site of attachment to polymer backbone; and
Q is the non-olefin residue of a monomer used in polymerization.

9. The oral care composition of claim 8 wherein Q has the structure:

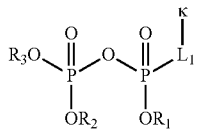

Formula 29 wherein κ denotes the site of attachment to Formula 28.

10. The oral care composition of claim 8 wherein Q has the structure:

Formula 30 wherein κ denotes the site of attachment to Formula 28.

11. The oral care composition of claim 1 wherein $R_{14}$ is —H.

12. The oral care composition of claim 1 wherein $R_{14}$ is another polymer chain with a head to head attachment.

13. The oral care composition of claim 1 wherein:
$R_1$, $R_2$, and $R_3$ are independently selected from the group consisting of H, Na salt, K salt and amine cation salt;
$R_8$ is H;
$L_1$ is a covalent bond;
$L_3$ is a covalent bond;
the anionic group is sulfonate;
$R_{13}$ has the structure:

Formula 28 wherein τ is the site of attachment to polymer backbone; and
Q has a structure selected from the group consisting of:

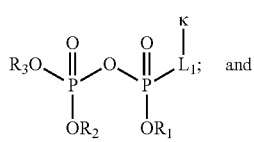

Formula 29

Formula 30 wherein κ denotes the site of attachment to Formula 28; and
$R_{14}$ is H.

14. The oral care composition of claim 1 wherein said composition further comprises from about 5% to about 70%, by weight of the composition, of water.

15. The oral care composition of claim 1 wherein said composition further comprises from about 0.1% to about 11%, by weight of the composition, of a metal ion salt.

16. The oral care composition of claim 15 wherein said metal ion salt is stannous fluoride.

* * * * *